United States Patent
Boiteau et al.

(10) Patent No.: US 8,404,836 B2
(45) Date of Patent: Mar. 26, 2013

(54) 3-PHENYL ACRYLIC ACID COMPOUND ACTIVATORS OF TYPE PPAR RECEPTORS AND PHARMACEUTICAL/COSMETIC COMPOSITIONS COMPRISED THEREOF

(75) Inventors: Jean-Guy Boiteau, Valbonne (FR); Laurence Clary, La Colle sur Loup (FR); Jean-Claude Pascal, Nice (FR); Sandrine Chambon, Le Cannet (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 12/632,257

(22) Filed: Dec. 7, 2009

(65) Prior Publication Data
US 2010/0144884 A1    Jun. 10, 2010

Related U.S. Application Data

(63) Continuation of application No. PCT/FR2008/050997, filed on Jun. 4, 2008.

(30) Foreign Application Priority Data

Jun. 5, 2007 (FR) .................................. 07 55478

(51) Int. Cl.
*C07D 345/00* (2006.01)
*C07D 517/00* (2006.01)
(52) U.S. Cl. .................. 540/1; 514/570; 562/465
(58) Field of Classification Search .................. 514/570; 562/465
See application file for complete search history.

(56) References Cited

FOREIGN PATENT DOCUMENTS

| WO | WO 99/62871 A1 | 12/1999 |
| WO | WO 01/40172 A1 | 6/2001 |
| WO | WO 2007/049158 A2 | 5/2007 |
| WO | WO 2008/152334 A3 | 12/2008 |

OTHER PUBLICATIONS

The Preliminary International Report on Patentability dated Dec. 7, 2009, with Written Opinion of the International Searching Authority issued in connecion with corresponding PCT/FR2008/050997, in French, and an English translation of separate pages.

*Primary Examiner* — Brandon Fetterolf
*Assistant Examiner* — Jean Cornet
(74) *Attorney, Agent, or Firm* — SNR Denton US LLP

(57) ABSTRACT

Novel 3-phenyl acrylic acid compounds have the following general formula (I):

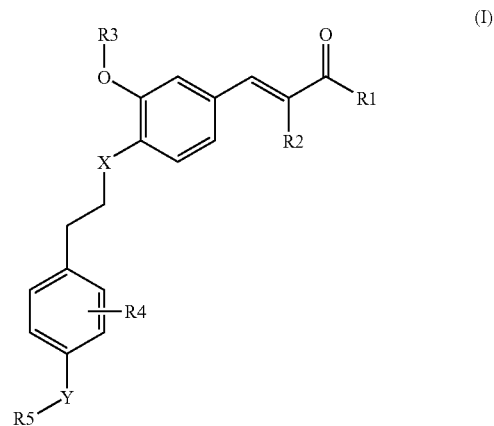

and are formulated into pharmaceutical compositions for administration in human or veterinary medicine (in dermatology, as well as in the field of cardiovascular diseases, immune diseases and/or diseases associated with lipid metabolism), or into cosmetic compositions.

44 Claims, 5 Drawing Sheets

3-PHENYL ACRYLIC ACID COMPOUND ACTIVATORS OF TYPE PPAR RECEPTORS AND PHARMACEUTICAL/COSMETIC COMPOSITIONS COMPRISED THEREOF

CROSS-REFERENCE TO PRIORITY/PCT APPLICATIONS

This application is a continuation of PCT/FR 2008/050997, filed Jun. 4, 2008, and designating the United States (published in the French language on Dec. 18, 2008 as WO 2008/152334 A2; the title and abstract were also published in English), which claims priority under 35 U.S.C §119 of FR 0755478, filed Jun. 5, 2007, each hereby expressly incorporated by reference in its entirety and each assigned to the assignee hereof.

BACKGROUND OF THE INVENTION

1. Technical Field of the Invention

The present invention relates to a class of derivatives of 3-phenyl acrylic acid that are activators of receptors of the Peroxisome Proliferator-Activated Receptor type, of subtype γ (PPARγ), as novel and useful industrial compounds. It also relates to their method of preparation and their formulation into pharmaceutical compositions useful in human or veterinary medicine, or in cosmetic compositions.

2. Description of Background and/or Related and/or Prior Art

The activity of the PPAR type receptors has been the subject of numerous studies. One example is the publication "Differential Expression of Peroxisome Proliferator-Activated Receptor Subtypes during the Differentiation of Human Keratinocytes", Michel Rivier et al., *J. Invest. Dermatol.*, 111, 1998, p 1116-1121, which lists a large number of bibliographical references concerning the PPAR type receptors. Another example is the report "The PPARs: From orphan receptors to Drug Discovery", Timothy M. Willson, Peter J. Brown, Daniel D. Sternbach, and Brad R. Henke, *J. Med. Chem.*, 2000, Vol. 43, p. 527-550.

The PPARs activate transcription by binding to elements of DNA sequences, known as the peroxisome proliferator response elements (PPRE), in the form of a heterodimer with the retinoid X receptors (known as RXRs).

Three subtypes of human PPARs have been identified and described: PPARα, PPARγ and PPARδ (or NUC1).

PPARα is mainly expressed in the liver whereas PPARδ is ubiquitous.

Of the three subtypes, PPARγ has received the most study. All of the references suggest a critical role of the PPARγ in regulation of the differentiation of adipocytes, where it is strongly expressed. It also plays a key role in systemic lipid homeostasis.

It was notably described in international application WO 96/33724 that selective compounds of the PPARγ, such as a prostaglandin-J2 or -D2, are potential actives for the treatment of obesity and diabetes.

Moreover, the assignee hereof has already described in WO 02/12210, WO 03/055867 and WO 2006/018326 the formulation of diaromatic compounds that are activators of the type PPARγ receptors into pharmaceutical compositions, such compositions being useful for the treatment of skin disorders linked to an abnormality of differentiation of the epidermal cells.

Nevertheless, need still exists for novel compounds that are activators of the type PPARγ receptors and display advantageous pharmaceutical properties.

SUMMARY OF THE INVENTION

Novel derivatives of 3-phenyl acrylic acid have now been developed which, surprisingly, display activity with respect to the PPAR-gamma receptors.

Moreover, the compounds according to the present invention are most often obtained in solid form, which has the advantage that it makes their synthesis and their purification easier.

Finally, using solid compounds for the preparation of pharmaceutical and/or cosmetic compositions offers a real advantage within the scope of their pharmaceutical and/or cosmetic development because the level of residual solvents that these compounds contain is almost zero, relatively to what they can contain when they are in the form of an oil.

Thus, the present invention features compounds corresponding to the following general formula (I):

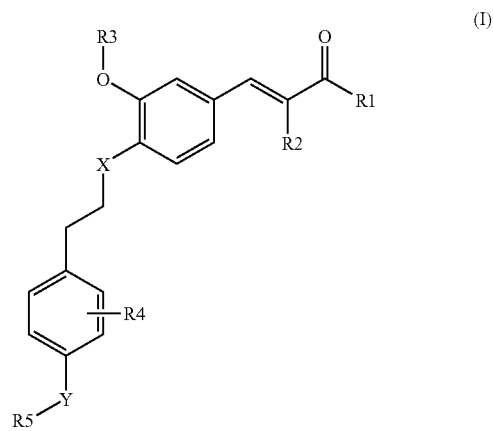

in which:
R1 is a hydroxyl radical or an alkoxy radical;
R2 is an alkyl radical, an alkoxy radical or an aralkoxy radical;
R3 is a hydrogen atom, an alkyl radical, an optionally substituted aralkyl radical or a polyether radical;
R4 is a hydrogen atom, a halogen, an alkyl radical or an alkoxy radical;
R5 is an alkyl radical, an optionally substituted aryl radical or an optionally substituted aralkyl radical;
X is an oxygen atom or a $CH_2$ radical;
Y is an oxygen atom, an NR6 radical, an $OSO_2$, OCO, NR6CO or $NR6SO_2$ radical,
R6 is a hydrogen atom or an alkyl radical;
and also the salts thereof with a pharmaceutically acceptable acid or base, and pharmaceutically acceptable solvates and hydrates thereof.

DETAILED DESCRIPTION OF BEST MODE AND SPECIFIC/PREFERRED EMBODIMENTS OF THE INVENTION

In particular, when the compounds according to the invention are in the form of a salt, it is a salt of an alkali metal, in particular a salt of sodium or of potassium, or a salt of an alkaline-earth metal, in particular magnesium or calcium, or a salt with an organic amine, more particularly with an amino acid such as arginine or lysine.

When the compounds according to the invention possess an amine function and are in the form of a salt of this amine, it is a salt of an inorganic acid, for example hydrochloric acid, sulfuric acid, or hydrobromic acid or a salt of an organic acid, for example acetic acid, triflic acid, tartaric acid, oxalic acid, citric acid, trifluoroacetic acid or methanesulfonic acid.

According to the present invention, alkyl radical means a linear or branched saturated hydrocarbon chain, having from 1 to 12 carbon atoms and, more particularly, from 1 to 6 carbon atoms.

Preferably, the alkyl radicals of the present invention are selected from among methyl, ethyl, propyl, isopropyl, butyl, isobutyl, tert-butyl, pentyl, isoamyl, amyl, hexyl, heptyl, octyl and decyl radicals. More particularly, the alkyl radicals are selected from among methyl, ethyl, propyl, isopropyl, butyl, isobutyl, tert-butyl, pentyl, isoamyl, amyl and hexyl radicals.

According to the present invention, lower alkyl radical means an alkyl radical as previously defined and having from 1 to 4 carbon atoms and, advantageously, 1 to 3 carbon atoms. Thus, preferably, said radicals are selected from among methyl, ethyl, propyl, isopropyl, butyl, isobutyl and tert-butyl radicals.

According to the present invention, aryl radical means a phenyl or an unsubstituted naphthyl.

According to the present invention, substituted aryl radical means a phenyl or a naphthyl substituted with one or more atoms or groups of atoms selected from among alkyl, alkoxy, halogen, hydroxy, cyano, trifluoromethyl and nitro.

The substituted aryl radical is preferably selected from among phenyl radicals monosubstituted with a lower alkoxy radical and the naphthyl radicals monosubstituted with a lower alkyl radical.

According to the present invention, aralkyl radical means an alkyl substituted with a phenyl or an unsubstituted naphthyl.

Preferably, the aralkyl radical is a benzyl or phenethyl radical.

According to the present invention, substituted aralkyl radical means an aralkyl radical substituted with one or more atoms or groups of atoms selected from among alkyl, alkoxy, halogen, hydroxy, cyano, trifluoromethyl and nitro.

The substituted aralkyl radical is preferably selected from among phenethyl and benzyl radicals monosubstituted with a lower alkyl radical.

According to the present invention, halogen atom means an atom of fluorine, of chlorine, of bromine or of iodine.

According to the present invention, hydroxyl radical means the —OH radical.

According to the present invention, alkoxy radical means an oxygen atom substituted with an alkyl.

The alkoxy radicals are preferably the methoxy, ethoxy, isopropyloxy, n-propyloxy, tert-butoxy, n-butoxy, n-pentyloxy and n-hexyloxy radicals.

According to the present invention, lower alkoxy radical means an oxygen atom substituted with a lower alkyl.

According to the present invention, aralkoxy radical means an oxygen atom substituted with an aralkyl.

According to the present invention, polyether radical means a radical having from 1 to 7 carbon atoms interrupted by at least one oxygen atom. Preferably, the polyether radical is selected from radicals such as methoxyethoxy, ethoxyethoxy, ethoxyethyl or methoxyethoxyethoxy.

Among the compounds of general formula (I) above according to the present invention, the following are especially preferred:

1. (Z)-3-(4-{2-[4-(butane-1-sulfonyloxy)-phenyl]-ethoxy}-3-methoxy-phenyl)-2-ethoxy-acrylic acid;
2. (Z)-3-(4-{3-[4-(butane-1-sulfonyloxy)-3-methoxy-phenyl]-propyl}-3-butoxy-phenyl)-2-methoxy-acrylic acid;
3. (Z)-3-(4-{3-[4-(butane-1-sulfonyloxy)-3-methoxy-phenyl]-propyl}-3-butoxy-phenyl)-2-ethoxy-acrylic acid;
4. (E)-3-(4-{3-[4-(butane-1-sulfonyloxy)-3-methoxy-phenyl]-propyl}-3-butoxy-phenyl)-2-methyl-acrylic acid;
5. (Z)-3-{3-butoxy-4-[2-(4-methanesulfonyloxy-phenyl)-ethoxy]-phenyl}-2-ethoxy-acrylic acid;
6. (Z)-3-(4-{2-[4-(butane-1-sulfonyloxy)-phenyl]-ethoxy}-3-butoxy-phenyl)-2-ethoxy-acrylic acid;
7. (Z)-3-{3-butoxy-4-[2-(4-methanesulfonyloxy-3-methoxy-phenyl)-ethoxy]-phenyl}-2-ethoxy-acrylic acid;
8. (Z)-3-(4-{2-[4-(butane-1-sulfonyloxy)-3-methoxy-phenyl]-ethoxy}-3-butoxy-phenyl)-2-ethoxy-acrylic acid;
9. (Z)-3-(4-{2-[4-(butane-1-sulfonyloxy)-2-methoxy-phenyl]-ethoxy}-3-butoxy-phenyl)-2-ethoxy-acrylic acid;
10. (Z)-3-{3-butoxy-4-[2-(4-methanesulfonyloxy-2-methoxy-phenyl)-ethoxy]-phenyl}-2-ethoxy-acrylic acid;
11. (Z)-3-{3-butoxy-4-[2-(4-ethoxy-3-fluoro-phenyl)-ethoxy]-phenyl}-2-ethoxy-acrylic acid;
12. (Z)-3-{3-butoxy-4-[2-(3-fluoro-4-pentyloxy-phenyl)-ethoxy]-phenyl}-2-ethoxy-acrylic acid;
13. (Z)-3-(4-{2-[4-(butane-1-sulfonyloxy)-3-fluoro-phenyl]-ethoxy}-3-butoxy-phenyl)-2-ethoxy-acrylic acid;
14. (Z)-3-{3-butoxy-4-[2-(3-chloro-4-ethoxy-phenyl)-ethoxy]-phenyl}-2-ethoxy-acrylic acid;
15. (Z)-3-{3-butoxy-4-[2-(3-chloro-4-pentyloxy-phenyl)-ethoxy]-phenyl}-2-ethoxy-acrylic acid;
16. (Z)-3-{3-butoxy-4-[2-(3-chloro-4-methanesulfonyloxy-phenyl)-ethoxy]-phenyl}-2-ethoxy-acrylic acid);
17. (Z)-3-(4-{2-[4-(butane-1-sulfonyloxy)-3-chloro-phenyl]-ethoxy}-3-butoxy-phenyl)-2-ethoxy-acrylic acid;
18. (Z)-2-ethoxy-3-{4-[2-(4-methanesulfonyloxy-phenyl)-ethoxy]-3-methoxy-phenyl}-acrylic acid;
19. (Z)-2-ethoxy-3-{4-[2-(4-ethoxy-phenyl)-ethoxy]-3-methoxy-phenyl}-acrylic acid;
20. (Z)-2-ethoxy-3-{3-methoxy-4-[2-(4-pentyloxy-phenyl)-ethoxy]-phenyl}-acrylic acid;
21. (Z)-3-{4-[2-(4-acetylamino-phenyl)-ethoxy]-3-butoxy-phenyl}-2-ethoxy-acrylic acid;
22. (Z)-3-(4-{2-[4-(butane-1-sulfonylamino)-phenyl]-ethoxy}-3-butoxy-phenyl)-2-ethoxy-acrylic acid;
23. (Z)-3-(3-butoxy-4-{2-[4-(methanesulfonyl-methyl-amino)-phenyl]-ethoxy}-phenyl)-2-ethoxy-acrylic acid;
24. (Z)-3-{3-butoxy-4-[2-(4-methanesulfonylamino-phenyl)-ethoxy]-phenyl}-2-ethoxy-acrylic acid;
25. (Z)-3-[4-(2-{4-[(butane-1-sulfonyl)-methyl-amino]-phenyl}-ethoxy)-3-butoxy-phenyl]-2-ethoxy-acrylic acid;
26. (Z)-3-{3-butoxy-4-[3-(4-methoxy-phenyl)-propyl]-phenyl}-2-ethoxy-acrylic acid;
27. (Z)-3-(4-{2-[4-(acetyl-methyl-amino)-phenyl]-ethoxy}-3-butoxy-phenyl)-2-ethoxy-acrylic acid;
28. (Z)-3-{3-butoxy-4-[2-(4-propionylamino-phenyl)-ethoxy]-phenyl}-2-ethoxy-acrylic acid;
29. (E)-3-(4-{3-[4-(butane-1-sulfonyloxy)-phenyl]-propyl}-3-butoxy-phenyl)-2-methoxy-acrylic acid;
30. (Z)-3-[4-{3-[4-(butane-1-sulfonyloxy)-phenyl]-propyl}-3-(2-ethoxy-ethoxy)-phenyl]-2-methoxy-methyl acrylate;
31. (E)-3-(4-{2-[4-(butane-1-sulfonyloxy)-phenyl]-ethoxy}-3-butoxy-phenyl)-2-methoxy-acrylic acid;
32. (Z)-3-(4-{2-[4-(butane-1-sulfonyloxy)-phenyl]-ethoxy}-3-butoxy-phenyl)-2-ethoxy-ethyl acrylate;
33. (Z)-3-(4-{2-[4-(benzoyl-methyl-amino)-phenyl]-ethoxy}-3-butoxy-phenyl)-2-methoxy-acrylic acid;
34. (Z)-3-[4-{2-[4-(butane-1-sulfonylamino)-phenyl]-ethoxy}-3-(2-ethoxy-ethoxy)-phenyl]-2-ethoxy-acrylic acid;
35. (Z)-3-(3-butoxy-4-{2-[4-(2-m-tolyl-ethanesulfonylamino)-phenyl]-ethoxy}-phenyl)-2-ethoxy-acrylic acid;

36. (Z)-3-(3-butoxy-4-{2-[4-(3-ethoxy-benzoylamino)-phenyl]-ethoxy}-phenyl)-2-ethoxy-acrylic acid;
37. (Z)-3-(3-butoxy-4-{2-[4-(methyl-naphthalen-1-ylmethyl-amino)-phenyl]-ethoxy}-phenyl)-2-methoxy-acrylic acid;
38. (Z)-3-{3-benzyloxy-4-[3-(4-m-tolylmethanesulfonyloxy-phenyl)-propyl]-phenyl}-2-methoxy-acrylic acid; and
39. (Z)-3-{3-hydroxy-4-[3-(4-m-tolylmethanesulfonyloxy-phenyl)-propyl]-phenyl}-2-methoxy-acrylic acid.

According to the present invention, the preferred compounds corresponding to general formula (I) are those that have at least one of the following characteristics:
R1 is a hydroxyl radical,
R2 is a lower alkyl radical or a lower alkoxy radical,
R3 is an alkyl radical or a polyether radical,
R4 is a hydrogen atom, a lower alkoxy radical or a halogen,
R5 is an alkyl radical,
X is an oxygen atom or a $CH_2$ group,
Y is a group $-NR6SO_2$ or a group $-OSO_2$ with R6 as previously defined.

According to the present invention, the particularly preferred compounds corresponding to general formula (I) are those that have at least one of the following characteristics:
R1 is a hydroxyl radical,
R2 is a lower alkoxy radical,
R3 is an alkyl radical,
R4 is a hydrogen atom, a lower alkoxy radical or a halogen,
R5 is an alkyl radical,
X is an oxygen atom or a $CH_2$ group,
Y is a group $-OSO_2$.

A general description of the methods of preparation of the compounds of general formula (I) is given below, referring to the schemes in FIGS. 1, 2, 3, 4 and 5. In these schemes and in the description of the method that follows, unless specified otherwise, all of the substituents are as defined for the compounds of general formula (I).

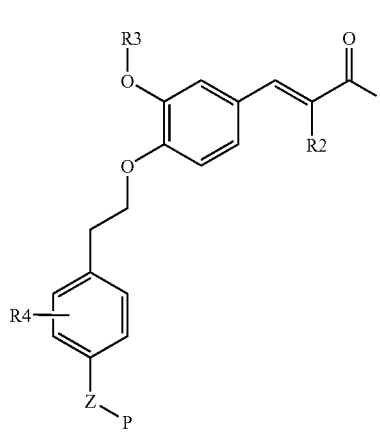

Z = NH, O
P = protecting group

The derivatives (3) can be obtained by Mitsunobu reaction from the derivatives of general formula (1):

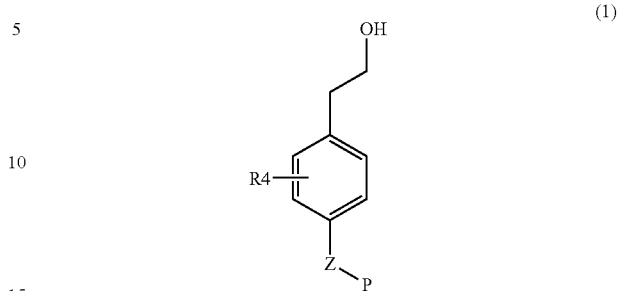

and the compounds of general formula (2)

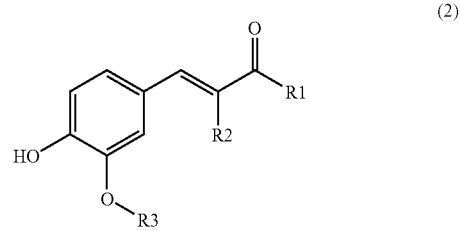

in the presence of triphenylphosphine and diethylazodicarboxylate for example.

Figure 2:
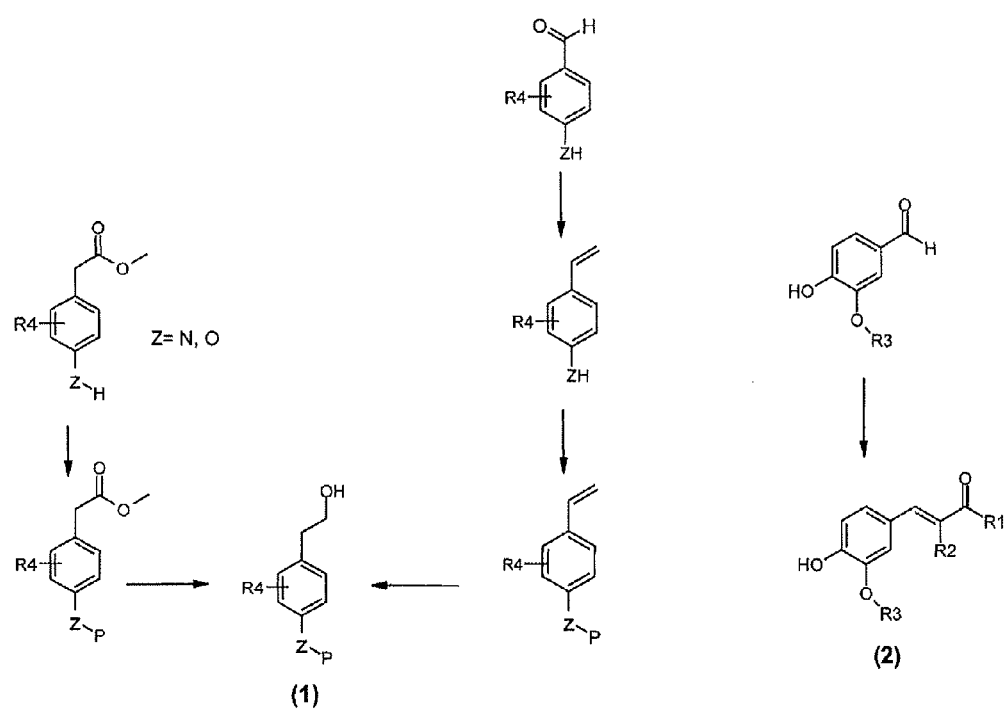

The scheme in FIG. 2 describes methods of obtaining the derivatives of general formula (1) and (2).

The compounds of general formula (2) are generally obtained by Wittig reaction or Horner-Emmons reaction from their aldehyde precursors and phosphonates (for example (diethoxy-phosphoryl)-ethoxy-ethyl acetate) or corresponding phosphoniums (for example, 1-methoxycarbonyl-ethyl-triphenyl phosphonium chloride).

The derivatives of general formula (1) can be obtained after reaction of protection by a group P from intermediates of type (4-amino-phenyl)-methyl acetate, (4-hydroxy-phenyl)-methyl acetate then reduction by lithium borohydride or from intermediates of type 4-aminobenzaldehyde, 4-hydroxybenzaldehyde by Horner-Emmons reaction with diethyl methylphosphonate then protection of group Z and oxidation in the presence of the dimer of 9-borabicyclo[3.3.1]nonane.

Figure 1:
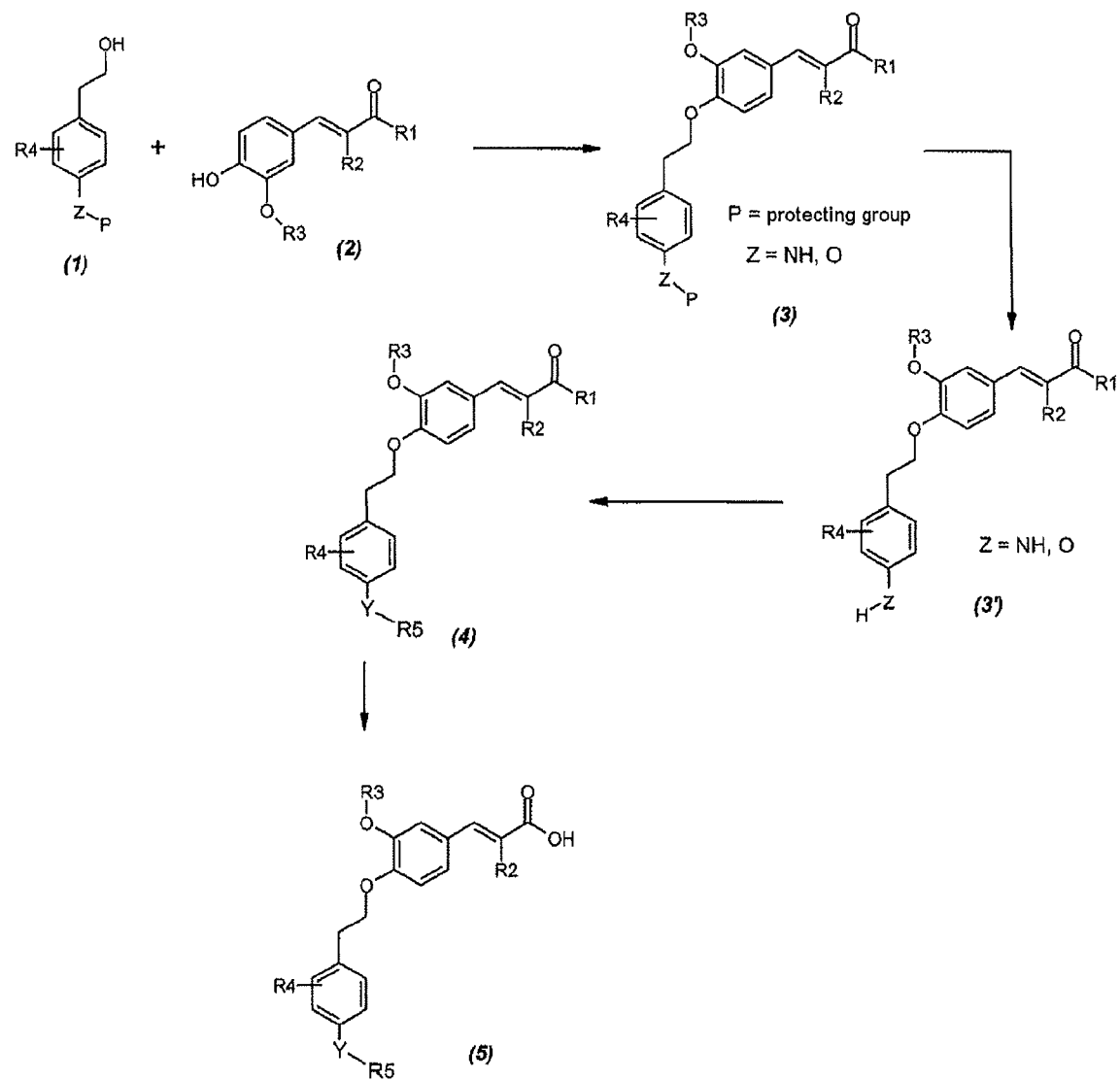
As shown in FIG. 1, the compounds of general formula (I) for which X=O can be obtained from the intermediates of general formula (3)

As shown in FIG. 1, after deprotection of the protecting group P of the compounds of general formula (3), we obtain the compounds of general formula (3').

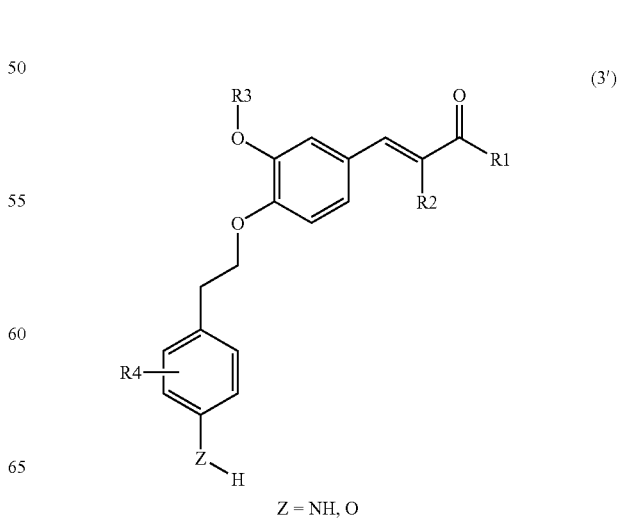

Z = NH, O

The process of preparing, from the compounds of general formula (3'), the compounds of general formula (4):

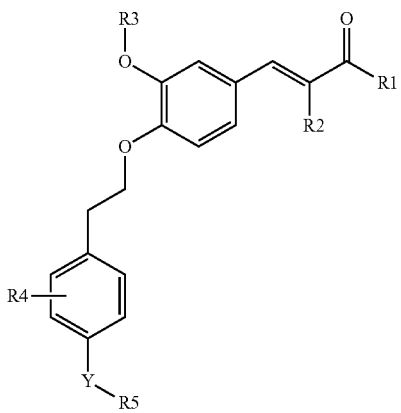
(4)

comprises the following stages:
a) either an addition on a sulfonic acid chloride (R5SO$_2$Cl)
b) or an addition on a carboxylic acid halide (for example R5COCl)
c) or reaction with a halogenated derivative (for example R5Br or R5Cl) in the presence of a base such as sodium hydride or potassium carbonate.

The derivatives thus obtained can optionally be alkylated by reaction with a halogenated derivative (for example R6Br or R6Cl) in the presence of a base such as sodium hydride or potassium carbonate.

Figure 3:
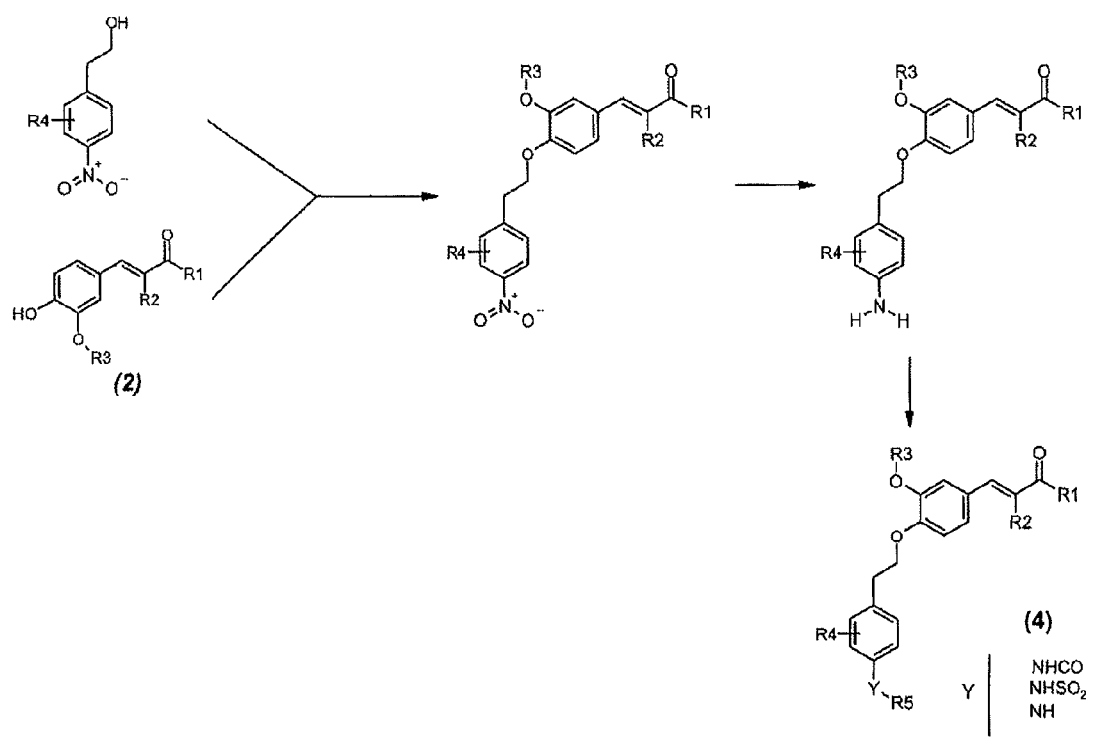

In the case of the compounds for which Y corresponds to a group of type NR6, NR6CO or NR6SO$_2$, compounds (4) can also be obtained from 4-nitrophenethyl alcohol derivatives by Mitsunobu reaction with compound (2) for example, then reduction of the nitro group to an amine function in the presence of tin chloride dihydrate for example (FIG. 3).

The compounds of general formula (5):

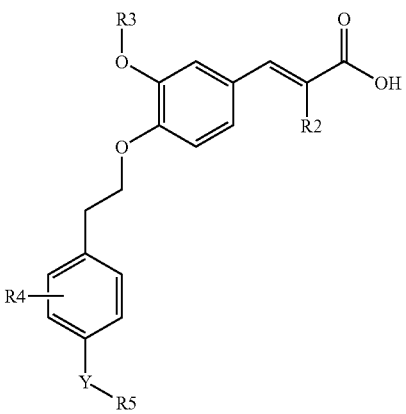
(5)

are then obtained by a reaction of saponification of the compounds of general formula (4) in the presence of sodium hydroxide in a mixture of tetrahydrofuran and water or acetone and water for example.

Figure 4:
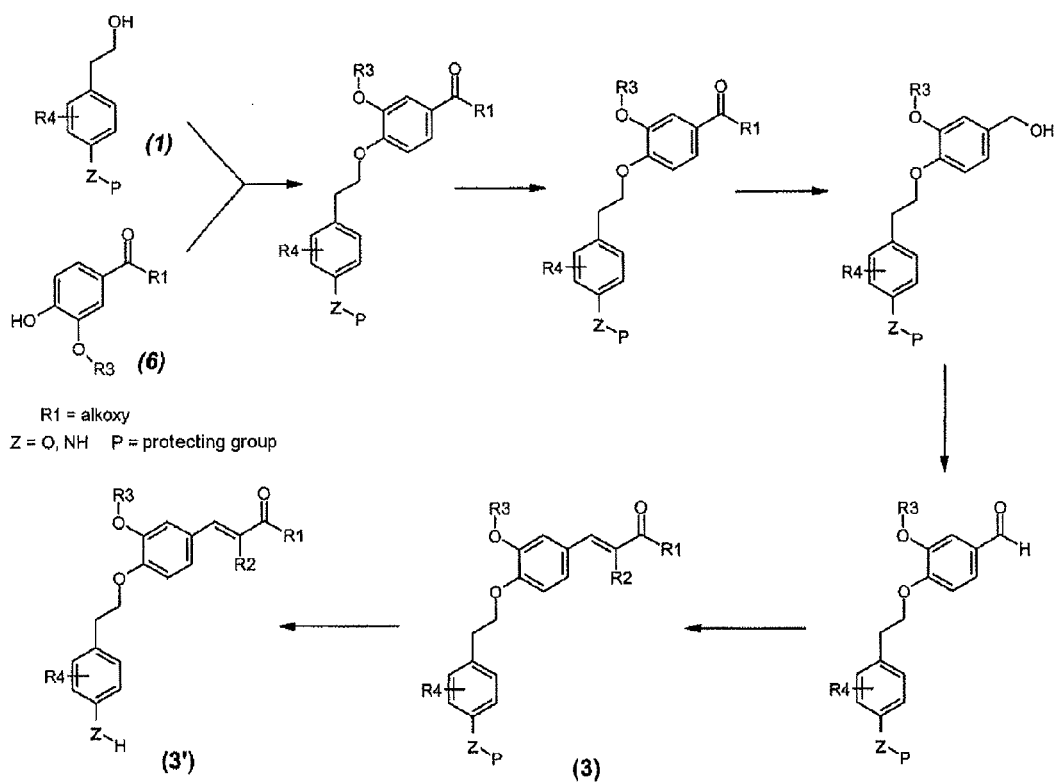

Another alternative for obtaining the compounds of general formula (I) with X=O is shown in the reaction scheme in FIG. 4 using reaction conditions similar to those used in the reaction scheme in FIG. 1.

Figure 5:
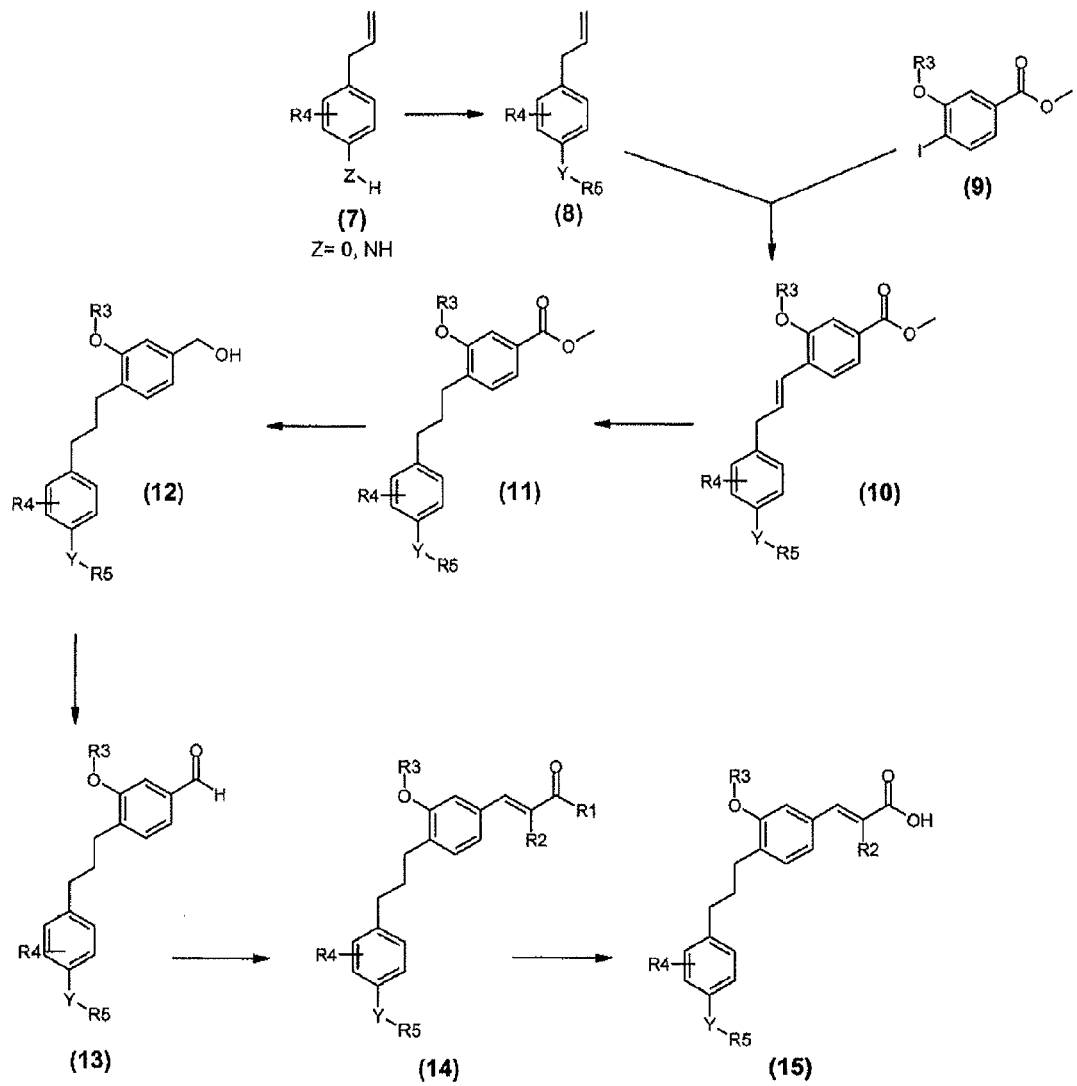

As shown in FIG. 5, the compounds of general formula (I) for which X=CH$_2$ can be obtained from the intermediates of general formula (10):

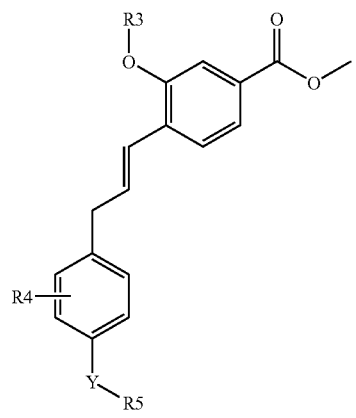
(10)

The derivatives of general formula (10) can be obtained by a reaction of the Heck type from the compounds of general formula (8):

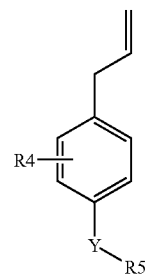
(8)

and a benzene halide (the iodinated derivatives (9) for example),

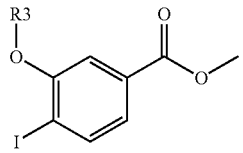
(9)

in the presence of a palladium catalyst (for example, palladium(II) acetate in the presence of a phosphine).

The method for synthesis of the compounds of general formula (8) from derivatives of type 4-allylphenol or 4-allylphenylamine (compound (7) in FIG. 5) comprises the following stages:
a) either addition on a sulfonic acid chloride (R5SO$_2$Cl)
b) or addition on a carboxylic acid halide (for example R5COCl)
c) or reaction with a halogenated derivative (for example R5Br or R5Cl) in the presence of a base such as sodium hydride or potassium carbonate.

The derivatives thus obtained can optionally be alkylated by reaction with a halogenated derivative (for example R6Br or R6Cl) in the presence of a base such as sodium hydride or potassium carbonate.

The iodinated derivatives (9) are previously prepared by iodination of 3-hydroxybenzoic acid, esterification and substitution of the phenol with a halogenated derivative of type R3Br for example.

After hydrogenation of the double bond in the compounds of general formula (10), we obtain the compounds of general formula (11).

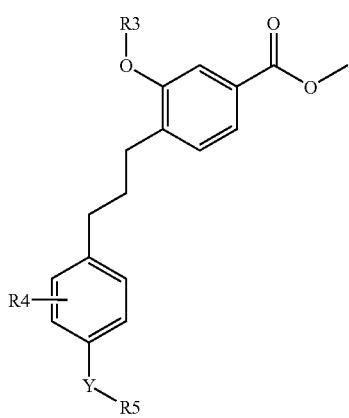

(11)

The method of preparing, from the compounds of general formula (11), the compounds of general formula (15) comprises the following stages:

a) reduction of the methyl ester to alcohol of general formula (12)

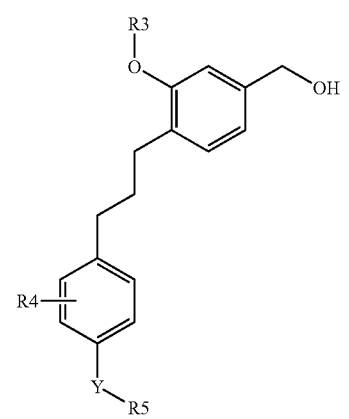

(12)

in the presence of a reducing agent such as lithium borohydride for example.

b) oxidation of the alcohol of general formula (12) to aldehyde of general formula (13)

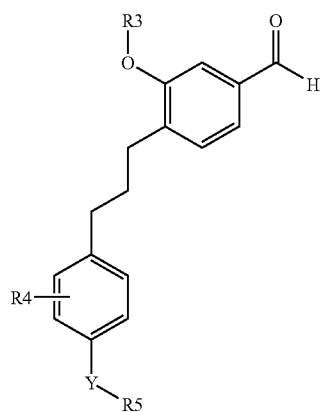

(13)

in the presence of an oxidizing agent such as manganese dioxide for example.

c) a Wittig or Horner-Emmons reaction from the aldehyde precursors of general formula (13) and the phosphonates (for example (diethoxy-phosphoryl)-ethoxy-ethyl acetate) or corresponding phosphoniums (for example, 1-methoxy-carbonyl-ethyl-triphenyl phosphonium chloride) to give the compounds of general formula (14).

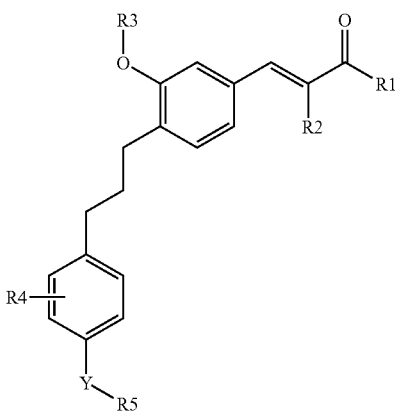

(14)

d) a reaction of saponification of the compounds of general formula (14) in the presence of sodium hydroxide for example in a mixture of tetrahydrofuran and water or in a mixture of acetone and water to give the compounds of general formula (15).

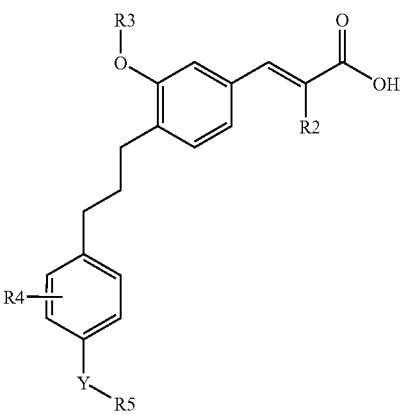

(15)

The functional groups optionally present in the reaction intermediates used in the method can be protected, either permanently or temporarily, by protecting groups which ensure a one-way synthesis of the expected compounds. The reactions of protection and deprotection are carried out according to techniques that are well known one skilled in the art. Temporary protecting group of the amines, alcohols or carboxylic acids means the protecting groups such as those described in "Protective Groups in Organic Chemistry", ed. McOmie J. W. F., Plenum Press, 1973, in "Protective Groups in Organic Synthesis", 2nd edition, Greene T. W. and Wuts P. G. M., publ. John Wiley and Sons, 1991 and in "Protecting Groups", Kocienski P. J., 1994, Georg Thieme Verlag.

The compounds according to the invention display properties of modulating the PPAR type receptors. This activity on the PPARα, δ and γ receptors is measured in a transactivation test and quantified by the dissociation constant Kdapp (apparent), as described in Example 29.

The preferred compounds of the present invention have a dissociation constant less than or equal to 1,000 nM, and advantageously less than or equal to 100 nM.

Preferably, the compounds are modulators of the receptors of specific type PPARγ, i.e., they have a ratio of the Kdapp for the PPARα or PPARδ receptors, to the Kdapp for the PPARγ receptors, greater than or equal to 10. Preferably, this ratio PPARα/PPARγ or PPARδ/PPARγ is greater than or equal to 50 and more advantageously greater than or equal to 100.

The present invention also features the compounds of general formula (I) as described above as medicinal products.

Thus, the compounds as described previously according to the invention can be formulated into medicinal products useful to regulate and/or restore the metabolism of skin lipids.

The present invention also features medicaments comprising the compounds of formula (I) and administration thereof in the treatment and/or prevention of the following disorders.

The compounds according to the invention are particularly suitable in the following treatment areas, whether regime or regimen:

1) for treating dermatological conditions and afflictions associated with a disorder of keratinization affecting differentiation and proliferation, notably for treating acne vulgaris, comedo acne, polymorphic acne, acne rosacea, nodulocystic acne, acne conglobata, senile acne, secondary acnes such as sun-induced, drug-induced or occupational acne,
2) for treating other types of disorders of keratinization, notably ichthyoses, ichthyosiform states, Darier disease, palmoplantar keratodermas, leukoplasias and leukoplasiform states, cutaneous or mucosal (buccal) lichen,
3) for treating other dermatological conditions and afflictions with an immuno-allergic inflammatory component, with or without a disorder of cellular proliferation, and notably all forms of psoriasis, whether cutaneous, mucosal or ungual, and even psoriatic rheumatism, or cutaneous atopy, such as eczema or respiratory atopy or gingival hypertrophy,
4) for treating all dermal or epidermal proliferations whether benign or malignant, whether or not they are of viral origin such as common warts, flat warts and epidermodysplasia verruciformis, oral or florid papillomatoses, T lymphoma, and proliferations that can be induced by ultraviolet radiation notably in the case of basal and prickle-cell epithelioma, as well as any precancerous skin lesion such as keratoacanthomas,
5) for treating other dermatological disorders such as immune dermatoses such as lupus erythematosus, bullous immune diseases and collagen diseases, such as scleroderma,
6) in the treatment of dermatological or general conditions and afflictions with an immunological component,
7) in the treatment of skin disorders due to exposure to UV radiation as well as for repairing or combating skin aging, whether photo-induced or chronological, or for reducing pigmentations and actinic keratoses, or all pathologies associated with chronological or actinic aging, such as xerosis,
8) for combating disorders of sebaceous function such as hyperseborrhoea of acne or seborrhea simplex,
9) for preventing or treating disorders of cicatrization, or for preventing or for repairing stretch marks,
10) in the treatment of disorders of pigmentation, such as hyperpigmentation, melasma, hypopigmentation or vitiligo,
11) in the treatment of disturbances of lipid metabolism, such as obesity, hyperlipidaemia, or non-insulin-dependent diabetes,
12) in the treatment of inflammatory disorders such as arthritis,
13) in the treatment or prevention of cancerous or precancerous states,
14) in the prevention or treatment of alopecia of various origins, notably alopecia due to chemotherapy or to radiation,
15) in the treatment of immune system disorders, such as asthma, type I diabetes mellitus, multiple sclerosis, or other selective dysfunctions of the immune system,
16) in the treatment of disorders of the cardiovascular system such as arteriosclerosis or hypertension.

The present invention also features a pharmaceutical or cosmetic compositions comprising, formulated into a physiologically acceptable medium, at least one compound of general formula (I) as defined above.

"Physiologically acceptable medium" means a medium compatible with the skin, the mucosae and the appendages.

The present invention also features formulation of the compounds of general formula (I) into medicinal products useful for the treatment of the aforementioned disorders, in particular for regulating and/or restoring the metabolism of skin lipids.

The compositions according to the invention can be administered by the oral, enteral, parenteral, topical or ocular route. Preferably, the pharmaceutical composition is packaged in a form suitable for topical application. Topical application means administration on the skin or the mucosae.

For the oral route, the composition, more particularly the pharmaceutical composition, can be in the form of tablets, capsules, coated pills, syrups, suspensions, solutions, powders, granules, emulsions, microspheres or nanospheres or lipid or polymeric vesicles permitting controlled release. For the parenteral route, the composition can be in the form of solutions or suspensions for infusion or for injection.

The compounds according to the invention are generally administered at a daily dose ranging from about 0.001 mg/kg to 100 mg/kg of body weight, in 1 to 3 divided doses.

The compounds are administered systemically at a concentration generally ranging from 0.001 and 10 wt. %, preferably from 0.01 and 1 wt. %, relative to the weight of the composition.

For topical administration, the pharmaceutical compositions according to the invention are more particularly useful for the treatment of the skin and of the mucosae and can be in the form of unguents, creams, milks, ointments, powders, moistened pads, solutions, gels, sprays, lotions or suspensions. Same can also be in the form of microspheres or nanospheres or lipid or polymeric vesicles or of polymeric patches and of hydrogels permitting controlled release. This composition for topical administration can be in anhydrous form, in aqueous form or in the form of an emulsion.

The compounds are applied topically at a concentration generally ranging from 0.001 to 10 wt. %, preferably from 0.01 to 1 wt. %, relative to the total weight of the composition.

The compounds of general formula (1) according to the invention also find application in the cosmetics field, in particular in body and hair hygiene and more particularly for regulating and/or restoring the metabolism of skin lipids.

The present invention therefore also features the cosmetic use of a compound of formula (I) or of a composition comprising, in a physiologically acceptable medium, at least one of the compounds of formula (I) for body or hair hygiene.

The cosmetic compositions according to the invention containing, in a cosmetically acceptable medium, at least one compound of general formula (I) or one of its optical or geometric isomers or one of its salts, can notably be in the form of a cream, a milk, a lotion, a gel, microspheres or nanospheres or lipid or polymeric vesicles, a soap or a shampoo.

The concentration of compound of general formula (I) in the cosmetic composition ranges from 0.001 to 3 wt. %, relative to the total weight of the composition.

The compositions as described above can of course additionally contain inert or even pharmacodynamically active additives or combinations of these additives, and notably: wetting agents; depigmenting agents such as hydroquinone, azelaic acid, caffeic acid or kojic acid; emollients; hydrating agents such as glycerol, PEG 400, thiamorpholinone, and derivatives thereof or also urea; antiseborrhoeic or antiacne agents, such as S-carboxymethylcysteine, S-benzyl-cysteamine, their salts or their derivatives, or benzoyl peroxide; antifungal agents such as ketoconazole or polymethylene-4,5-isothiazolidones-3; antibacterials, carotenoids and, notably, β-carotene; antipsoriatic agents such as anthraline and its derivatives; eicosa-5,8,11,14-tetraynoic and eicosa-5,8,11-triynoic acids, their esters and amides and finally retinoid. The compounds of general formula (I) can also be combined with the D vitamins or their derivatives, with corticosteroids, with anti-free-radical agents, α-hydroxy or α-keto acids or their derivatives, or with ion channel blockers.

These compositions can also contain agents for improving taste, preservatives such as esters of parahydroxybenzoic acid, stabilizers, moisture regulators, pH regulators, agents for modifying osmotic pressure, emulsifiers, UV-A and UV-B filters, antioxidants, such as α-tocopherol, butylhydroxyanisole or butylhydroxytoluene.

Of course, one skilled in the art will take care to select the optional compound or compounds to be added to these compositions in such a way that the advantageous properties intrinsically attached to the present invention are not or substantially are not impaired by the addition envisaged.

In order to further illustrate the present invention and the advantages thereof, the following specific examples are given, including results of biological activity, it being understood that same are intended only as illustrative and in nowise limitative. In said examples to follow, all parts and percentages are given by weight, unless otherwise indicated.

EXAMPLE 1

(Z)-3-(4-{2-[4-(butane-1-sulfonyloxy)-phenyl]-ethoxy}-3-methoxy-phenyl)-2-ethoxy-acrylic acid a—(diethoxy-phosphoryl)-ethoxy-ethyl acetate 18.5 g (112 mmol) of chloro-ethoxy-ethyl acetate and 19.2 ml (112 mmol) of triethylphosphite are put in a flask and heated at 150° C. for 5 hours. The progress of the reaction is monitored with NMR. 34 g (100%) of (diethoxy-phosphoryl)-ethoxy-ethyl acetate is obtained directly in the form of a colorless liquid.

b—3-methoxy-4-(4-methoxy-benzyloxy)-benzaldehyde 5 g (36.1 mmol) of potassium carbonate and then 4.9 ml (36.1 mmol) of 1-chloromethyl-4-methoxy-benzene are added to a solution of 5 g (33 mmol) of 4-hydroxy-3-methoxy-benzaldehyde in 100 ml of acetone. The reaction mixture is then stirred at 55° C. for 28 hours and then filtered. The filtrate is concentrated under vacuum. The residue obtained is taken up in heptane and filtered. 8.9 g (100%) of 3-methoxy-4-(4-methoxy-benzyloxy)-benzaldehyde is obtained in the form of a beige solid.

c—(Z)-2-ethoxy-3-[3-methoxy-4-(4-methoxy-benzyloxy)-phenyl]-ethyl acrylate 0.48 g (12 mmol) of 60% sodium hydride is added to a solution, previously cooled to 0° C., of 3.25 g (12 mmol) of (diethoxy-phosphoryl)-ethoxy-ethyl acetate in 35 ml of tetrahydrofuran. The reaction mixture is brought back to room temperature and stirred for 45 minutes, and then 3 g (11 mmol) of 3-methoxy-4-(4-methoxy-benzyloxy)-benzaldehyde in 40 ml of tetrahydrofuran is added. After stirring at room temperature for 15 hours, water and ethyl acetate are added and then the reaction mixture is extracted with ethyl acetate. The organic phase is washed with saturated sodium chloride solution, dried over magnesium sulfate, filtered, and evaporated. The residue is purified by silica column chromatography, eluted with a heptane/ethyl acetate mixture 80/20. 2.6 g (43%) of (Z)-2-ethoxy-3-[3-methoxy-4-(4-methoxy-benzyloxy)-phenyl]-ethyl acrylate is obtained.

d—(Z)-2-ethoxy-3-(4-hydroxy-3-methoxy-phenyl)-ethyl acrylate 1.7 ml (22 mmol) of trifluoroacetic acid is added to a solution of 1.7 g (4.4 mmol) of (Z)-2-ethoxy-3-[3-methoxy-4-(4-methoxy-benzyloxy)-phenyl]-ethyl acrylate in 15 ml of dichloromethane. The reaction mixture is stirred at room temperature for 2 hours. After adding water, and aqueous solution of sodium hydroxide 1M to pH 8-9, the reaction mixture is extracted with dichloromethane. The organic phases are combined, washed with water, dried over sodium sulfate, and then the solvents are evaporated under vacuum. The raw residue obtained is purified by silica column chromatography, eluted with a heptane/ethyl acetate mixture 80/20 to give 0.45 g (38%) of (Z)-2-ethoxy-3-(4-hydroxy-3-methoxy-phenyl)-ethyl acrylate.

e—[4-(2-methoxy-ethoxymethoxy)-phenyl]-methyl acetate 0.53 g (132 mmol) of 60% sodium hydride is added in portions to a solution at 0° C. of 20 g (120 mmol) of (4-hydroxy-phenyl)-methyl acetate diluted in 100 ml of tetrahydrofuran and 100 ml of dimethylformamide. The reaction mixture is stirred at room temperature, and then 15 ml (132 mmol) of 1-chloromethoxy-2-methoxy-ethane is added dropwise. After stirring at room temperature for 2 hours, then adding water, the reaction mixture is extracted with ethyl acetate. The organic phases are combined, washed with saturated sodium chloride solution and then dried over magnesium sulfate. After evaporation of the solvents, 25 g (86%) of [4-(2-methoxy-ethoxymethoxy)-phenyl]-methyl acetate is obtained in the form of a colorless oil.

f—2-[4-(2-methoxy-ethoxymethoxy)-phenyl]-ethanol 2.7 g (122.3 mmol) of lithium borohydride is added to a solution of 10 g (41 mmol) of [4-(2-methoxy-ethoxymethoxy)-phenyl]-methyl acetate in 100 ml of tetrahydrofuran. The reaction mixture is stirred at 60° C. for 4 h. After cooling, the reaction mixture is poured into a mixture of ice and saturated aqueous ammonium chloride solution, acidified with aqueous solution of acetic acid of concentration 1M and then extracted with ethyl acetate. The organic phases are combined, washed with saturated sodium chloride solution, and dried over magnesium sulfate. After evaporation of the solvents, 8.9 g (97%) of 2-[4-(2-methoxy-ethoxymethoxy)-phenyl]-ethanol is obtained in the form of a colorless oil.

g—(Z)-2-ethoxy-3-(3-methoxy-4-{2-[4-(2-methoxy-ethoxymethoxy)-phenyl]-ethoxy}-phenyl)-ethyl acrylate 0.45 g (1.70 mmol) of 2-[4-(2-methoxy-ethoxymethoxy)-phenyl]-ethanol, 0.42 g (1.87 mmol) of (Z)-2-ethoxy-3-(4-hydroxy-3-methoxy-phenyl)-ethyl acrylate and 0.67 g (2.55 mmol) of triphenylphosphine are put in 10 ml of tetrahydrofuran. Once completely dissolved, 0.40 ml (2.55 mmol) of diethylazodicarboxylate is added very slowly, then the reaction mixture is stirred at room temperature for 24 hours. After evaporation under vacuum, the raw residue is purified by silica column chromatography, eluted with a heptane/ethyl acetate mixture 70/30 to give 0.41 g (51%) of (Z)-2-ethoxy-3-(3-methoxy-4-{2-[4-(2-methoxy-ethoxymethoxy)-phenyl]-ethoxy}-phenyl)-ethyl acrylate in the form of a colorless oil.

h—(Z)-2-ethoxy-3-{4-[2-(4-hydroxy-phenyl)-ethoxy]-3-methoxy-phenyl}-ethyl acrylate 0.2 ml of sulfuric acid is added to a solution of 0.41 g (0.86 mmol) of (Z)-2-ethoxy-3-(3-methoxy-4-{2-[4-(2-methoxy-ethoxymethoxy)-phenyl]ethoxy}-phenyl)-ethyl acrylate in 5 ml of tetrahydrofuran and 5 ml of methanol. The reaction mixture is stirred at room temperature for 15 hours and then the solvents are evaporated under vacuum. After adding water and ethyl acetate, the reaction mixture is extracted with ethyl acetate. The organic phase is washed with water, dried over magnesium sulfate, filtered and concentrated under vacuum to give 0.31 g (94%) of (Z)-2-ethoxy-3-{4-[2-(4-hydroxy-phenyl)-ethoxy]-3-methoxy-phenyl}-ethyl acrylate in the form of a colorless oil.

i—(Z)-3-(4-{2-[4-(butane-1-sulfonyloxy)-phenyl]-ethoxy}-3-methoxy-phenyl)-2-ethoxy-ethyl acrylate 0.11 ml (0.88 mmol) of butanesulfonyl chloride is added to a solution of 0.31 g (0.80 mmol) of (Z)-2-ethoxy-3-{4-[2-(4-hydroxy-phenyl)-ethoxy]-3-methoxy-phenyl}-ethyl acrylate and 0.14 ml (0.96 mmol) of triethylamine in 7 ml of dichloromethane. The reaction mixture is stirred at room temperature for 15 h. After adding water, and extracting with dichloromethane, the organic phases are combined, washed with water and then dried over magnesium sulfate. After evaporation of the solvents, the raw residue obtained is purified by silica column chromatography, eluted with a heptane/ethyl acetate mixture 70/30 to give 0.25 g (62%) of (Z)-3-(4-{2-[4-(butane-1-sulfonyloxy)-phenyl]-ethoxy}-3-methoxy-phenyl)-2-ethoxy-ethyl acrylate in the form of a colorless oil.

j—(Z)-3-(4-{2-[4-(butane-1-sulfonyloxy)-phenyl]-ethoxy}-3-methoxy-phenyl)-2-ethoxy-acrylic acid 1.7 ml (1.7 mmol) of an aqueous solution of sodium hydroxide of concentration 1M is added to a solution of 0.25 g (0.49 mmol) of (Z)-3-(4-{2-[4-(butane-1-sulfonyloxy)-phenyl]-ethoxy}-3-methoxy-phenyl)-2-ethoxy-ethyl acrylate in 10 ml of tetrahydrofuran. The reaction mixture is stirred at 68° C. for 48 h. After cooling, the reaction mixture is treated by adding 3 ml of an aqueous solution of hydrochloric acid of concentration 1M plus 20 ml of water and then extracted with ethyl acetate. The organic phases are combined, washed with saturated sodium chloride solution, dried over magnesium sulfate, and filtered. After evaporation of the solvents, the product is recrystallized from a pentane/acetone mixture to obtain 0.15 g (65%) of (Z)-3-(4-{2-[4-(butane-1-sulfonyloxy)-phenyl]-ethoxy}-3-methoxy-phenyl)-2-ethoxy-acrylic acid in the form of a white solid with melting point of 94° C.

$^1$H NMR ($\delta$, $CDCl_3$): 1.00 (t, 3H, J=7.4 Hz); 1.43 (t, 3H, J=7.1 Hz); 1.51 (m, 2H); 1.98 (m, 2H); 3.20 (t, 2H, J=7.1 Hz); 3.26 (t, 2H, J=7.8 Hz); 3.92 (s, 3H); 4.06 (q, 2H, J=7.4 Hz); 4.27 (t, 2H, J=7.1 Hz); 6.86 (d, 1H, J=8.4 Hz); 7.13 (s, 1H); 7.23-7.28 (m, 3H); 7.36 (d, 1H, J=8.4 Hz); 7.62 (s, 1H).

EXAMPLE 2

(Z)-3-(4-{3-[4-(butane-1-sulfonyloxy)-3-methoxy-phenyl]-propyl}-3-butoxy-phenyl)-2-methoxy-acrylic acid a—3-hydroxy-4-iodobenzoic acid 21 g (520 mmol) of sodium hydroxide and then 79 g (520 mmol) of sodium iodide are added to a solution of 69 g (500 mmol) of 3-hydroxybenzoic acid in 700 ml of methanol. The reaction mixture is cooled to 0° C. and then Javel water (520 mmol) is added dropwise. The reaction mixture is stirred at 0-5° C. for 2 hours and then at room temperature for 15 h. After evaporating the methanol, the reaction mixture is acidified with a concentrated solution of hydrochloric acid. The precipitate is filtered, washed with water and dried. 41.9 g of 3-hydroxy-4-iodobenzoic acid is obtained in the form of a white solid with melting point of 218° C. The aqueous phase is extracted with ethyl acetate, the organic phase obtained is dried over magnesium sulfate, filtered, and evaporated. The residue obtained is taken up in heptane and the precipitate obtained is filtered.

Analysis showed that 61.3 g (56%) of 3-hydroxy-4-iodobenzoic acid is obtained.

b—methyl 3-hydroxy-4-iodobenzoate 6.1 g (35.6 mmol) of paratoluene sulfonic acid is added to a solution of 47 g (150 mmol) of 3-hydroxy-4-iodobenzoic acid in 300 ml of methanol. The reaction mixture is heated at 70° C. for 48 hours. After adding 1000 ml of water, the precipitate is filtered, and rinsed with water to neutral pH. 37.4 g (76%) of methyl 3-hydroxy-4-iodobenzoate is obtained in the form of a beige powder.

c—methyl 3-butoxy-4-iodobenzoate 14.7 ml (130 mmol) of iodobutane is added to a solution of 30 g (110 mmol) of methyl 3-hydroxy-4-iodobenzoate and 17.9 g (130 mmol) of potassium carbonate in 300 ml of 2-butanone. The reaction mixture is heated at 60° C. for 16 hours. After adding 100 ml of water and then extraction with ethyl acetate, the organic phases are combined, dried over sodium sulfate, and filtered. The solvents are evaporated and then the residue is taken up in heptane and filtered. 18.2 g of methyl 3-butoxy-4-iodobenzoate is obtained in the form of white crystals. The filtrate is concentrated and the residue is purified by silica column chromatography, eluted with a heptane/ethyl acetate mixture 8/2, obtaining 11.6 g of methyl 3-butoxy-4-iodobenzoate. 29.8 g (82%) of methyl 3-butoxy-4-iodobenzoate is thus obtained.

d—4-allyl-2-methoxy-phenyl 1-butane sulfonate 13 ml (100 mmol) of butanesulfonyl chloride is added dropwise to a solution of 15 g (90 mmol) of eugenol and 16 ml (110 mmol) of triethylamine in 150 ml of dichloromethane previously cooled to −20° C., then the reaction mixture is stirred for 4 hours at room temperature. After adding 50 ml of water and extracting with dichloromethane, the organic phase is dried over sodium sulfate, filtered and evaporated. The raw residue is purified by silica column chromatography, eluted with a heptane/ethyl acetate mixture 90/10. 24.3 g (74%) of 4-allyl-2-methoxy-phenyl 1-butane sulfonate is obtained in the form of a yellow oil.

e—4-{(E)-3-[4-(butane-1-sulfonyloxy)-3-methoxy-phenyl]-propenyl}-3-butoxy-methyl benzoate 42 mg (0.12 mmol) of 2-(dicyclohexylphosphino)biphenyl, 13 mg (0.06 mmol) of palladium acetate and then 0.63 ml (4.5 mmol) of triethylamine are added to a solution of 1 g (3 mmol) of 3-butoxy-4-iodomethyl benzoate and 0.85 g (3 mmol) of 4-allyl-2-methoxy-phenyl 1-butane sulfonate in 10 ml of dimethylformamide. The reaction mixture is heated at 90° C. for 15 hours. After adding 20 ml of water and then extracting with ethyl acetate, the organic phases are combined, washed with saturated sodium chloride solution and dried over sodium sulfate, filtered, and evaporated. The raw residue obtained is purified by silica column chromatography, eluted with a heptane/ethyl acetate mixture 80/20. 1.2 g (81%) of 4-{(E)-3-[4-(butane-1-sulfonyloxy)-3-methoxy-phenyl]-propenyl}-3-butoxy-methyl benzoate is obtained in the form of a yellow oil.

f—4-{3-[4-(butane-1-sulfonyloxy)-3-methoxy-phenyl]-propyl}-3-butoxy-methyl benzoate 0.7 g of 10% palladium on charcoal is added to a solution of 7 g (14.3 mmol) of 4-{(E)-3-(butane-1-sulfonyloxy)-3-methoxy-phenyl]-propenyl}-3-butoxy-methyl benzoate in 250 ml of methanol. The reaction mixture is placed under atmospheric pressure of hydrogen and stirred for 12 hours at room temperature. The reaction mixture is filtered on Celite, and rinsed with dichloromethane, then the solvents are evaporated and the residue is purified by silica column chromatography, eluted with a heptane/ethyl acetate mixture 90/10. 5.21 g (75%) of 4-{3-[4-(butane-1-sulfonyloxy)-3-methoxy-phenyl]-propyl}-3-butoxy-methyl benzoate is obtained in the form of a colorless oil.

g—4-[3-(2-butoxy-4-hydroxymethyl-phenyl)-propyl]-2-methoxy-phenyl 1-butane sulfonate 0.69 (32 mmol) of lithium borohydride is added to a solution of 5.2 g (11 mmol) of 4-{3-[4-(butane-1-sulfonyloxy)-3-methoxy-phenyl]-propyl}-3-butoxy-methyl benzoate in 50 ml of tetrahydrofuran. The reaction mixture is heated at 60° C. for 15 hours and then hydrolyzed gently in an iced saturated solution of ammonium chloride. The reaction mixture is neutralized with concentrated hydrochloric acid and then extracted with ethyl acetate. The organic phases are washed with water, dried over sodium sulfate, filtered, and evaporated. The residue is purified by silica column chromatography, eluted with a heptane/ethyl acetate mixture 70/30.

4.21 g (86%) of 4-[3-(2-butoxy-4-hydroxymethyl-phenyl)-propyl]-2-methoxy-phenyl 1-butane sulfonate is obtained in the form of a colorless oil h—4-[3-(2-butoxy-4-formyl-phenyl)-propyl]-2-methoxy-phenyl 1-butane sulfonate 7.9 g (9.1 mmol) of manganese oxide is added to a solution of 4.2 g (9.1 mmol) of 4-[3-(2-butoxy-4-hydroxymethyl-phenyl)-propyl]-2-methoxy-phenyl 1-butane sulfonate in 300 ml of dichloromethane. The reaction mixture is stirred for 15 hours at room temperature. The reaction mixture is filtered on Celite, and rinsed with dichloromethane. The solvents are evaporated. 3.95 g (94%) of 4-[3-(2-butoxy-4-formyl-phenyl)-propyl]-2-methoxy-phenyl 1-butane sulfonate is obtained in the form of a yellow oil.

i—methoxy-methoxycarbonyl-methyl triphenyl-phosphonium chloride 25 g (186 mmol) of methyl dimethoxyacetate is added to 27 ml (215 mmol) of acetyl chloride at room temperature. 0.1 g (0.2% molar) of iodine is added and then the reaction mixture is stirred at 55° C. for 16 hours. The excess of acetyl chloride is evaporated under vacuum, then the residue is dissolved in 100 ml of dichloromethane. 49 g (204 mmol) of triphenylphosphine is added and then the reaction mixture is stirred at 37° C. for 3 hours. The solvents are evaporated and the residue is crystallized in diisopropyl ether. 70 g (88%) of (methoxy-methoxycarbonyl-methyl)-triphenyl-phosphonium chloride is obtained.

j—(Z)-3-(4-{3-[4-(butane-1-sulfonyloxy)-3-methoxy-phenyl]-propyl}-3-butoxy-phenyl)-2-methoxy-methyl acrylate 1.3 g (4 mmol) of methoxy-methoxycarbonyl-methyl triphenyl-phosphonium chloride and 0.45 ml (3.24 mmol) of triethylamine are added to a solution of 1 g (2.16 mmol) of 4-[3-(2-butoxy-4-formyl-phenyl)-propyl]-2-methoxy-phenyl 1-butane sulfonate in 10 ml of tetrahydrofuran. The reaction mixture is heated at 60° C. for 6 hours. After adding 20 ml of water and then extracting with ethyl acetate, the organic phases are combined, dried over sodium sulfate, filtered and evaporated. The residue obtained is purified by silica column chromatography, eluted with a heptane/ethyl acetate mixture 80/20.

0.78 g (62%) of (Z)-3-(4-{3-[4-(butane-1-sulfonyloxy)-3-methoxy-phenyl]-propyl}-3-butoxy-phenyl)-2-methoxy-methyl acrylate is obtained in the form of a yellow solid.

k—(Z)-3-(4-{3-[4-(butane-1-sulfonyloxy)-3-methoxy-phenyl]-propyl}-3-butoxy-phenyl)-2-methoxy-acrylic acid 2.6 ml (2.6 mmol) of an aqueous solution of lithium hydroxide of concentration 1M is added to a solution of 0.72 g (1.3 mmol) of (Z)-3-[4-{3-[4-(butane-1-sulfonyloxy)-3-methoxy-phenyl]-propyl}-3-buthoxy-phenyl)-2-methoxy-methyl acrylate in 7 ml of tetrahydrofuran. The reaction mixture is stirred for 12 hours at room temperature. The reaction mixture is treated by adding 20 ml of water and acidifying with an aqueous solution of hydrochloric acid 1M then extraction with ethyl acetate. The organic phases are combined, dried over sodium sulfate, filtered, and evaporated. The residue obtained is purified by silica column chromatography, eluted with a dichloromethane/ethyl acetate mixture 80/20. After evaporation of the solvents, the product obtained is crystallized from heptane and filtered. 232.5 mg (33%) of (Z)-3-(4-{3-[4-(butane-1-sulfonyloxy)-3-methoxy-phenyl]-propyl}-3-butoxy-phenyl)-2-methoxy-acrylic acid is obtained in the form of a white powder with melting point of 72.5° C.

$^1$H NMR (δ, CDCl$_3$): 0.99 (t, 3H, J=7.4 Hz); 1.01 (t, 3H, J=7.1 Hz); 1.49-1.56 (m, 4H); 1.81 (m, 2H); 1.94-1.99 (m, 4H); 2.65-2.73 (m, 4H); 3.28-3.32 (m, 2H); 3.79 (s, 3H); 3.9 (s, 3H); 4.01 (t, 2H, J=6.4 Hz); 6.80 (m, 2H); 7.14 (s, 1H); 7.15 (m, 1H); 7.20-7.27 (m, 2H); 7.38 (d, 1H, J=1.2 Hz).

EXAMPLE 3

(Z)-3-(4-{3-[4-(butane-1-sulfonyloxy)-3-methoxy-phenyl]-propyl}-3-butoxy-phenyl)-2-ethoxy-acrylic acid a—(ethoxy-ethoxycarbonyl-methyl)-triphenyl-phosphonium chloride 2.0 g (7.6 mmol) of triphenylphosphine is dissolved in 5 ml of chloroform and then 1.3 g (7.6 mmol) of 2-ethoxy-2-chloro-ethyl acetate is added. The mixture is stirred at 80° C. for 3 hours and then concentrated under vacuum. The residue obtained is crystallized with a mixture of diethyl ether and pentane. 2 g (61%) of (ethoxy-ethoxycarbonyl-methyl)-triphenyl-phosphonium chloride is obtained in the form of a white solid.

b—(Z)-3-(4-{3-[4-(butane-1-sulfonyloxy)-3-methoxy-phenyl]-propyl}-3-butoxy-phenyl)-2-ethoxy-ethyl acrylate 1.39 g (3.2 mmol) of (ethoxy-ethoxycarbonyl-methyl)-triphenyl-phosphonium chloride and 0.45 ml (3.24 mmol) of triethylamine are added to a solution of 1 g (2.2 mmol) of 4-[3-(2-butoxy-4-formyl-phenyl)-propyl]-2-methoxy-phenyl 1-butane sulfonate (prepared as described in Example 2h) in 10 ml of tetrahydrofuran. The reaction mixture is stirred at 60° C. for 4 hours. After adding 20 ml of water and then extracting with ethyl acetate, the organic phases are combined, dried over sodium sulfate, filtered and evaporated. The residue obtained is purified by silica column chromatography, eluted with a heptane/ethyl acetate mixture 80/20.

738 mg (59%) of (Z)-3-(4-{3-[4-(butane-1-sulfonyloxy)-3-methoxy-phenyl]-propyl}-3-butoxy-phenyl)-2-ethoxy-ethyl acrylate is obtained in the form of a colorless oil.

c—(Z)-3-(4-{3-[4-(butane-1-sulfonyloxy)-3-methoxy-phenyl]-propyl}-3-butoxy-phenyl)-2-ethoxy-acrylic acid 2.6 ml (2.6 mmol) of an aqueous solution of lithium hydroxide of concentration 1M is added to a solution of 0.74 g (1.3 mmol) of (Z)-3-(4-{3-[4-(butane-1-sulfonyloxy)-3-methoxy-phenyl]-propyl}-3-butoxy-phenyl)-2-ethoxy-ethyl acrylate in 7 ml of tetrahydrofuran. The reaction mixture is stirred for 12 hours at room temperature. After adding 20 ml of water and acidifying with an aqueous solution of hydrochloric acid of concentration 1M, the reaction mixture is extracted with ethyl acetate. The organic phases are combined, dried over sodium sulfate, filtered, and evaporated. The residue is purified by silica column chromatography, eluted with a mixture dichloromethane/ethyl acetate 80/20. After evaporation of the solvents, the product obtained is crystallized from heptane.

308 mg (43%) of (Z)-3-(4-{3-[4-(butane-1-sulfonyloxy)-3-methoxy-phenyl]-propyl}-3-butoxy-phenyl)-2-ethoxy-acrylic acid is obtained in the form of a white powder with melting point of 75° C.

$^1$H NMR (δ, CDCl$_3$): 0.90 (t, 3H, J=7.4 Hz); 0.92 (t, 3H, J=7.1 Hz); 1.31 (t, 3H, J=7.1 Hz); 1.43 (m, 4H); 1.73 (m, 2H); 1.85-1.91 (m, 4H); 2.56-2.63 (m, 4H); 3.19-3.22 (m, 2H); 3.79 (s, 3H); 3.91 (t, 2H, J=6.4 Hz); 3.96 (q, 2H, J=7.1 Hz); 6.72 (m, 2H); 7.04-7.19 (m, 4H); 7.39 (s, 1H).

EXAMPLE 4

(E)-3-(4-{3-[4-(butane-1-sulfonyloxy)-3-methoxy-phenyl]-propyl}-3-butoxy-phenyl)-2-methyl-acrylic acid a—4-[3-(2-butoxy-4-hydroxymethyl-phenyl)-propyl]-2-methoxy-phenyl 1-butane sulfonate 0.7 (32 mmol) of lithium borohydride is added to a solution of 5.2 g (11 mmol) of 4-{3-[4-(butane-1-sulfonyloxy)-3-methoxy-phenyl]-propyl}-3-butoxy-methyl benzoate (prepared according to Example 2f) in 50 ml of tetrahydrofuran. The reaction mixture is heated at 60° C. for 15 hours and then hydrolyzed gently in an iced saturated solution of ammonium chloride. The reaction mixture is neutralized with concentrated hydrochloric acid and then extracted with ethyl acetate. The organic phases are washed with water and dried over sodium sulfate. The solvents are evaporated and the residue is purified by silica column chromatography, eluted with a heptane/ethyl acetate mixture 70/30.

4.2 g (86%) of 4-[3-(2-butoxy-4-hydroxymethyl-phenyl)-propyl]-2-methoxy-phenyl 1-butane sulfonate is obtained in the form of a colorless oil.

b—4-[3-(2-butoxy-4-formyl-phenyl)-propyl]-2-methoxy-phenyl 1-butane sulfonate 7.9 g (91 mmol) of manganese oxide is added to a solution of 4.2 g (9.1 mmol) of 4-[3-(2-butoxy-4-hydroxymethyl-phenyl)-propyl]-2-methoxy-phenyl 1-butane sulfonate in 300 ml of dichloromethane. The reaction mixture is stirred for 15 hours at room temperature and then filtered on Celite. The solvents are evaporated. 3.9 g (94%) of 4-[3-(2-butoxy-4-formyl-phenyl)-propyl]-2-methoxy-phenyl 1-butane sulfonate is obtained in the form of a yellow oil.

c—(Z)-3-(4-{3-[4-(butane-1-sulfonyloxy)-3-methoxy-phenyl]-propyl}-3-butoxy-phenyl)-2-methyl-methyl acrylate 1.3 g (40 mmol) of 1-methoxycarbonyl-ethyl-triphenyl phosphonium chloride and 0.45 ml (3.2 mmol) of triethylamine are added to a solution of 1 g (2.2 mmol) of 4-[3-(2-butoxy-4-formyl-phenyl)-propyl]-2-methoxy-phenyl 1-butane sulfonate in 10 ml of tetrahydrofuran. The reaction mixture is stirred at 60° C. for 6 hours. The reaction mixture is treated by adding 20 ml of water and then extracted with ethyl acetate. The organic phases are combined, and dried over sodium sulfate. The solvents are evaporated and then the residue is purified by silica column chromatography, eluted with a heptane/ethyl acetate mixture 80/20. 0.8 g (62%) of (Z)-3-(4-{3-[4-(butane-1-sulfonyloxy)-3-methoxy-phenyl]- propyl}-3-butoxy-phenyl)-2-methyl-methyl acrylate is obtained in the form of a yellow solid.

d—(E)-3-(4-{3-[4-(butane-1-sulfonyloxy)-3-methoxy-phenyl]-propyl}-3-butoxy-phenyl)-2-methyl-acrylic acid 3.5 ml (3.4 mmol) of an aqueous solution of lithium hydroxide of concentration 1M is added to a solution of 923 mg (1.7 mmol) of (E)-3-(4-{3-[4-(butane-1-sulfonyloxy)-3-methoxy-phenyl]-propyl}-3-butoxy-phenyl)-2-methyl-methyl acrylate in 10 ml of tetrahydrofuran. The reaction mixture is stirred for 12 hours at room temperature. After adding 20 ml of water and acidifying with an aqueous solution of hydrochloric acid 1M, the reaction mixture is extracted with ethyl acetate. The organic phases are combined, dried over sodium sulfate, filtered and evaporated. After evaporation of the solvents, the residue is purified by silica column chromatography, eluted with a mixture of dichloromethane/methanol 80/20. 261 mg (30%) of (Z)-3-(4-{3-[4-(butane-1-sulfonyloxy)-3-methoxy-phenyl]-propyl}-3-butoxy-phenyl)-2-methyl-acrylic acid is obtained in the form of a yellow oil.

$^1$H NMR (δ, CDCl$_3$): 0.89 (t, 3H, J=7.4 Hz); 0.92 (t, 3H, J=7.1 Hz); 1.19 (m, 4H); 1.72 (m, 2H); 1.88 (m, 2H); 2.09 (s, 3H); 2.59 (m, 4H); 3.20 (m, 2H); 3.79 (s, 3H); 3.90 (t, 2H, J=6.3 Hz); 6.70 (m, 2H); 6.73 (s, 1H); 6.91 (d, 1H, J=7.7 Hz); 7.07-7.19 (m, 2H); 7.71 (s, 1H).

EXAMPLE 5

(Z)-3-{3-butoxy-4-[2-(4-methanesulfonyloxy-phenyl)-ethoxy]-phenyl}-2-ethoxy-acrylic acid a—3-butoxy-4-hydroxy-benzaldehyde 4.3 g (188 mmol) of sodium is put at the bottom of a flask under nitrogen and 40 ml of 1-butanol is poured on top. The reaction mixture is stirred and heated progressively up to 120° C.; as the butanolate formed is sparingly soluble, 20 ml of 1-butanol is added. When all the sodium has been consumed, the reaction mixture is brought back to room temperature and 40 ml of dimethylformamide is added. Under nitrogen, 6.8 g (68.2 mmol) of copper(I) chloride is added and then 12.4 g (62 mmol) of 3-bromo-4-hydroxy-benzaldehyde. The reaction mixture is heated progressively to 120° C. and stirred for 2 hours. After cooling to room temperature and then acidifying to pH5 with aqueous hydrochloric acid of concentration 2M, the reaction mixture is extracted with ethyl acetate. The organic phases are combined, washed with saturated sodium chloride solution, dried over magnesium sulfate, filtered, and evaporated. After trituration and then recrystallization of the residue from pentane, 9.7 g (81%) of 3-butoxy-4-hydroxy-benzaldehyde is obtained.

b—(Z)-3-(3-butoxy-4-hydroxy-phenyl)-2-ethoxy-ethyl acrylate 9.7 g (50 mmol) of 3-butoxy-4-hydroxy-benzaldehyde is put in 250 ml of tetrahydrofuran and then 32.1 g (75 mmol) of (ethoxy-ethoxycarbonyl-methyl)-triphenyl-phosphonium chloride (prepared according to Example 3a) and 15 ml (100 mmol) of triethylamine are added. The reaction mixture is stirred at 40° C. for 6 hours and then filtered and the filtrate is evaporated to dryness. The raw product obtained is taken up in ethyl ether and then filtered to remove the excess phosphonium. The filtrate is again concentrated under vacuum and then purified by silica column chromatography, eluted with a heptane/ethyl acetate mixture 80/20 to give 16.2 g (100%) of (Z)-3-(3-butoxy-4-hydroxy-phenyl)-2-ethoxy-ethyl acrylate in the form of a caramel-colored oil.

c—(Z)-3-(3-butoxy-4-{2-[4-(2-methoxy-ethoxymethoxy)-phenyl]-ethoxy}-phenyl)-2-ethoxy-methyl acrylate 2.2 g (9.7 mmol) of 2-[4-(2-methoxy-ethoxymethoxy)-phenyl]-ethanol (prepared according to Example 1c), 2.0 g (6.5 mmol) of (Z)-3-(3-butoxy-4-hydroxy-phenyl)-2-ethoxy-ethyl acrylate and 2.5 g (9.7 mmol) of triphenylphosphine are put in 45 ml of tetrahydrofuran. Once completely dissolved, 1.5 ml (9.7 mmol) of diethylazodicarboxylate is poured very slowly into the reaction mixture. The reaction mixture is stirred for 2 h at room temperature. The solvents are evaporated under vacuum and the raw product is purified by silica column chromatography, eluted with a heptane/ethyl acetate mixture 70/30 to give 2.7 g (82%) of (Z)-3-(3-butoxy-4-{2-[4-(2-methoxy-ethoxymethoxy)-phenyl]-ethoxy}-phenyl)-2-ethoxy-methyl acrylate in the form of a colorless oil.

d—(Z)-3-{3-butoxy-4-[2-(4-hydroxy-phenyl)-ethoxy]-phenyl}-2-ethoxy-ethyl acrylate 0.5 ml of sulfuric acid is added to a solution of 2.7 g (5.2 mmol) of (Z)-3-(3-butoxy-4-{2-[4-(2-methoxy-ethoxymethoxy)-phenyl]-ethoxy}-phenyl)-2-ethoxy-ethyl acrylate in 20 ml of tetrahydrofuran and 20 ml of methanol. The reaction mixture is stirred at room temperature for 15 h and then the solvents are evaporated under vacuum. The residue is taken up in water and ethyl acetate and then extracted with ethyl acetate. After separation of the phases, the organic phase is washed with water, dried over magnesium sulfate, filtered and concentrated under vacuum to give 2.2 g (100%) of (Z)-3-{3-butoxy-4-[2-(4-hydroxy-phenyl)-ethoxy]-phenyl}-2-ethoxy-ethyl acrylate in the form of a light yellow oil, which crystallizes.

e—(Z)-3-{3-butoxy-4-[2-(4-methanesulfonyloxy-phenyl)-ethoxy]-phenyl}-2-ethoxy-ethyl acrylate 0.16 ml (2.1 mmol) of methanesulfonyl chloride is added to a solution of 0.6 g (1.4 mmol) of (Z)-3-{3-butoxy-4-[2-(4-hydroxy-phenyl)-ethoxy]-phenyl}-2-ethoxy-ethyl acrylate and 0.24 ml (1.7 mmol) of triethylamine in 10 ml of dichloromethane. The reaction mixture is stirred at room temperature for 15 hours. After adding 10 ml of water and extracting with dichloromethane, the organic phases are combined, washed with water, dried over magnesium sulfate and filtered. The solvents are evaporated. The raw product obtained is purified by silica column chromatography, eluted with a heptane/ethyl acetate mixture 70/30 to give 0.48 g (68%) of (Z)-3-{3-butoxy-4-[2-(4-methanesulfonyloxy-phenyl)-ethoxy]-phenyl}-2-ethoxy-ethyl acrylate in the form of a white solid.

f—(Z)-3-{3-butoxy-4-[2-(4-methanesulfonyloxy-phenyl)-ethoxy]-phenyl}-2-ethoxy acrylic acid 0.11 g (2.8 mmol) of solid sodium hydroxide and 2 ml of water are added to a solution of 0.48 g (0.95 mmol) of (Z)-3-{3-butoxy-4-[2-(4-methanesulfonyloxy-phenyl)-ethoxy]-phenyl}-2-ethoxy-ethyl acrylate in 10 ml of tetrahydrofuran. The reaction mixture is stirred at 68° C. for 24 hours. After cooling, the reaction mixture is treated by adding an aqueous solution of hydrochloric acid of concentration 1M plus 20 ml of water and then extracted with ethyl acetate. The organic phases are combined, washed with saturated sodium chloride solution, dried over magnesium sulfate, filtered, and evaporated. The product is recrystallized from a pentane/acetone mixture to obtain 0.15 g (33%) of (Z)-3-{3-butoxy-4-[2-(4-methanesulfonyloxy-phenyl)-ethoxy]-phenyl}-2-ethoxy acrylic acid in the form of a white solid with melting point of 117° C.

$^1$H NMR (δ, CDCl$_3$): 1.02 (t, 3H, J=7.4 Hz); 1.41 (t, 3H, J=7.1 Hz); 1.54 (m, 2H); 1.85 (m, 2H); 3.15 (s, 3H); 3.17 (m, 2H); 4.01-4.06 (m, 4H); 4.25 (t, 2H, J=6.7 Hz); 6.85 (d, 1H, J=8.4 Hz); 7.11 (s, 1H); 7.23-7.28 (m, 3H); 7.41 (d, 1H, J=8.5 Hz); 7.58 (s, 1H).

EXAMPLE 6

(Z)-3-(4-{2-[4-(butane-1-sulfonyloxy)-phenyl]-ethoxy}-3-butoxy-phenyl)-2-ethoxy-acrylic acid a—(Z)-3-{3-butoxy-4-[2-(4-butanesulfonyloxy-phenyl)-ethoxy]-phenyl}-2-ethoxy-ethyl acrylate 0.2 ml (1.5 mmol) of butanesulfonyl chloride is added to a solution of 0.6 g (1.4 mmol) of (Z)-3-{3-butoxy-4-[2-(4-hydroxy-phenyl)-ethoxy]-phenyl}-2-ethoxy-ethyl acrylate (prepared according to Example 5d) and 0.24 ml (1.7 mmol) of triethylamine in 10 ml of dichloromethane. The reaction mixture is stirred at room temperature for 15 hours. After adding 10 ml of water and then extracting with dichloromethane, the organic phases are combined, washed with water, dried over magnesium sulfate, filtered and evaporated. The raw product obtained is purified by silica column chromatography, eluted with a heptane/ethyl acetate mixture 80/20 to give 0.46 g (68%) of (Z)-3-{3-butoxy-4-[2-(4-butanesulfonyloxy-phenyl)-ethoxy]-phenyl}-2-ethoxy-ethyl acrylate in the form of an orange-colored oil.

b—(Z)-3-{3-butoxy-4-[2-(4-butanesulfonyloxy-phenyl)-ethoxy]-phenyl}-2-ethoxy acrylic acid 0.10 g (2.5 mmol) of solid sodium hydroxide and 2 ml of water are added to a solution of 0.46 g (0.84 mmol) of (Z)-3-{3-butoxy-4-[2-(4-butanesulfonyloxy-phenyl)-ethoxy]-phenyl}-2-ethoxy-ethyl acrylate in 10 ml of tetrahydrofuran. The reaction mixture is stirred at 68° C. for 24 hours. After cooling, the reaction mixture is treated by adding an aqueous solution of hydrochloric acid of concentration 1M plus 20 ml of water and then extracted with ethyl acetate. The organic phases are combined, washed with saturated sodium chloride solution, dried over magnesium sulfate, filtered, and evaporated. The product obtained is recrystallized from a pentane/acetone mixture to obtain 0.15 g (35%) of (Z)-3-{3-butoxy-4-[2-(4-butanesulfonyloxy-phenyl)-ethoxy]-phenyl}-2-ethoxy acrylic acid in the form of a white solid with melting point of 96° C.

$^1$H NMR (δ, CDCl$_3$): 0.91 (t, 3H, J=7.4 Hz); 0.94 (t, 3H, J=7.1 Hz); 1.34 (t, 3H, J=7.1 Hz); 1.43-1.48 (m, 4H); 1.77 (m, 2H); 1.89 (m, 2H); 3.08 (t, 2H, J=6.6 Hz); 3.16 (m, 2H); 3.93-3.97 (m, 4H); 4.16 (t, 2H, J=6.6 Hz); 6.76 (d, 1H, J=8.4 Hz); 7.12 (s, 1H); 7.13-7.19 (m, 3H); 7.30 (d, 1H, J=8.5 Hz); 7.49 (s, 1H).

EXAMPLE 7

(Z)-3-{3-butoxy-4-[2-(4-methanesulfonyloxy-3-methoxy-phenyl)-ethoxy]-phenyl}-2-ethoxy-acrylic acid a—[3-methoxy-4-(2-methoxy-ethoxymethoxy)-phenyl]-ethyl acetate 0.9 g (23 mmol) of 60% sodium hydride is added in portions to a previously cooled solution of 4 g (19 mmol) of (4-hydroxy-3-methoxy-phenyl)-ethyl acetate in 20 ml of tetrahydrofuran and 20 ml of dimethylformamide. After stirring at room temperature for 45 minutes, 2.4 ml (21 mmol) of 1-chloromethoxy-2-methoxy-ethane is added dropwise. After stirring at room temperature for 1 hour, water and ethyl acetate are added. The organic phase is washed with saturated sodium chloride solution, dried over magnesium sulfate, filtered, and evaporated. 5.5 g (97%) of [3-methoxy-4-(2-methoxy-ethoxymethoxy)-phenyl]-ethyl acetate is obtained.

b—2-[3-methoxy-4-(2-methoxy-ethoxymethoxy)-phenyl]-ethanol 1.2 g (57.1 mmol) of lithium borohydride is added in portions to a solution of 5.4 g (19.0 mmol) of [3-methoxy-4-(2-methoxy-ethoxymethoxy)-phenyl]-ethyl acetate diluted in 60 ml of tetrahydrofuran. After stirring at 60° C. for 2 hours and then at room temperature for 15 hours, the reaction mixture is poured into 100 ml of a saturated aqueous solution of ammonium chloride cooled to 0° C. and then extracted with ethyl acetate. The organic phases are combined, washed with saturated sodium chloride solution, dried over magnesium sulfate, filtered, and evaporated. The raw product obtained is purified by silica column chromatography, eluted with a heptane/ethyl acetate mixture 50/50 to give 3.55 g (74%) of 2-[3-methoxy-4-(2-methoxy-ethoxymethoxy)-phenyl]-ethanol in the form of a colorless oil.

c—(Z)-3-(3-butoxy-4-{2-[3-methoxy-4-(2-methoxy-ethoxymethoxy)-phenyl]-ethoxy}-phenyl)-2-ethoxy-ethyl acrylate 2.5 g (9.7 mmol) of 2-[3-methoxy-4-(2-methoxy-ethoxymethoxy)-phenyl]-ethanol, 2.0 g (6.5 mmol) of (Z)-3-(3-butoxy-4-hydroxy-phenyl)-2-ethoxy-ethyl acrylate and 3.4 g (13 mmol) of triphenylphosphine are put in 50 ml of tetrahydrofuran. Once completely dissolved, 2.1 ml (13 mmol) of diethylazodicarboxylate is poured very slowly into the reaction mixture. The reaction mixture is stirred for 15 hours at room temperature. The solvents are evaporated under vacuum and the raw product is purified by silica gel chromatography eluted with a heptane/ethyl acetate mixture 70/30 to give 2.3 g (66%) of (Z)-3-(3-butoxy-4-{2-[3-methoxy-4-(2-methoxy-ethoxymethoxy)-phenyl]-ethoxy}-phenyl)-2-ethoxy-ethyl acrylate in the form of a colorless oil.

d—(Z)-3-{3-butoxy-4-[2-(4-hydroxy-3-methoxy-phenyl)-ethoxy]-phenyl}-2-ethoxy-ethyl acrylate 0.5 ml of sulfuric acid is added to a solution of 2.3 g (4.2 mmol) of (Z)-3-(3-butoxy-4-{2-[3-methoxy-4-(2-methoxy-ethoxymethoxy)-phenyl]-ethoxy}-phenyl)-2-ethoxy-ethyl acrylate in 20 ml of tetrahydrofuran and 20 ml of methanol. The reaction mixture is stirred at room temperature for 15 hours. The solvents are evaporated under vacuum and extraction with ethyl acetate/water is carried out. After separation of the phases, the organic phase is washed with water, dried over magnesium sulfate, filtered and concentrated under vacuum to give 1.9 g (100%) of (Z)-3-{3-butoxy-4-[2-(4-hydroxy-3-methoxy-phenyl)-ethoxy]-phenyl}-2-ethoxy-ethyl acrylate in the form of an orange-colored oil, which crystallizes.

e—(Z)-3-{3-butoxy-4-[2-(4-methanesulfonyloxy-3-methoxy-phenyl)-ethoxy]-phenyl}-2-ethoxy-ethyl acrylate 0.24 ml (3.1 mmol) of methanesulfonyl chloride is added to a solution of 0.95 g (2.1 mmol) of (Z)-3-{3-butoxy-4-[2-(4-hydroxy-3-methoxy-phenyl)-ethoxy]-phenyl}-2-ethoxy-ethyl acrylate and 0.34 ml (2.50 mmol) of triethylamine in 10 ml of dichloromethane. The reaction mixture is stirred at room temperature for 15 hours and then the solvents are evaporated. The raw product obtained is purified by silica column chromatography, eluted with a heptane/ethyl acetate mixture 70/30 to give 0.89 g (80%) of (Z)-3-{3-butoxy-4-[2-(4-methanesulfonyloxy-3-methoxy-phenyl)-ethoxy]-phenyl}-2-ethoxy-ethyl acrylate in the form of a pale yellow oil.

f—(Z)-3-{3-butoxy-4-[2-(4-methanesulfonyloxy-3-methoxy-phenyl)-ethoxy]-phenyl}-2-ethoxy-acrylic acid 8.5 ml (8.5 mmol) of an aqueous solution of sodium hydroxide of concentration 1M is added to a solution of 0.9 g (1.7 mmol) of (Z)-3-{3-butoxy-4-[2-(4-methanesulfonyloxy-3-methoxy-phenyl)-ethoxy]-phenyl}-2-ethoxy-ethyl acrylate in 15 ml of tetrahydrofuran. The reaction mixture is stirred at 68° C. for 30 hours. After cooling, the reaction mixture is treated by adding an aqueous solution of hydrochloric acid of concentration 1M plus 20 ml of water and then extracted with ethyl acetate. The organic phases are combined, washed with saturated sodium chloride solution, dried over magnesium sulfate, filtered, and evaporated. The product is recrystallized from a heptane/ethyl acetate mixture to obtain 0.55 g (65%) of (Z)-3-{3-butoxy-4-[2-(4-methanesulfonyloxy-3-methoxy-phenyl)-ethoxy]-phenyl}-2-ethoxy-acrylic acid in the form of a white solid with melting point of 97° C.

$^1$H NMR (δ, CDCl$_3$): 1.01 (t, 3H, 7.4 Hz); 1.42 (t, 3H, J=7.1 Hz); 1.53 (m, 2H); 1.84 (m, 2H); 3.15 (t, 2H, J=6.6 Hz); 3.19 (s, 3H); 3.91 (s, 3H); 4.05 (m, 2H); 4.26 (t, 2H, J=6.7 Hz); 6.85 (d, 1H, J=8.4 Hz); 6.96 (m, 1H); 6.99 (s, 1H); 7.12 (s, 1H); 7.24-7.28 (m, 2H); 7.59 (s, 1H).

EXAMPLE 8

(Z)-3-(4-{2-[4-(butane-1-sulfonyloxy)-3-methoxy-phenyl]-ethoxy}-3-butoxy-phenyl)-2-ethoxy-acrylic acid a—(Z)-3-{3-butoxy-4-[2-(4-butanesulfonyloxy-3-methoxy-phenyl)-ethoxy]-phenyl}-2-ethoxy-ethyl acrylate 0.4 ml (3.1 mmol) of butanesulfonyl chloride is added to a solution of 0.95 g (2.1 mmol) of (Z)-3-{3-butoxy-4-[2-(4-hydroxy-3-methoxy-phenyl)-ethoxy]-phenyl}-2-ethoxy-ethyl acrylate (prepared according to Example 7d) and 0.34 ml (2.5 mmol) of triethylamine in 10 ml of dichloromethane. The reaction mixture is stirred at room temperature for 15 hours and then the reaction mixture is concentrated under vacuum. The raw product obtained is purified by silica column chromatography, eluted with a heptane/ethyl acetate mixture 80/20 to give 0.73 g (61%) of (Z)-3-{3-butoxy-4-[2-(4-butanesulfonyloxy-3-methoxy-phenyl)-ethoxy]-phenyl}-2-ethoxy-ethyl acrylate in the form of a pale yellow oil.

b—(Z)-3-{3-butoxy-4-[2-(4-butanesulfonyloxy-3-methoxy-phenyl)-ethoxy]-phenyl}-2-ethoxy-acrylic acid 6.3 ml (6.3 mmol) of an aqueous solution of sodium hydroxide of concentration 1M is added to a solution of 0.73 g (1.26 mmol) of (Z)-3-{3-butoxy-4-[2-(4-butanesulfonyloxy-3-methoxy-phenyl)-ethoxy]-phenyl}-2-ethoxy-ethyl acrylate in 15 ml of tetrahydrofuran. The reaction mixture is stirred at 68° C. for 30 h. After cooling, the reaction mixture is treated by adding an aqueous solution of hydrochloric acid of concentration 1M plus 20 ml of water and then extracted with ethyl acetate. The organic phases are combined, washed with saturated sodium chloride solution, dried over magnesium sulfate, filtered and then evaporated. The product is recrystallized from diisopropyl ether to obtain 0.5 g (72%) of (Z)-3-{3-butoxy-4-[2-(4-butanesulfonyloxy-3-methoxy-phenyl)-ethoxy]-phenyl}-2-ethoxy-acrylic acid in the form of a white solid with melting point of 94° C.

$^1$H NMR (δ, CDCl$_3$): 093 (t, 3H, J=7.4 Hz); 0.95 (t, 3H, J=7.4 Hz); 1.36 (t, 3H, J=7.1 Hz); 1.45 (m, 2H); 1.78 (m, 2H); 1.95 (m, 2H); 3.09 (t, J=6.6 Hz); 3.24 (m, 2H); 3.83 (s, 3H); 3.95-4.00 (m, 4H); 4.20 (t, 2H, J=6.8 Hz); 6.79 (d, 1H, J=8.4 Hz); 6.88 (dd, 1H, J=8.2 Hz, J=1.9 Hz); 6.92 (s, 1H); 7.06 (s, 1H); 7.17-7.22 (m, 2H); 7.53 (s, 1H);

EXAMPLE 9

(Z)-3-(4-{2-[4-(butane-1-sulfonyloxy)-2-methoxy-phenyl]-ethoxy}-3-butoxy-phenyl)-2-ethoxy-acrylic acid a—2-methoxy-4-(2-methoxy-ethoxymethoxy)-benzaldehyde 1.8 g (41.2 mmol) of 60% sodium hydride is added in portions to a solution at 0° C. of 5.7 g (37.5 mmol) of 4-hydroxy-2-methoxy-benzaldehyde diluted in 30 ml of tetrahydrofuran and 30 ml of dimethylformamide. The reaction mixture is stirred at room temperature for 30 minutes and then 4.7 ml (41.2 mmol) of 2-methoxyethoxymethyl chloride is added dropwise. The reaction mixture is stirred at room temperature for 45 minutes and then the reaction mixture is treated by adding water and extracted with ethyl acetate. The organic phases are combined, washed with saturated sodium chloride solution, dried over magnesium sulfate, filtered, and evaporated. The raw product is purified by silica column chromatography, eluted with a heptane/ethyl acetate mixture 70/30 to give 8.6 g (95%) of 2-methoxy-4-(2-methoxy-ethoxymethoxy)-benzaldehyde in the form of a colorless oil.

b—2-methoxy-4-(2-methoxy-ethoxymethoxy)-1-vinyl-benzene 12.5 ml (31.2 mmol) of n-butyllithium is added dropwise to a solution at −40° C. of 11.1 g (31.2 mmol) of methyl-triphenyl-phosphonium diluted in 100 ml of tetrahydrofuran. The reaction mixture is stirred at 0° C. for 30 minutes and then cooled to −25° C. and a solution of 5 g (20.8 mmol) of 2-methoxy-4-(2-methoxyethoxymethoxy)-benzaldehyde diluted in 50 ml of tetrahydrofuran is added dropwise. The reaction mixture is stirred at room temperature for 2 hours. The reaction mixture is treated by adding water and then extracted with ethyl acetate. The organic phases are combined, washed with saturated sodium chloride solution, dried over magnesium sulfate, filtered, and evaporated. The raw product is purified by silica column chromatography, eluted with a heptane/ethyl acetate mixture 75/25 to give 4.4 g (90%) of 2-methoxy-4-(2-methoxy-ethoxymethoxy)-1-vinyl-benzene in the form of a colorless oil.

c—2-[2-methoxy-4-(2-methoxy-ethoxymethoxy)-phenyl]-ethanol 3.9 g (16.4 mmol) of 2-methoxy-4-(2-methoxy-ethoxymethoxy)-1-vinyl-benzene diluted in 30 ml of tetrahydrofuran is added dropwise to a solution at room temperature of 4 g (16.4 mmol) of the dimer of 9-borabicyclo[3.3.1] nonane diluted in 10 ml of tetrahydrofuran. After stirring at room temperature for 20 hours, the above reaction mixture is cooled to 0° C. and 10 ml of water is added dropwise. The reaction mixture is stirred at room temperature for 1 hour and then cooled again to 0° C. and 10 ml of hydrogen peroxide is added. After stirring for 2 hours at room temperature, the reaction mixture is treated by adding 3 ml of an aqueous solution of sodium hydroxide of concentration 3M and stirred for 30 minutes. The reaction mixture is extracted with ethyl acetate. The organic phases are combined, washed with saturated sodium chloride solution, dried over magnesium sulfate, filtered, and evaporated. The raw product is purified by silica column chromatography, eluted with a heptane/ethyl acetate mixture 60/40 to give 3.3 g (78%) of 2-[2-methoxy-4-(2-methoxy-ethoxymethoxy)-phenyl]-ethanol in the form of a light yellow oil.

d—(Z)-3-(3-butoxy-4-{2-[2-methoxy-4-(2-methoxy-ethoxymethoxy)-phenyl]-ethoxy}-phenyl)-2-ethoxy-ethyl acrylate 3.3 g (13 mmol) of 2-[2-methoxy-4-(2-methoxy-ethoxymethoxy)-phenyl]-ethanol, 2 g (6.5 mmol) of (Z)-3-(3-butoxy-4-hydroxy-phenyl)-2-ethoxy-ethyl acrylate (prepared according to Example 5b) and 3.4 g (13 mmol) of triphenylphosphine are put in 70 ml of tetrahydrofuran. Once completely dissolved, 2.1 ml (13 mmol) of diethylazodicarboxylate is poured very slowly into the reaction mixture. The reaction mixture is stirred for 15 hours at room temperature. After adding 30 ml of methanol, the solvents are evaporated under vacuum and the raw product is purified by silica column chromatography, eluted with a heptane/ethyl acetate mixture 75/25 to give 2.6 g (74%) of (Z)-3-(3-butoxy-4-{2-[2-methoxy-4-(2-methoxy-ethoxymethoxy)-phenyl]-ethoxy}-phenyl)-2-ethoxy-ethyl acrylate in the form of a light yellow oil.

e—(Z)-3-{3-butoxy-4-[2-(4-hydroxy-2-methoxy-phenyl)-ethoxy]-phenyl}-2-ethoxy-ethyl acrylate 0.5 ml of sulfuric acid is added to a solution of 2.6 g (4.7 mmol) of (Z)-3-(3-butoxy-4-{2-[2-methoxy-4-(2-methoxy-ethoxymethoxy)-phenyl]-ethoxy}-phenyl)-2-ethoxy-ethyl acrylate in 15 ml of tetrahydrofuran and 15 ml of methanol. The reaction mixture is stirred at room temperature for 3 hours. The solvents are evaporated under vacuum and extraction with ethyl acetate/water is carried out. After separation of the phases, the organic phase is washed with water, dried over magnesium sulfate, filtered and concentrated under vacuum to give 2.1 g (100%) of (Z)-3-{3-butoxy-4-[2-(4-hydroxy-2-methoxy-phenyl)-ethoxy]-phenyl}-2-ethoxy-ethyl acrylate in the form of a light yellow solid.

f—(Z)-3-{3-butoxy-4-[2-(4-butanesulfonyloxy-2-methoxy-phenyl)-ethoxy]-phenyl}-2-ethoxy-ethyl acrylate 0.44 ml (3.4 mmol) of butanesulfonyl chloride is added to a solution of 1.05 g (2.3 mmol) of (Z)-3-{3-butoxy-4-[2-(4-hydroxy-2-methoxy-phenyl)-ethoxy]-phenyl}-2-ethoxy-ethyl acrylate and 0.47 ml (3.4 mmol) of triethylamine in 15 ml of dichloromethane. The reaction mixture is stirred at room temperature for 15 hours and then the reaction mixture is concentrated under vacuum. The raw product obtained is purified by silica column chromatography, eluted with a heptane/ethyl acetate mixture 75/25 to give 1.3 g (98%) of (Z)-3-{3-butoxy-4-[2-(4-butanesulfonyloxy-2-methoxy-phenyl)-ethoxy]-phenyl}-2-ethoxy-ethyl acrylate in the form of an orange-colored oil.

g—(Z)-3-{3-butoxy-4-[2-(4-butanesulfonyloxy-2-methoxy-phenyl)-ethoxy]-phenyl}-2-ethoxy-acrylic acid 11.2 ml (11.2 mmol) of an aqueous solution of sodium hydroxide of concentration 1M is added to a solution of 1.3 g (2.25 mmol) of (Z)-3-{3-butoxy-4-[2-(4-butanesulfonyloxy-2-methoxy-phenyl)-ethoxy]-phenyl}-2-ethoxy-ethyl acrylate in 30 ml of tetrahydrofuran. The reaction mixture is stirred at 68° C. for 3 days. After cooling, the reaction mixture is treated by adding an aqueous solution of hydrochloric acid of concentration 1M plus 20 ml of water and then extracted with ethyl acetate. The organic phases are combined, washed with saturated sodium chloride solution, dried over magnesium sulfate, filtered, and evaporated. The raw product is recrystallized from a heptane/ethyl acetate mixture to obtain 0.7 g (58%) of (Z)-3-{3-butoxy-4-[2-(4-butanesulfonyloxy-2-methoxy-phenyl)-ethoxy]-phenyl}-2-ethoxy-acrylic acid in the form of a white solid with melting point of 90° C.

$^1$H NMR (δ, CDCl$_3$): 0.93 (t, 3H, J=7.4 Hz); 0.95 (t, 3H, J=7.4 Hz); 1.32 (t, 3H, J=7.1 Hz); 1.42 (m, 2H); 1.78 (m, 2H); 3.08 (t, 2H, J=7 Hz); 3.18 (m, 2H); 3.78 (s, 3H); 3.95 (m, 4H); 4.13 (t, 2H, J=7.1 Hz); 6.71 (d, 1H, J=7.8 Hz); 6.73 (s, 1H); 6.80 (d, 1H, J=8.4 Hz); 7.04 (s, 1H); 7.15-7.22 (m, 2H); 7.50 (s, 1H).

EXAMPLE 10

(Z)-3-{3-butoxy-4-[2-(4-methanesulfonyloxy-2-methoxy-phenyl)-ethoxy]-phenyl}-2-ethoxy-acrylic acid a—(Z)-3-{3-butoxy-4-[2-(4-methanesulfonyloxy-2-methoxy-phenyl)-ethoxy]-phenyl}-2-ethoxy-ethyl acrylate 0.26 ml (3.40 mmol) of methanesulfonyl chloride is added to a solution of 1.05 g (2.30 mmol) of (Z)-3-{3-butoxy-4-[2-(4-hydroxy-2-methoxy-phenyl)-ethoxy]-phenyl}-2-ethoxy-ethyl acrylate (prepared according to Example 9e) and 0.47 ml (3.40 mmol) of triethylamine in 15 ml of dichloromethane. The reaction mixture is stirred at room temperature for 15 hours and then the reaction mixture is concentrated under vacuum. The raw product obtained is purified by silica column chromatography, eluted with a heptane/ethyl acetate mixture 70/30 to give 1 g (80%) of (Z)-3-{3-butoxy-4-[2-(4- methanesulfonyloxy-2-methoxy-phenyl)-ethoxy]-phenyl}-2-ethoxy-ethyl acrylate in the form of a colorless oil.

b—(Z)-3-{3-butoxy-4-[2-(4-methanesulfonyloxy-2-methoxy-phenyl)-ethoxy]-phenyl}-2-ethoxy-acrylic acid 9.5 ml (9.5 mmol) of an aqueous solution of sodium hydroxide of concentration 1M is added to a solution of 1 g (1.86 mmol) of (Z)-3-{3-butoxy-4-[2-(4-methanesulfonyloxy-2-methoxy-phenyl)-ethoxy]-phenyl}-2-ethoxy-ethyl acrylate in 30 ml of tetrahydrofuran. The reaction mixture is stirred at 68° C. for 2 days.

After cooling, the reaction mixture is treated by adding an aqueous solution of hydrochloric acid of concentration 1M plus 20 ml of water and then extracted with ethyl acetate. The organic phases are combined, washed with saturated sodium chloride solution, dried over magnesium sulfate, filtered and evaporated. The raw product is recrystallized from a heptane/ethyl acetate mixture to obtain 0.35 g (65%) of (Z)-3-{3-butoxy-4-[2-(4-methanesulfonyloxy-2-methoxy-phenyl)-ethoxy]-phenyl}-2-ethoxy-acrylic acid in the form of a white solid with melting point of 112° C.

$^1$H NMR (δ, CDCl$_3$): 0.93 (t, 3H, J=7.4 Hz); 1.32 (t, 3H, J=7.1 Hz); 1.45 (m, 2H); 1.78 (m, 2H); 3.06 (m, 2H); 3.08 (s, 3H); 3.78 (s, 3H); 3.92-3.97 (m, 4H); 4.14 (t, 2H, J=7.1 Hz); 6.73 (m, 2H); 6.80 (d, 1H, J=8.4 Hz); 7.03 (s, 1H); 7.15-7.24 (m, 2H); 7.49 (s, 1H);

EXAMPLE 11

(Z)-3-{3-butoxy-4-[2-(4-ethoxy-3-fluoro-phenyl)-ethoxy]-phenyl}-2-ethoxy-acrylic acid a—(3-fluoro-4-hydroxy-phenyl)-methyl acetate 1 ml of sulfuric acid is added to a solution of 9.6 g (56.4 mmol) of (3-fluoro-4-hydroxy-phenyl)-acetic acid in 100 ml of methanol. The reaction mixture is stirred at 68° C. for 2 hours and then concentrated under vacuum. After adding 100 ml of water and 100 ml of ethyl acetate, the reaction mixture is extracted with ethyl acetate. The organic phases are combined, washed with saturated sodium chloride solution and then dried over magnesium sulfate, filtered, and evaporated. 10 g (100%) of (3-fluoro-4-hydroxy-phenyl)-methyl acetate is obtained in the form of a light yellow oil.

b—[3-fluoro-4-(2-methoxy-ethoxymethoxy)-phenyl] methyl acetate 2.6 g (65.1 mmol) of 60% sodium hydride is added in portions to a solution at 0° C. of 10 g (54.3 mmol) of (3-fluoro-4-hydroxy-phenyl)-methyl acetate diluted in 50 ml of tetrahydrofuran and 50 ml of dimethylformamide. The reaction mixture is stirred at room temperature for 45 minutes and then 6.8 ml (59.7 mmol) of 2-methoxyethoxymethyl chloride is added dropwise. The reaction mixture is stirred at room temperature for 2 hours and then the reaction mixture is treated by adding water and extracted with ethyl acetate. The organic phases are combined, washed with saturated aqueous sodium chloride solution, dried over magnesium sulfate, filtered, and evaporated. The raw product is purified by silica column chromatography, eluted with a heptane/ethyl acetate mixture 70/30. 9.7 g (65%) of [3-fluoro-4-(2-methoxy-ethoxymethoxy)-phenyl]-methyl acetate is obtained in the form of a colorless oil.

c—2-[3-fluoro-4-(2-methoxy-ethoxymethoxy)-phenyl]-ethanol 2.4 g (107 mmol) of lithium borohydride is added in portions to a solution of 9.7 g (36 mmol) of [3-fluoro-4-(2-methoxy-ethoxymethoxy)-phenyl]-methyl acetate in 100 ml of tetrahydrofuran. The reaction mixture is stirred at 60° C. for 1.5 h and then it is poured into 500 ml of ice and extracted with ethyl acetate. The organic phases are combined, washed with saturated aqueous sodium chloride solution, dried over magnesium sulfate, filtered, and evaporated. 8.6 g (99%) of 2-[3-fluoro-4-(2-methoxy-ethoxymethoxy)-phenyl]-ethanol is obtained in the form of a colorless oil.

d—(Z)-3-(3-butoxy-4-{2-[3-fluoro-4-(2-methoxy-ethoxymethoxy)-phenyl]-ethoxy}-phenyl)-2-ethoxy-ethyl acrylate 2.2 g (9.1 mmol) of 2-[3-fluoro-4-(2-methoxy-ethoxymethoxy)-phenyl]-ethanol, 2 g (6.5 mmol) of (Z)-3-(3-butoxy-4-hydroxy-phenyl)-2-ethoxy-ethyl acrylate (prepared according to Example 5b) and 3.4 g (13 mmol) of triphenylphosphine are put in 70 ml of tetrahydrofuran. Once completely dissolved, 2.1 ml (13 mmol) of diethylazodicarboxylate is poured very slowly into the reaction mixture. The reaction mixture is stirred for 15 hours at room temperature. After adding 50 ml of methanol, the solvents are evaporated under vacuum and the raw product is purified by silica column chromatography, eluted with a heptane/ethyl acetate mixture 70/30 to give 2.5 g (71%) of (Z)-3-(3-butoxy-4-{2-[3-fluoro-4-(2-methoxy-ethoxymethoxy)-phenyl]-ethoxy}-phenyl)-2-ethoxy-ethyl acrylate in the form of a pink oil.

e—(Z)-3-{3-butoxy-4-[2-(3-fluoro-4-hydroxy-phenyl)-ethoxy]-phenyl}-2-ethoxy-ethyl acrylate 0.5 ml of sulfuric acid is added to a solution of 2.5 g (4.7 mmol) of (Z)-3-(3-butoxy-4-{2-[3-fluoro-4-(2-methoxy-ethoxymethoxy)-phenyl]-ethoxy}-phenyl)-2-ethoxy-ethyl acrylate in 15 ml of tetrahydrofuran and 15 ml of methanol. The reaction mixture is stirred at room temperature for 15 hours. The solvents are evaporated under vacuum and extraction with ethyl acetate/water is carried out. After separation of the phases, the organic phase is washed with water and then dried over magnesium sulfate, filtered and concentrated under vacuum to give 2.1 g (100%) of (Z)-3-{3-butoxy-4-[2-(3-fluoro-4-hydroxy-phenyl)-ethoxy]-phenyl}-2-ethoxy-ethyl acrylate in the form of a pink solid.

f—(Z)-3-{3-butoxy-4-[2-(4-ethoxy-3-fluoro-phenyl)-ethoxy]-phenyl}-2-ethoxy-ethyl acrylate 0.13 ml (1.7 mmol) of ethyl iodide is added to a solution of 0.50 g (1.1 mmol) of (Z)-3-{3-butoxy-4-[2-(3-fluoro-4-hydroxy-phenyl)-ethoxy]-phenyl}-2-ethoxy-ethyl acrylate and 0.23 g (1.7 mmol) of potassium carbonate in 10 ml of 2-butanone. The reaction mixture is stirred and heated at 80° C. for 4 hours and then the reaction mixture is filtered and the filtrate is concentrated under vacuum. The raw product obtained is purified by silica column chromatography, eluted with a heptane/ethyl acetate mixture 90/10 to give 0.4 g (75%) of (Z)-3-{3-butoxy-4-[2-(4-ethoxy-3-fluoro-phenyl)-ethoxy]-phenyl}-2-ethoxy-ethyl acrylate in the form of a pale yellow oil, which crystallizes.

g—(Z)-3-{3-butoxy-4-[2-(4-ethoxy-3-fluoro-phenyl)-ethoxy]-phenyl}-2-ethoxy-acrylic acid 2.5 ml (2.5 mmol) of an aqueous solution of lithium hydroxide of concentration 1M is added to a solution of 0.4 g (0.84 mmol) of (Z)-3-{3-butoxy-4-[2-(4-ethoxy-3-fluoro-phenyl)-ethoxy]-phenyl}-2-ethoxy-ethyl acrylate in 6 ml of tetrahydrofuran. The reaction mixture is stirred at room temperature for 4 days. The reaction mixture is treated by adding an aqueous solution of hydrochloric acid of concentration 1M plus 10 ml of water and then extracted with ethyl acetate. The organic phases are combined, washed with saturated aqueous sodium chloride solution, dried over magnesium sulfate, filtered and evaporated. The raw product is recrystallized from a heptane/ethyl acetate mixture 80/20 to obtain 0.3 g (81%) of (Z)-3-{3-butoxy-4-[2-(4-ethoxy-3-fluoro-phenyl)-ethoxy]-phenyl}-2-ethoxy-acrylic acid in the form of a white solid with melting point of 119° C.

$^1$H NMR ($\delta$, CDCl$_3$): 1.02 (t, 3H, J=7.4 Hz); 1.44 (t, 3H, J=7.1 Hz); 1.53 (t, 3H, J=7.5 Hz); 1.85 (m, 2H); 1.89 (m, 2H); 3.08 (t, 2H, J=6.6 Hz, 4.02 (m, 4H); 4.10 (q, 2H, J=7.1 Hz); 4.21 (t, 2H, J=6.7 Hz); 6.84-6.90 (m, 2H); 7.00 (d, 1H, J=8.2 Hz); 7.11 (m, 1H); 7.13 (s, 1H); 7.24 (m, 1H); 7.57 (s, 1H).

EXAMPLE 12

(Z)-3-{3-butoxy-4-[2-(3-fluoro-4-pentyloxy-phenyl)-ethoxy]-phenyl}-2-ethoxy-acrylic acid a—(Z)-3-{3-butoxy-4-[2-(3-fluoro-4-pentyloxy-phenyl)-ethoxy]-phenyl}-2-ethoxy-ethyl acrylate 0.2 ml (1.7 mmol) of pentyl iodide is added to a solution of 0.5 g (1.1 mmol) of (Z)-3-{3-butoxy-4-[2-(3-fluoro-4-hydroxy-phenyl)-ethoxy]-phenyl}-2-ethoxy-ethyl acrylate (prepared according to Example 11e) and 0.2 g (1.7 mmol) of potassium carbonate in 10 ml of 2-butanone. The reaction mixture is stirred at 80° C. for 7 hours. The reaction mixture is filtered and the filtrate is concentrated under vacuum. The raw product obtained is purified by silica column chromatography, eluted with a heptane/ethyl acetate mixture 90/10 to give 0.42 g (72%) of (Z)-3-{3-butoxy-4-[2-(3-fluoro-4-pentyloxy-phenyl)-ethoxy]-phenyl}-2-ethoxy-ethyl acrylate in the form of a colorless oil.

b—(Z)-3-{3-butoxy-4-[2-(3-fluoro-4-pentyloxy-phenyl)-ethoxy]-phenyl}-2-ethoxy-acrylic acid 2.4 ml (2.4 mmol) of an aqueous solution of lithium hydroxide of concentration 1M is added to a solution of 0.42 g (0.8 mmol) of (Z)-3-{3-butoxy-4-[2-(3-fluoro-4-pentyloxy-phenyl)-ethoxy]-phenyl}-2-ethoxy-ethyl acrylate in 6 ml of tetrahydrofuran. The reaction mixture is stirred at room temperature for 4 days. The reaction mixture is treated by adding an aqueous solution of hydrochloric acid of concentration 1M plus 10 ml of water and then extracted with ethyl acetate. The organic phases are combined, washed with saturated sodium chloride solution, dried over magnesium sulfate, filtered, and evaporated. The raw product is recrystallized from a heptane/ethyl acetate mixture 80/20 to obtain 0.34 g (87%) of (Z)-3-{3-butoxy-4-[2-(3-fluoro-4-pentyloxy-phenyl)-ethoxy]-phenyl}-2-ethoxy-acrylic acid in the form of a white solid with melting point of 102° C.

$^1$H NMR ($\delta$, CDCl$_3$): 0.94 (t, 3H, J=7.1 Hz); 1.02 (t, 3H, J=7.4 Hz); 1.41 (t, J=7 Hz); 1.45 (m, 2H); 1.83 (m, 2H); 3.08 (t, 2H, J=6.6 Hz); 4.00-4.06 (m, 6H); 4.21 (t, 2H, J=6.7 Hz); 6.84-6.90 (m, 4H); 6.99 (d, 1H, J=8.3 Hz); 7.10 (m, 1H); 7.13 (s, 3H); 7.24 (m, 1H); 7.57 (s, 1H).

EXAMPLE 13

(Z)-3-(4-{2-[4-(butane-1-sulfonyloxy)-3-fluoro-phenyl]-ethoxy}-3-butoxy-phenyl)-2-ethoxy-acrylic acid a—(Z)-3-{3-butoxy-4-[2-(3-fluoro-4-butanesulfonyloxy-phenyl)-ethoxy]-phenyl}-2-ethoxy-ethyl acrylate 0.22 ml (1.75 mmol) of butanesulfonyl chloride is added to a solution of 0.52 g (1.16 mmol) of (Z)-3-{3-butoxy-4-[2-(3-fluoro-4-hydroxy-phenyl)-ethoxy]-phenyl}-2-ethoxy-ethyl acrylate (prepared according to Example 11e) and 0.24 ml (1.75 mmol) of triethylamine in 10 ml of dichloromethane. The reaction mixture is stirred at room temperature for 15 hours and then the reaction mixture is concentrated under vacuum. The raw product obtained is purified by silica column chromatography, eluted with a heptane/ethyl acetate mixture 80/20 to give 0.41 g (62%) of (Z)-3-{3-butoxy-4-[2-(3-fluoro-4-butanesulfonyloxy-phenyl)-ethoxy]-phenyl}-2-ethoxy-ethyl acrylate in the form of a colorless oil.

b—(Z)-3-(4-{2-[4-(butane-1-sulfonyloxy)-3-fluoro-phenyl]-ethoxy}-3-butoxy-phenyl)-2-ethoxy-acrylic acid 1.4 ml (1.4 mmol) of an aqueous solution of lithium hydroxide of concentration 1M is added to a solution of 0.4 g (0.7 mmol) of (Z)-3-(4-{2-[4-(butane-1-sulfonyloxy)-3-fluoro-phenyl]-ethoxy}-3-butoxy-phenyl)-2-ethoxy-ethyl acrylate in 6 ml of tetrahydrofuran. The reaction mixture is stirred at room temperature for 3 days.

The reaction mixture is treated by adding an aqueous solution of hydrochloric acid of concentration 1M plus 10 ml of water and then extracted with ethyl acetate. The organic phases are combined, washed with saturated aqueous sodium chloride solution, dried over magnesium sulfate, filtered, and evaporated. The raw product is purified by silica column chromatography, eluted with a dichloromethane/methanol mixture 99/1 to obtain 0.1 g (26%) of (Z)-3-(4-{2-[4-(butane-1-sulfonyloxy)-3-fluoro-phenyl]-ethoxy}-3-butoxy-phenyl)-2-ethoxy-acrylic acid in the form of a white solid with melting point of 99° C.

$^1$H NMR ($\delta$, CDCl$_3$): 0.91 (t, 3H, J=7.3 Hz); 0.93 (t, 3H, J=7.3 Hz); 1.32 (t, 3H, J=7.1 Hz); 1.44 (m, 2H); 1.75 (m, 2H); 1.92 (m, 2H); 3.06 (t, 2H, J=6.3 Hz); 3.23 (m, 2H); 3.93-3.97 (m, 4H); 4.15 (t, 2H, J=6.3 Hz); 6.75 (d, 1H, J=8.4 Hz); 7.14 (s, 1H); 7.15 (m, 1H); 7.17-7.20 (m, 3H); 7.49 (s, 1H).

EXAMPLE 14

(Z)-3-{3-butoxy-4-[2-(3-chloro-4-ethoxy-phenyl)-ethoxy]-phenyl}-2-ethoxy-acrylic acid a—[3-chloro-4-hydroxy-phenyl]-methyl acetate 1 ml of sulfuric acid is added to a solution of 10 g (53.6 mmol) of (3-chloro-4-hydroxy-phenyl)-acetic acid in 100 ml of methanol. The reaction mixture is stirred at 68° C. for 15 hours and then concentrated under vacuum. After adding 100 ml of water and 100 ml of ethyl acetate, the reaction mixture is extracted with ethyl acetate. The organic phases are combined, washed with saturated sodium chloride solution and then dried over magnesium sulfate, filtered, and evaporated.

11 g (100%) of (3-chloro-4-hydroxy-phenyl)-methyl acetate is obtained in the form of a light yellow oil.

b—[3-chloro-4-(2-methoxy-ethoxymethoxy)-phenyl]-methyl acetate 2.75 g (68.4 mmol) of 60% sodium hydride is added in portions to a solution at 0° C. of 11 g (57 mmol) of (3-chloro-4-hydroxy-phenyl)-methyl acetate diluted in 60 ml of tetrahydrofuran and 60 ml of dimethylformamide. The reaction mixture is stirred at room temperature for 45 minutes and then 7.2 ml (62.7 mmol) of 2-methoxyethoxymethyl chloride is added dropwise. The reaction mixture is stirred at room temperature for 2 hours and then the reaction mixture is treated by adding water and extracted with ethyl acetate. The organic phases are combined, washed with saturated sodium chloride solution, dried over magnesium sulfate, filtered, and evaporated. The raw product is purified by silica column chromatography, eluted with a heptane/ethyl acetate mixture 70/30. 10.6 g (66%) of [3-chloro-4-(2-methoxy-ethoxymethoxy)-phenyl]-methyl acetate is obtained in the form of a colorless oil.

c—2-[3-chloro-4-(2-methoxy-ethoxymethoxy)-phenyl]-ethanol 2.4 g (110 mmol) of lithium borohydride is added in portions to a solution of 10.6 g (36.7 mmol) of [3-chloro-4-(2-methoxy-ethoxymethoxy)-phenyl]-methyl acetate diluted in 110 ml of tetrahydrofuran. The reaction mixture is stirred at 60° C. for 2 hours. The reaction mixture is then poured into 500 ml of ice and then extracted with ethyl acetate. The organic phases are combined, washed with saturated aqueous sodium chloride solution, dried over magnesium sulfate, filtered, and evaporated. The solvents are evaporated to give 7.3 g (77%) of 2-[3-chloro-4-(2-methoxy-ethoxymethoxy)-phenyl]-ethanol in the form of a colorless oil.

d—(Z)-3-(3-butoxy-4-{2-[3-chloro-4-(2-methoxy-ethoxymethoxy)-phenyl]-ethoxy}-phenyl)-2-ethoxy-ethyl acrylate 2.7 g (9.1 mmol) of 2-[3-chloro-4-(2-methoxy-ethoxymethoxy)-phenyl]-ethanol, 2 g (6.5 mmol) of (Z)-3-(3-butoxy-4-hydroxy-phenyl)-2-ethoxy-ethyl acrylate (prepared according to Example 5b) and 3.4 g (13 mmol) of triphenylphosphine are put in 80 ml of tetrahydrofuran. Once completely dissolved, 2.1 ml (13 mmol) of diethylazodicarboxylate is poured very slowly into the reaction mixture. The reaction mixture is stirred for 15 hours at room temperature. After adding 50 ml of methanol, the solvents are evaporated under vacuum and the raw product is purified by silica column chromatography, eluted with heptane/ethyl acetate 80/20 to give 2.6 g (72%) of (Z)-3-(3-butoxy-4-{2-[3-chloro-4-(2-methoxy-ethoxymethoxy)-phenyl]-ethoxy}-phenyl)-2-ethoxy-ethyl acrylate in the form of a colorless oil.

e—(Z)-3-{3-butoxy-4-[2-(3-chloro-4-hydroxy-phenyl)-ethoxy]-phenyl}-2-ethoxy-ethyl acrylate 0.5 ml of sulfuric acid is added to a solution of 2.6 g (4.7 mmol) of (Z)-3-(3-butoxy-4-{2-[3-chloro-4-(2-methoxy-ethoxymethoxy)-phenyl]-ethoxy}-phenyl)-2-ethoxy-ethyl acrylate in 15 ml of tetrahydrofuran and 15 ml of methanol. The reaction mixture is stirred at room temperature for 15 hours. The solvents are evaporated under vacuum and extraction with ethyl acetate/water is carried out. After separation of the phases, the organic phase is washed with water and then dried over magnesium sulfate, filtered and concentrated under vacuum to give 2.2 g (100%) of (Z)-3-{3-butoxy-4-[2-(3-chloro-4-hydroxy-phenyl)-ethoxy]-phenyl}-2-ethoxy-ethyl acrylate in the form of a light yellow solid.

f—(Z)-3-{3-butoxy-4-[2-(4-ethoxy-3-chloro-phenyl)-ethoxy]-phenyl}-2-ethoxy-ethyl acrylate 0.2 ml (2.4 mmol) of ethyl iodide is added to a solution of 0.55 g (1.2 mmol) of (Z)-3-{3-butoxy-4-[2-(3-chloro-4-hydroxy-phenyl)-ethoxy]-phenyl}-2-ethoxy-ethyl acrylate and 0.25 g (1.8 mmol) of potassium carbonate in 10 ml of 2-butanone. The reaction mixture is stirred at 80° C. for 6 hours. The reaction mixture is filtered and the filtrate is concentrated under vacuum. The raw product obtained is purified by silica column chromatography, eluted with a heptane/ethyl acetate mixture 85/15 to give 0.4 g (61%) of (Z)-3-{3-butoxy-4-[2-(4-ethoxy-3-chloro-phenyl)-ethoxy]-phenyl}-2-ethoxy-ethyl acrylate in the form of a colorless oil.

g—(Z)-3-{3-butoxy-4-[2-(4-ethoxy-3-chloro-phenyl)-ethoxy]-phenyl}-2-ethoxy-acrylic acid 2.2 ml (2.2 mmol) of an aqueous solution of lithium hydroxide of concentration 1M is added to a solution of 0.4 g (0.75 mmol) of (Z)-3-{3-butoxy-4-[2-(4-ethoxy-3-chloro-phenyl)-ethoxy]-phenyl}-2-ethoxy-ethyl acrylate in 6 ml of tetrahydrofuran. The reaction mixture is stirred at room temperature for 4 days. The reaction mixture is treated by adding an aqueous solution of hydrochloric acid of concentration 1M plus 10 ml of water and then extracted with ethyl acetate. The organic phases are combined, washed with saturated sodium chloride solution, dried over magnesium sulfate, filtered and evaporated. The product is recrystallized from a heptane/ethyl acetate mixture 80/20 to obtain 0.33 g (94%) of (Z)-3-{3-butoxy-4-[2-(4-ethoxy-3-chloro-phenyl)-ethoxy]-phenyl}-2-ethoxy-acrylic acid in the form of a white solid with melting point of 109° C.

$^1$H NMR (δ, CDCl$_3$): 1.02 (t, 3H, J=7.4 Hz); 1.41 (t, 3H, J=7.1 Hz); 1.48 (t, 3H, J=7 Hz); 1.56 (m, 2H); 1.86 (m, 2H); 3.08 (t, 2H, J=6.7 Hz); 4.01-4.06 (m, 4H); 4.12 (q, 2H, J=7 Hz); 4.21 (t, 2H, J=6.8 Hz); 6.84-6.88 (m, 4H); 7.12 (s, H); 7.16 (m, 1H); 7.24 (m, 1H); 7.36 (d, 1H, J=2.1 Hz); 7.58 (d, 1H, J=1.9 Hz).

EXAMPLE 15

(Z)-3-{3-butoxy-4-[2-(3-chloro-4-pentyloxy-phenyl)-ethoxy]-phenyl}-2-ethoxy-acrylic acid a—(Z)-3-{3-butoxy-4-[2-(3-chloro-4-pentyloxy-phenyl)-ethoxy]-phenyl}-2-ethoxy-ethyl acrylate 0.3 ml (2.4 mmol) of pentyl iodide is added to a solution of 0.55 g (1.2 mmol) of (Z)-3-{3-butoxy-4-[2-(3-chloro-4-hydroxy-phenyl)-ethoxy]-phenyl}-2-ethoxy-ethyl acrylate (prepared according to Example 14e) and 0.25 g (1.8 mmol) of potassium carbonate in 10 ml of 2-butanone. The reaction mixture is stirred at 80° C. for 6 hours. The reaction mixture is filtered and the filtrate is concentrated under vacuum. The raw product obtained is purified by silica column chromatography, eluted with a heptane/ethyl acetate mixture 90/10 to give 0.5 g (79%) of (Z)-3-{3-butoxy-4-[2-(3-chloro-4-pentyloxy-phenyl)-ethoxy]-phenyl}-2-ethoxy-ethyl acrylate in the form of a colorless oil.

b—(Z)-3-{3-butoxy-4-[2-(3-chloro-4-pentyloxy-phenyl)-ethoxy]-phenyl}-2-ethoxy-acrylic acid 2.8 ml (2.8 mmol) of an aqueous solution of lithium hydroxide of concentration 1M is added to a solution of 0.5 g (0.94 mmol) of (Z)-3-{3-butoxy-4-[2-(3-chloro-4-pentyloxy-phenyl)-ethoxy]-phenyl}-2-ethoxy-ethyl acrylate in 6 ml of tetrahydrofuran. The reaction mixture is stirred at room temperature for 4 days and then the reaction mixture is treated by adding an aqueous solution of hydrochloric acid of concentration 1M plus 10 ml of water and then extracted with ethyl acetate. The organic phases are combined, washed with saturated sodium chloride solution and then dried over magnesium sulfate, filtered, and evaporated. The raw product obtained is recrystallized from a heptane/ethyl acetate mixture 80/20 to obtain 0.4 g (80%) of (Z)-3-{3-butoxy-4-[2-(3-chloro-4-pentyloxy-phenyl)-ethoxy]-phenyl}-2-ethoxy-acrylic acid in the form of a white solid with melting point of 95° C.

$^1$H NMR (δ, CDCl$_3$): 0.95 (t, 3H, J=7.1 Hz); 1.02 (t, 3H, J=7.4 Hz); 1.43 (t, 3H, J=7.1 Hz); 1.47-1.57 (m, 2H); 1.86 (m, 4H); 3.07 (t, 2H, J=6.7 Hz); 4.00-4.07 (m, 6H); 4.21 (t, 2H, J=6.8 Hz); 6.84-6.87 (m, 2H); 7.13 (s, 1H); 7.14 (m, 1H); 7.24 (m, 1H); 7.35 (d, 1H, J=2.1 Hz); 7.59 (d, 1H, J=1.9 Hz).

EXAMPLE 16

(Z)-3-{3-butoxy-4-[2-(3-chloro-4-methanesulfonyloxy-phenyl)-ethoxy]-phenyl}-2-ethoxy-acrylic acid a—(Z)-3-{3-butoxy-4-[2-(3-chloro-4-methanesulfonyloxy-phenyl)-ethoxy]-phenyl}-2-ethoxy-ethyl acrylate 0.12 ml (1.6 mmol) of methanesulfonyl chloride is added to a solution of 0.50 g (1.1 mmol) of (Z)-3-{3-butoxy-4-[2-(3-chloro-4-hydroxy-phenyl)-ethoxy]-phenyl}-2-ethoxy-ethyl acrylate (prepared according to Example 14e) and 0.22 ml (1.6 mmol) of triethylamine in 10 ml of dichloromethane. The reaction mixture is stirred at room temperature for 15 hours and then the reaction mixture is concentrated under vacuum. The raw product obtained is purified by silica column chromatography, eluted with a heptane/ethyl acetate mixture 85/15 to give 0.5 g (84%) of (Z)-3-{3-butoxy-4-[2-(3-chloro-4-methanesulfonyloxy-phenyl)-ethoxy]-phenyl}-2-ethoxy-ethyl acrylate in the form of a colorless oil.

b—(Z)-3-{3-butoxy-4-[2-(3-chloro-4-methanesulfonyloxy-phenyl)-ethoxy]-phenyl}-2-ethoxy-acrylic acid 1.8 ml (1.8 mmol) of a solution of lithium hydroxide of concentration 1M is added to a solution of 0.5 g (0.9 mmol) of (Z)-3-{3-butoxy-4-[2-(3-chloro-4-methanesulfonyloxy-phenyl)-ethoxy]-phenyl}-2-ethoxy-ethyl acrylate in 6 ml of tetrahydrofuran. The reaction mixture is stirred at room temperature for 3 days.

The reaction mixture is treated by adding an aqueous solution of hydrochloric acid of concentration 1M plus 10 ml of water and then extracted with ethyl acetate. The organic phases are combined, washed with saturated aqueous sodium chloride solution, dried over magnesium sulfate, filtered and then evaporated. The raw product is purified by silica column chromatography, eluted with a dichloromethane/methanol mixture 99/1 to obtain 0.15 g (33%) of (Z)-3-{3-butoxy-4-[2-(3-chloro-4-methanesulfonyloxy-phenyl)-ethoxy]-phenyl}-2-ethoxy-acrylic acid in the form of a white solid with melting point of 113° C.

$^1$H NMR (δ, CDCl$_3$): 0.93 (t, 3H, J=7.4 Hz); 1.32 (t, 3H, J=7.1 Hz); 1.45 (t, 3H, J=7.1 Hz); 1.45 (m, 2H); 1.77 (m, 2H); 3.03 (t, 2H, J=6.3 Hz); 3.16 (s, 3H); 3.92-3.97 (s, 3H); 3.92-3.98 (m, H); 4.16 (t, 2H, J=6.34 Hz); 6.75 (d, 1H, J=8.4 Hz); 7.03 (s, 1H); 7.15-7.23 (m, 2H); 7.30 (m, 1H); 7.42 (d, 1H, J=2 Hz); 7.49 (d, 1H, J=1.9 Hz).

EXAMPLE 17

(Z)-3-(4-{2-[4-(butane-1-sulfonyloxy)-3-chloro-phenyl]-ethoxy}-3-butoxy-phenyl)-2-ethoxy-acrylic acid a—(Z)-3-{3-butoxy-4-[2-(3-chloro-4-butanesulfonyloxy-phenyl)-ethoxy]-phenyl}-2-ethoxy-ethyl acrylate 0.2 ml (1.6 mmol) of butanesulfonyl chloride is added to a solution of 0.5 g (1.1 mmol) of (Z)-3-{3-butoxy-4-[2-(3-chloro-4-hydroxy-phenyl)-ethoxy]-phenyl}-2-ethoxy-ethyl acrylate (prepared according to Example 14e) and 0.2 ml (1.6 mmol) of triethylamine in 10 ml of dichloromethane. The reaction mixture is stirred at room temperature for 15 hours and then the reaction mixture is concentrated under vacuum. The raw product obtained is purified by silica column chromatography, eluted with a heptane/ethyl acetate mixture 90/10 to give 0.4 g (62%) of (Z)-3-{3-butoxy-4-[2-(3-chloro-4-butanesulfonyloxy-phenyl)-ethoxy]-phenyl}-2-ethoxy-ethyl acrylate in the form of a colorless oil.

b—(Z)-3-(4-{2-[4-(butane-1-sulfonyloxy)-3-chloro-phenyl]-ethoxy}-3-butoxy-phenyl)-2-ethoxy-acrylic acid 1.3 ml (1.3 mmol) of an aqueous solution of lithium hydroxide of concentration 1M is added to a solution of 0.4 g (0.7 mmol) of (Z)-3-(4-{2-[4-(butane-1-sulfonyloxy)-3-chloro-phenyl]-ethoxy}-3-butoxy-phenyl)-2-ethoxy-ethyl acrylate in 6 ml of tetrahydrofuran. The reaction mixture is stirred at room temperature for 3 days.

The reaction mixture is treated by adding an aqueous solution of hydrochloric acid of concentration 1M plus 10 ml of water and then extracted with ethyl acetate. The organic phases are combined, washed with saturated aqueous sodium chloride solution, dried over magnesium sulfate, filtered and evaporated. The raw product is purified by silica column chromatography, eluted with a dichloromethane/methanol mixture 99/1 to obtain 0.07 g (19%) of (Z)-3-(4-{2-[4-(butane-1-sulfonyloxy)-3-chloro-phenyl]-ethoxy}-3-butoxy-phenyl)-2-ethoxy-acrylic acid in the form of a white solid with melting point of 80° C.

$^1$H NMR (δ, CDCl$_3$): 0.91 (t, 3H, J=7.3 Hz); 0.93 (t, 3H, J=7.3 Hz); 1.31 (t, 3H, J=7.1 Hz); 1.43-1.48 (m, 4H); 1.75 (m, 2H); 1.94 (m, 2H); 6.75 (d, 1H, J=8.4 Hz); 7.03 (s, 1H); 7.16-7.21 (m, 2H); 7.30 (d, 1H, J=8.4 Hz); 7.40 (d, 1H, J=2 Hz); 7.49 (d, 1H, J=1.9 Hz).

EXAMPLE 18

(Z)-2-Ethoxy-3-{4-[2-(4-methanesulfonyloxy-phenyl)-ethoxy]-3-methoxy-phenyl}-acrylic acid a—(Z)-3-(4-{2-[4-methanesulfonyloxy)-phenyl]-ethoxy}-3-methoxy-phenyl)-2-ethoxy-ethyl acrylate 0.13 ml (1.75 mmol) of methanesulfonyl chloride is added to a solution of 0.50 g (1.2 mmol) of (Z)-2-ethoxy-3-{4-[2-

(4-hydroxy-phenyl)-ethoxy]-3-methoxy-phenyl}-ethyl acrylate (prepared according to 1 h) and 0.24 ml (1.75 mmol) of triethylamine in 10 ml of dichloromethane. The reaction mixture is stirred at room temperature for 15 hours and then the solvents are evaporated under vacuum. The raw product obtained is purified by silica column chromatography, eluted with a heptane/ethyl acetate mixture 70/30 to give 0.46 g (85%) of (Z)-3-(4-{2-[4-(methanesulfonyloxy)-phenyl]-ethoxy}-3-methoxy-phenyl)-2-ethoxy-ethyl acrylate in the form of a colorless oil.

b—(Z)-3-(4-{2-[4-(methanesulfonyloxy)-phenyl]-ethoxy}-3-methoxy-phenyl)-2-ethoxy-acrylic acid 1.5 ml (1.5 mmol) of an aqueous solution of lithium hydroxide of concentration 1M is added to a solution of 0.5 g (1 mmol) of (Z)-3-(4-{2-[4-(methanesulfonyloxy)-phenyl]-ethoxy}-3-methoxy-phenyl)-2-ethoxy-ethyl acrylate in 15 ml of acetone and 5 ml of water. The reaction mixture is stirred at 35° C. for 18 hours. After cooling, the reaction mixture is treated by adding 2.5 ml of an aqueous solution of hydrochloric acid of concentration 1M plus 30 ml of water and then extracted with ethyl acetate. The organic phases are combined, washed with saturated sodium chloride solution, dried over magnesium sulfate, filtered and evaporated. The product is recrystallized from a heptane/ethyl acetate mixture to obtain 0.3 g (70%) of (Z)-3-(4-{2-[4-(methanesulfonyloxy)-phenyl]-ethoxy}-3-methoxy-phenyl)-2-ethoxy-acrylic acid in the form of a white solid with melting point of 147° C.
$^1$H NMR ($\delta$, CDCl$_3$): 1.43 (t, 1H, J=7.1 Hz); 3.16 (s, 3H); 3.20 (t, 2H, J=7.1 Hz); 3.92 (s, 3H); 4.07 (q, 2H, J=7.1 Hz); 4.27 (t, 2H, J=7.1 Hz); 6.86 (d, 1h, 8.4 Hz); 7.14 (s, 1H); 7.25-7.28 (m, 3H); 7.38 (m, 2H); 7.62 (d, 1H, J=1, 9 Hz);

EXAMPLE 19

(Z)-2-ethoxy-3-{4-[2-(4-ethoxy-phenyl)-ethoxy]-3-methoxy-phenyl}-acrylic acid a—(Z)-2-ethoxy-3-{4-[2-(4-ethoxy-phenyl)-ethoxy]-3-methoxy-phenyl}-ethyl acrylate 0.3 ml (3.5 mmol) of ethyl iodide is added to a solution of 0.5 g (1.2 mmol) of (Z)-2-ethoxy-3-{4-[2-(4-hydroxy-phenyl)-ethoxy]-3-methoxy-phenyl}-ethyl acrylate (prepared according to 1 h) and 0.4 g (2.6 mmol) of potassium carbonate in 10 ml of 2-butanone. The reaction mixture is stirred at 80° C. for 24 hours and then the reaction mixture is filtered and the filtrate is concentrated under vacuum. The raw product obtained is purified by silica column chromatography, eluted with a heptane/ethyl acetate mixture 90/10 to give 0.5 g (96%) of (Z)-2-ethoxy-3-{4-[2-(4-ethoxy-phenyl)-ethoxy]-3-methoxy-phenyl}-ethyl acrylate in the form of a colorless oil.

b—((Z)-2-ethoxy-3-{4-[2-(4-ethoxy-phenyl)-ethoxy]-3-methoxy-phenyl}-acrylic acid 1.7 ml (1.7 mmol) of an aqueous solution of lithium hydroxide of concentration 1M is added to a solution of 0.5 g (1.1 mmol) of (Z)-2-ethoxy-3-{4-[2-(4-ethoxy-phenyl)-ethoxy]-3-methoxy-phenyl}-ethyl acrylate in 15 ml of acetone and 5 ml of water. The reaction mixture is stirred at 35° C. for 18 hours. After cooling, the reaction mixture is treated by adding 2.6 ml of an aqueous solution of hydrochloric acid of concentration 1M plus 30 ml of water and then extracted with ethyl acetate. The organic phases are combined, washed with saturated aqueous sodium chloride solution and then dried over magnesium sulfate. After evaporation of the solvents, the product is recrystallized from a heptane/ethyl acetate mixture to obtain 0.25 g (58%) of ((Z)-2-ethoxy-3-{4-[2-(4-ethoxy-phenyl)-ethoxy]-3-methoxy-phenyl}-acrylic acid in the form of a white solid with melting point of 121° C.
$^1$H NMR ($\delta$, CDCl$_3$): 1.32 (t, 3H, J=6.2 Hz); 1.35 (t, 3H, J=7 Hz); 3.05 (t, 2H, J=7.7 Hz); 3.83 (s, 3H); 3.92-3.98 (m, 4H); 4.14 (t, 2H, J=7.6 Hz); 6.77-6.79 (m, 3H); 7.05 (s, 1H); 7.12-7.19 (m, 3H); 7.53 (d, 1H, J=1.9 Hz).

EXAMPLE 20

(Z)-2-ethoxy-3-{3-methoxy-4-[2-(4-pentyloxy-phenyl)-ethoxy]-phenyl}-acrylic acid a—(Z)-2-ethoxy-{3-4-[2-(4-pentyloxy-phenyl)-ethoxy]-3-methoxy-phenyl}-ethyl acrylate 0.5 ml (3.5 mmol) of pentyl iodide is added to a solution of 0.5 g (1.2 mmol) of (Z)-2-ethoxy-3-{4-[2-(4-hydroxy-phenyl)-ethoxy]-3-methoxy-phenyl}-ethyl acrylate (prepared according to Example 1h) and 0.4 g (2.6 mmol) of potassium carbonate in 10 ml of 2-butanone. The reaction mixture is stirred at 80° C. for 24 hours and then the reaction mixture is filtered and the filtrate is concentrated under vacuum. The raw product obtained is purified by silica column chromatography, eluted with a heptane/ethyl acetate mixture 90/10 to give 0.4 g (75%) of (Z)-2-ethoxy-{3-4-[2-(4-pentyloxy-phenyl)-ethoxy]-3-methoxy-phenyl}-ethyl acrylate in the form of a colorless oil.

b—(Z)-2-ethoxy-3-{4-[2-(4-pentyloxy-phenyl)-ethoxy]-3-methoxy-phenyl}-acrylic acid 1.3 ml (1.3 mmol) of an aqueous solution of lithium hydroxide of concentration 1M is added to a solution of 0.4 g (0.9 mmol) of ((Z)-2-ethoxy-3-{4-[2-(4-pentyloxy-phenyl)-ethoxy]-3-methoxy-phenyl}-ethyl acrylate in 15 ml of acetone and 5 ml of water. The reaction mixture is stirred at 35° C. for 18 hours. After cooling, the reaction mixture is treated by adding 2.3 ml of an aqueous solution of hydrochloric acid of concentration 1M plus 30 ml of water and then extracted with ethyl acetate. The organic phases are combined, washed with saturated sodium chloride solution, dried over magnesium sulfate, filtered, and evaporated. The product is recrystallized from a heptane/ethyl acetate mixture to obtain 0.3 g (84%) of ((Z)-2-ethoxy-3-{4-[2-(4-pentyloxy-phenyl)-ethoxy]-3-methoxy-phenyl}-acrylic acid in the form of a white solid with melting point of 135° C.
$^1$H NMR ($\delta$, CDCl$_3$): 0.95 (t, 3H, J=7.1 Hz); 1.38 (t, 3H, J=8 Hz); 1.39-1.48 (m, 4H); 1.82 (m, 2H); 3.14 (t, 2H, J=7.7 Hz); 3.93 (s, 3H); 3.97 (m, 2H); 4.04 (q, 2H, J=7.1 Hz); 4.23 (t, 2H, J=7.6 Hz).

EXAMPLE 21

(Z)-3-{4-[2-(4-acetylamino-phenyl)-ethoxy]-3-butoxy-phenyl}-2-ethoxy-acrylic acid a—(Z)-3-{3-butoxy-4-[2-(4-nitro-phenyl)-ethoxy]-phenyl}-2-ethoxy-ethyl acrylate 2.5 ml (16 mmol) of diethylazodicarboxylate is added very slowly to a solution of 2.5 g (8 mmol) of (Z)-3-(3-butoxy-4-hydroxy-phenyl)-2-ethoxy-ethyl acrylate (prepared according to Example 5b), 4.2 g (16 mmol) of triphenylphosphine and 2 g (12 mmol) of 4-nitrophenethyl alcohol in 50 ml of tetrahydrofuran. The reaction mixture is stirred for 15 hours at room temperature. After adding 50 ml of methanol, the solvents are evaporated under vacuum and the raw product is purified by silica column chromatography, eluted with a heptane/ethyl acetate mixture 70/30 to give 1.4 g (38%) of (Z)-3-{3-butoxy-4-[2-(4-nitro-phenyl)-ethoxy]-phenyl}-2-ethoxy-ethyl acrylate in the form of a yellow solid.

b—(Z)-3-{4-[2-(4-amino-phenyl)]-ethoxy-3-butoxy-phenyl}-2-ethoxy-ethyl acrylate 3.1 g (13 mmol) of tin chloride dihydrate is added to a solution of 1.2 g (2.7 mmol) of (Z)-3-{3-butoxy-4-[2-(4-nitro-phenyl)-ethoxy]-phenyl}-2-ethoxy-ethyl acrylate in 20 ml of absolute ethanol. The reaction mixture is heated at 70° C. for 15 hours. After adding a 5% aqueous solution of sodium hydrogen carbonate to pH7-8, the reaction mixture is extracted with ethyl acetate. The organic phases are combined, dried over magnesium sulfate, filtered and concentrated. The residue obtained is purified by silica column chromatography, eluted with a heptane/ethyl acetate mixture. 1 g (87%) of (Z)-3-{4-[2-(4-amino-phenyl)]-ethoxy-3-butoxy-phenyl}-2-ethoxy-ethyl acrylate is obtained.

c—(Z)-3-{4-[2-(4-acetylamino-phenyl)-ethoxy]-3-butoxy-phenyl}-2-ethoxy-ethyl acrylate 0.08 ml (1.1 mmol) of acetyl chloride is added to a solution of 0.4 g (1 mmol) of (Z)-3-{4-[2-(4-amino-phenyl)]-ethoxy-3-butoxy-phenyl}-2-ethoxy-ethyl acrylate, 0.2 ml (1.2 mmol) of triethylamine in 8 ml of tetrahydrofuran previously cooled to 0° C. After stirring at room temperature for 15 hours, the reaction mixture is treated with water and ethyl acetate. The organic phases are washed with water, dried over magnesium sulfate, filtered, and evaporated. The residue obtained is purified by silica column chromatography, eluted with a heptane/ethyl acetate mixture 80/20. 0.3 g (70%) of (Z)-3-{4-[2-(4-acetylamino-phenyl)-ethoxy]-3-butoxy-phenyl}-2-ethoxy-ethyl acrylate is obtained.

d—(Z)-3-{4-[2-(4-acetylamino-phenyl)-ethoxy]-3-butoxy-phenyl}-2-ethoxy-acrylic acid 80 mg (2 mmol) of sodium hydroxide as pellets is added to a solution of 0.3 g (0.6 mmol) of (Z)-3-{4-[2-(4-acetylamino-phenyl)-ethoxy]-3-butoxy-phenyl}-2-ethoxy-ethyl acrylate in 5 ml of tetrahydrofuran and 0.5 ml of water. The reaction mixture is stirred at room temperature for 18 hours. After cooling, the reaction mixture is treated by adding an aqueous solution of hydrochloric acid of concentration 1M plus water and then extracted with ethyl acetate. The organic phases are combined, washed with saturated sodium chloride solution, dried over magnesium sulfate, filtered, and evaporated. 0.05 g (16%) of (Z)-3-{4-[2-(4-acetylamino-phenyl)-ethoxy]-3-butoxy-phenyl}-2-ethoxy-acrylic acid is obtained in the form of a white solid with melting point of 160° C.

$^1$H NMR (δ, CDCl$_3$): 0.90 (t, 3H, J=7.4 Hz); 1.25 (t, 3H, J=7.1 Hz); 1.43 (m, 2H); 1.67 (m, 2H); 2.95 (t, 2H, J=6.5 Hz); 3.84-3.89 (m, 2H); 4.10 (t, 2H, J=6.6 Hz); 6.81 (d, 1H, J=8.4 Hz); 6.86 (s, 1H); 7.12 (dd, 1H, J=1.9 Hz, J=8.4 Hz); 7.17 (d, 2H, J=8.4 Hz); 7.37 (d, 2H, J=8.4 Hz); 7.47 (d, 1H, J=1.9 Hz).

EXAMPLE 22

(Z)-3-(4-{2-[4-(butane-1-sulfonylamino)-phenyl]-ethoxy}-3-butoxy-phenyl)-2-ethoxy-acrylic acid a—(Z)-3-(4-{2-[4-(butane-1-sulfonylamino)-phenyl]-ethoxy}-3-butoxy-phenyl)-2-ethoxy-ethyl acrylate 0.5 ml (4.2 mmol) of butanesulfonyl chloride is added to a solution of 1.2 g (2.8 mmol) of (Z)-3-{4-[2-(4-amino-phenyl)]-ethoxy-3-butoxy-phenyl}-2-ethoxy-ethyl acrylate (prepared according to Example 21b), 0.6 ml (4.2 mmol) of triethylamine in 15 ml of dichloromethane. The reaction mixture is stirred at room temperature for 15 hours and then concentrated under vacuum. The residue obtained is purified by silica column chromatography, eluted with a heptane/ethyl acetate mixture 80/20. 0.64 g (43%) of (Z)-3-(4-{2-[4-(butane-1-sulfonylamino)-phenyl]-ethoxy}-3-butoxy-phenyl)-2-ethoxy-ethyl acrylate is obtained.

b—(Z)-3-(4-{2-[4-(butane-1-sulfonylamino)-phenyl]-ethoxy}-3-butoxy-phenyl)-2-ethoxy-acrylic acid 2 ml (5 mmol) of a 10% aqueous solution of sodium hydroxide is added to a solution of 0.8 g (1.2 mmol) of (Z)-3-(4-{2-[4-(butane-1-sulfonylamino)-phenyl]-ethoxy}-3-butoxy-phenyl)-2-ethoxy-ethyl acrylate in 15 ml of acetone. The reaction mixture is stirred at 56° C. for 2 hours. After cooling, the reaction mixture is treated by adding 6 ml of an aqueous solution of acetic acid of concentration 1M plus 50 ml of water and then extracted with ethyl acetate. The organic phases are combined, washed with saturated sodium chloride solution, dried over magnesium sulfate, filtered and evaporated. The product is recrystallized from a diisopropylether/ethyl acetate mixture to obtain 0.4 g (61%) of (Z)-3-(4-{2-[4-(butane-1-sulfonylamino)-phenyl]-ethoxy}-3-butoxy-phenyl)-2-ethoxy-acrylic acid in the form of a beige solid with melting point of 164° C.

$^1$H NMR (δ, CDCl$_3$): 0.83 (t, 3H, J=7.3 Hz); 0.94 (t, 3H, J=7.3 Hz); 1.32 (t, 3H, J=7.1 Hz); 1.43-1.48 (m, 2H); 1.71-1.78 (m, 4H); 2.98-3.07 (m, 2H); 3.92-3.98 (m, 4H); 4.14 (t, 2H, J=6.7 Hz); 6.34 (s, 1H); 6.76 (d, 1H, J=8.4 Hz); 7.02 (s, 1H); 7.08 (d, 2H, J=8.4 Hz); 7.14 (m, 1h); 7.24 (d, 2H, J=8.4 Hz); 7.49 (s, 1H).

EXAMPLE 23

(Z)-3-(3-butoxy-4-{2-[4-(methanesulfonyl-methyl-amino)-phenyl]-ethoxy}-phenyl)-2-ethoxy-acrylic acid a—(Z)-3-{3-butoxy-4-[2-(4-methanesulfonylamino-phenyl)-ethoxy]-phenyl}-2-ethoxy-ethyl acrylate 0.3 ml (4.2 mmol) of methanesulfonyl chloride is added to a solution of 0.1 g (0.2 mmol) of (Z)-3-{4-[2-(4-amino-phenyl)]-ethoxy-3-butoxy-phenyl}-2-ethoxy-ethyl acrylate (prepared according to Example 21b), 0.05 ml (0.3 mmol) of triethylamine in 5 ml of dichloromethane. The reaction mixture is stirred at room temperature for 15 hours and then concentrated under vacuum. The residue obtained is purified by silica column chromatography, eluted with a heptane/ethyl acetate mixture 70/30. 0.1 g (83%) of (Z)-3-(3-butoxy-4-{2-[4-(methanesulfonyl-methyl-amino)-phenyl]-ethoxy}-phenyl)-2-ethoxy-ethyl acrylate is obtained.

b—(Z)-3-(3-butoxy-4-{2-[4-(methanesulfonyl-methyl-amino)-phenyl]-ethoxy}-phenyl)-2-ethoxy-ethyl acrylate 8 mg (0.2 mmol) of 60% sodium hydride is added to a solution of 0.09 g (0.2 mmol) of (Z)-3-(3-butoxy-4-{2-[4-(methanesulfonyl-methyl-amino)-phenyl]-ethoxy}-phenyl)-2-ethoxy-ethyl acrylate in 5 ml of dimethylformamide and then the reaction mixture is stirred for ten minutes at room temperature and 0.02 ml (0.3 mmol) of iodomethane is added. After adding water, the reaction mixture is extracted with ethyl acetate. The organic phases are combined, dried over magnesium sulfate, filtered, and evaporated. 45 mg (50%) of (Z)-3-(3-butoxy-4-{2-[4-(methanesulfonyl-methyl-amino)-phenyl]-ethoxy}-phenyl)-2-ethoxy-ethyl acrylate is obtained.

c—(Z)-3-(3-butoxy-4-{2-[4-(methanesulfonyl-methyl-amino)-phenyl]-ethoxy}-phenyl)-2-ethoxy-acrylic acid 0.12 ml (0.12 mmol) of an aqueous solution of lithium hydroxide of concentration 1M is added to a solution of 0.04 g (0.08 mmol) of (Z)-3-(3-butoxy-4-{2-[4-(methanesulfonyl-methyl-amino)-phenyl]-ethoxy}-phenyl)-2-ethoxy-ethyl acrylate in 3 ml of acetone and 1 ml of water. The reaction mixture is stirred at 35° C. for 18 hours. After cooling, the reaction mixture is treated by adding 0.2 ml of an aqueous solution of acetic acid of concentration 1M and 10 ml of water and then extracted with ethyl acetate. The organic phases are combined, washed with saturated aqueous sodium chloride solution, dried over magnesium sulfate, filtered, and evaporated. The product is purified by silica column chromatography, eluted with a heptane/ethyl acetate mixture: 50/50 to obtain 25 mg (64%) of (Z)-3-(3-butoxy-4-{2-[4-(methanesulfonyl-methyl-amino)-phenyl]-ethoxy}-phenyl)-2-ethoxy-acrylic acid in the form of a white solid with melting point of 112° C.

$^1$H NMR (δ, CDCl$_3$): 0.94 (t, 3H, J=7.4 Hz); 1.32 (t, 3H, J=7.1 Hz); 1.45 (m, 2H); 1.78 (m, 2H); 2.77 (s, 3H); 3.08 (t, 2H, J=6.7 Hz); 3.24 (s, 3H); 3.92-3.97 (m, 4H); 4.16 (t, 2H, J=6.8 Hz); 6.76 (d, 1H, J=8.4 Hz); 7.02 (s, 1H); 7.14-7.30 (m, 5H); 7.49 (d, 1H, J=1.9 Hz).

EXAMPLE 24

(Z)-3-{3-butoxy-4-[2-(4-methanesulfonylamino-phenyl)-ethoxy]-phenyl}-2-ethoxy-acrylic acid 4.4 ml (11 mmol) of a 10% aqueous solution of sodium hydroxide is added to a solution of 1.6 g (2.7 mmol) of (Z)-3-(3-butoxy-4-{2-[4-(methanesulfonylamino)-phenyl]-ethoxy}-phenyl)-2-ethoxy-ethyl acrylate (prepared according to Example 23a) in 30 ml of acetone and 5 ml of water. The reaction mixture is stirred at 56° C. for 24 hours. After cooling, the reaction mixture is treated by adding 12 ml of an aqueous solution of acetic acid of concentration 1M plus 100 ml of water and then extracted with ethyl acetate. The organic phases are combined, washed with saturated sodium chloride solution, dried over magnesium sulfate, filtered, and evaporated. The product is recrystallized from a diisopropylether/ethyl acetate mixture to obtain 0.8 g (61%) of (Z)-3-(4-{2-[4-(methanesulfonylamino)-phenyl]-ethoxy}-3-butoxy-phenyl)-2-ethoxy-acrylic acid in the form of a beige solid with melting point of 141° C.

$^1$H NMR (δ, CDCl$_3$): 0.94 (t, 3H, J=7.4 Hz); 1.32 (t, 3H, J=7.1 Hz); 1.43-1.49 (m, 2H); 1.73-1.78 (m, 2H); 2.93 (s, 3H); 3.05 (t, 2H, J=6.6 Hz); 3.92-3.98 (m, 4H); 4.14 (t, 2H, J=6.7 Hz); 6.56 (s, 1H); 6.76 (d, 1H, J=8.4 Hz); 7.02 (s, 1H); 7.09 (d, 2H, J=8.4 Hz); 7.15 (m, 1H); 7.25 (d, 2H, J=8.4 Hz); 7.50 (s, 1H).

EXAMPLE 25

(Z)-3-[4-(2-{4-[(butane-1-sulfonyl)-methyl-amino]-phenyl}-ethoxy)-3-butoxy-phenyl]-2-ethoxy-acrylic acid a—(Z)-3-[4-(2-{4-[(butane-1-sulfonyl)-methyl-amino]-phenyl}-ethoxy)-3-butoxy-phenyl]-2-ethoxy-ethyl acrylate 56 mg (1.4 mmol) of 60% sodium hydride is added to a solution of 0.64 g (1.2 mmol) of (Z)-3-(4-{2-[4-(butane-1-sulfonylamino)-phenyl]-ethoxy}-3-butoxy-phenyl)-2-ethoxy-ethyl acrylate (prepared according to Example 22a) in 10 ml of dimethylformamide and then the reaction mixture is stirred for twenty minutes at room temperature and 0.1 ml (1.75 mmol) of iodomethane is added and the reaction mixture is stirred at room temperature for 2 hours. After adding water, the reaction mixture is extracted with ethyl acetate. The organic phases are combined, dried over magnesium sulfate, filtered, and evaporated. The residue obtained is purified by silica column chromatography, eluted with a heptane/ethyl acetate mixture 70/30. 0.54 g (82%) of (Z)-3-[4-(2-{4-[(butane-1-sulfonyl)-methyl-amino]-phenyl}-ethoxy)-3-butoxy-phenyl]-2-ethoxy-ethyl acrylate is obtained.

b—(Z)-3-(3-butoxy-4-{2-[4-(butane-1-sulfonyl-methyl-amino)-phenyl]-ethoxy}-phenyl)-2-ethoxy-acrylic acid 1.4 ml (1.4 mmol) of an aqueous solution of lithium hydroxide of concentration 1M is added to a solution of 0.54 g (1 mmol) of (Z)-3-(3-butoxy-4-{2-[4-(butane-1-sulfonyl-methyl-amino)-phenyl]-ethoxy}-phenyl)-2-ethoxy-ethyl acrylate in 12 ml of acetone and 3 ml of water. The reaction mixture is stirred at 35° C. for 18 hours. After cooling, the reaction mixture is treated by adding 2.5 ml of an aqueous solution of acetic acid of concentration 1M plus 30 ml of water and then extracted with ethyl acetate. The organic phases are combined, washed with saturated sodium chloride solution, dried over magnesium sulfate, filtered and evaporated. The raw product is recrystallized from a diisopropyl ether/ethyl acetate mixture to obtain 0.4 g (82%) of (Z)-3-(3-butoxy-4-{2-[4-(butane-1-sulfonyl-methyl-amino)-phenyl]-ethoxy}-phenyl)-2-ethoxy-acrylic acid in the form of a white solid with melting point of 144° C.

$^1$H NMR (δ, CDCl$_3$): 0.69 (t, 3H, J=7.3 Hz); 0.78 (t, 3H, J=7.4 Hz); 1.17 (t, 3H, J=7.1 Hz); 1.30 (, 2H); 1.56-1.163 (m, 4H); 2.73-2.77 (m, 2H); 2.92 (t, 2H, J=6.7 Hz); 3.10 (s, 3H); 3.76-3.81 (m, 4H); 4.00 (t, 2H, J=6.7 Hz); 6.61 (d, 1H, J=8.4 Hz); 6.99 (s, 1H); 7.01-7.13 (m, 5H); 7.33 (d, 1H, J=1.9 Hz).

EXAMPLE 26

(Z)-3-{3-butoxy-4-[3-(4-methoxy-phenyl)-propyl]-phenyl}-2-ethoxy-acrylic acid a—3-butoxy-4-[3-(4-methoxy-phenyl)-propenyl]-methyl benzoate 170 mg (0.5 mmol) of 2-(dicyclohexylphosphino)biphenyl, 50 mg (0.25 mmol) of palladium acetate and then 2 ml (14 mmol) of triethylamine are added to a solution of 4 g (12 mmol) of 3-butoxy-4-iodomethyl benzoate (prepared according to Example 2c) and 2.1 g (14 mmol) of 4-allylanisole in 10 ml of dimethylformamide. The reaction mixture is heated at 90° C. for 15 hours. After adding 20 ml of water and then extracting with ethyl acetate, the organic phases are combined, washed with saturated sodium chloride solution and dried over sodium sulfate, filtered, and evaporated. 4.5 g (100%) of 3-butoxy-4-[(E)-3-(4-methoxy-phenyl)-propenyl]-methyl benzoate is obtained in the form of a yellow oil.

b—3-butoxy-4-[3-(4-methoxy-phenyl)-propyl]-methyl benzoate 0.45 g (10 wt. %) of 10% palladium on charcoal is added to a solution of 4.5 g (13 mmol) of 3-butoxy-4-[(E)-3-(4-methoxy-phenyl)-propenyl]-methyl benzoate in 60 ml of tetrahydrofuran previously purged with nitrogen. The medium is then placed under hydrogen at 3 bar for 3 hours. After filtration on Celite, the filtrate is concentrated under vacuum. 3.6 g (80%) of 3-butoxy-4-[3-(4-methoxy-phenyl)-propyl]-methyl benzoate is obtained.

c—{3-butoxy-4-[3-(4-methoxy-phenyl)-propyl]-phenyl}-methanol 0.9 g (40 mmol) of lithium borohydride is added in portions to a solution previously cooled to 0° C. of 3.6 g (10 mmol) of 3-butoxy-4-[3-(4-methoxy-phenyl)-propyl]-methyl benzoate in 80 ml of tetrahydrofuran and 4 ml of dimethylformamide. After addition from 0° C. up to room temperature for 15 hours, the reaction mixture is hydrolyzed by slowly adding ice and water and then extracted with ethyl acetate. The organic phase is washed with an aqueous solution of sodium chloride, dried over sodium sulfate, filtered, and evaporated. The residue is purified by silica column chromatography, eluted with a heptane/ethyl acetate mixture. 2.1 g (75%) of {3-butoxy-4-[3-(4-methoxy-phenyl)-propyl]-phenyl}-methanol is obtained.

d—3-butoxy-4-[2-(4-methoxy-phenyl)-ethoxy]-benzaldehyde 8.2 g (94 mmol) of manganese dioxide is added to a solution of 2.05 g (6.2 mmol) of {3-butoxy-4-[3-(4-methoxy-phenyl)-propyl]-phenyl}-methanol in 50 ml of dichloromethane. After stirring at room temperature for 15 hours, the reaction mixture is filtered on Celite and the filtrate is concentrated under vacuum. The residue is purified by silica column chromatography, eluted with a heptane/ethyl acetate mixture 92/8.

1.6 g (79%) of 3-butoxy-4-[2-(4-methoxy-phenyl)-ethoxy]-benzaldehyde is obtained.

e—(Z)-3-{3-butoxy-4-[3-(4-methoxy-phenyl)-propyl]phenyl}-2-ethoxy-ethyl acrylate 2.8 ml (20 mmol) of triethylamine is added to a solution of 1.6 g (5 mmol) of 3-butoxy-4-[2-(4-methoxy-phenyl)-ethoxy]-benzaldehyde and 3.1 g (7.3 mmol) of (ethoxy-ethoxycarbonyl-methyl)-triphenyl-phosphonium chloride (prepared according to Example 3a) in 30 ml of tetrahydrofuran. After stirring at 60° C. for 7 hours, the reaction mixture is concentrated under vacuum. The residue is purified by column chromatography eluted with a heptane/ethyl acetate mixture. 1.3 g (60%) of (Z)-3-{3-butoxy-4-[3-(4-methoxy-phenyl)-propyl]-phenyl}-2-ethoxy-ethyl acrylate is obtained.

f—(Z)-3-{3-butoxy-4-[3-(4-methoxy-phenyl)-propyl]-phenyl}-2-ethoxy-acrylic acid 0.1 g (2.7 mmol) of sodium hydroxide in pellet form is added to a solution of 0.4 g (0.9 mmol) of (Z)-3-{3-butoxy-4-[2-(4-methoxy-phenyl)-ethoxy]-phenyl}-2-ethoxy-ethyl acrylate in 5 ml of a tetrahydrofuran/water/methanol mixture 5/1/1. The reaction mixture is stirred at 55° C. for 7 hours and then 0.2 g (0.5 mmol) of sodium hydroxide and 5 ml of acetone are added and the reaction mixture is again heated for 15 hours. After cooling, the reaction mixture is treated by adding an aqueous solution of acetic acid up to pH4-5 plus water and then extracted with ethyl acetate. The organic phases are combined, washed with saturated sodium chloride solution, dried over magnesium sulfate, filtered, and evaporated. The residue obtained is purified by column chromatography eluted with a heptane/ethyl acetate mixture 80/20. 0.2 g (50%) of (Z)-3-{3-butoxy-4-[3-(4-methoxy-phenyl)-propyl]-phenyl}-2-ethoxy-acrylic acid is obtained in the form of a white solid with melting point of 65° C.

$^1$H NMR (δ, CDCl$_3$): 0.91 (t, 3H, J=7.4 Hz); 1.33 (t, 3H, J=7.1 Hz); 1.45 (m, 2H); 1.70 (m, 2H); 1.79 (m, 2H); 2.52-2.60 (m, 4H); 3.70 (s, 3H); 3.90 (t, 2H, J=6.6 Hz); 3.97 (q, 2H, J=7.1 Hz); 6.74 (d, 2H, J=8.4 Hz); 7.02-7.10 (m, 2H); 7.12 (d, 2H, J=8.4 Hz); 7.16 (m, 1H); 7.39 (s, 1H).

EXAMPLE 27

(Z)-3-(4-{2-[4-(acetyl-methyl-amino)-phenyl]-ethoxy}-3-butoxy-phenyl)-2-ethoxy-acrylic acid a—(Z)-3-(4-{2-[4-(acetyl-methyl-amino)-phenyl]-ethoxy}-3-butoxy-phenyl)-2-ethoxy-ethyl acrylate 50 mg (1.2 mmol) of 60% sodium hydride is added to a solution of 0.5 g (1 mmol) of (Z)-3-{4-[2-(4-acetylamino-phenyl)-ethoxy]-3-butoxy-phenyl}-2-ethoxy-ethyl acrylate (prepared according to Example 21c) in 8 ml of dimethylformamide and then the reaction mixture is stirred for ten minutes at room temperature and 0.2 ml (3 mmol) of iodomethane is added. After adding water, the reaction mixture is extracted with ethyl acetate. The organic phases are combined, dried over magnesium sulfate, filtered, and evaporated. The residue obtained is purified by silica column chromatography, eluted with a heptane/ethyl acetate mixture 75/25. 410 mg (80%) of (Z)-3-(4-{2-[4-(acetyl-methyl-amino)-phenyl]-ethoxy}-3-butoxy-phenyl)-2-ethoxy-ethyl acrylate is obtained.

b—(Z)-3-(4-{2-[4-(acetyl-methyl-amino)-phenyl]-ethoxy}-3-butoxy-phenyl)-2-ethoxy-acrylic acid 0.2 g (5 mmol) of sodium hydroxide in pellet form is added to a solution of 0.4 g (0.8 mmol) of (Z)-3-(4-{2-[4-(acetyl-methyl-amino)-phenyl]-ethoxy}-3-butoxy-phenyl)-2-ethoxy-ethyl acrylate in 5 ml of an acetone/water mixture 1/1. The reaction mixture is stirred at room temperature for 18 hours. After cooling, the reaction mixture is treated by adding an aqueous solution of acetic acid up to pH4-5 plus water and then extracted with ethyl acetate. The organic phases are combined, washed with saturated aqueous sodium chloride solution, dried over magnesium sulfate, filtered, and evaporated. The residue obtained is purified by column chromatography eluted with a heptane/ethyl acetate mixture 75/25. 0.3 g (80%) of (Z)-3-(4-{2-[4-(acetyl-methyl-amino)-phenyl]-ethoxy}-3-butoxy-phenyl)-2-ethoxy-acrylic acid is obtained in the form of a white solid with melting point of 121° C.

$^1$H NMR (δ, CDCl$_3$): 0.92 (t, 3H, J=7.4 Hz); 1.30 (t, 3H, J=7.1 Hz); 1.40-1.50 (m, 2H); 1.75 (m, 2H); 1.83 (s, 3H); 3.09 (t, 2H, J=6.6 Hz); 3.19 (s, 3H); 3.93-3.99 (m, 4H); 4.17 (t, 2H, J=6.6 Hz); 6.76 (d, 1H, J=8.4 Hz); 7.04 (s, 1H); 7.15 (d, 2H, J=8.4 Hz); 7.17 (m, 1H); 7.31 (d, 2H, J=8.4 Hz); 7.51 (d, 1H, J=1.9 Hz).

EXAMPLE 28

(Z)-3-{3-butoxy-4-[2-(4-propionylamino-phenyl)-ethoxy]-phenyl}-2-ethoxy-acrylic acid a—(Z)-3-{3-butoxy-4-[2-(4-propionylamino-phenyl)-ethoxy]-phenyl}-2-ethoxy-ethyl acrylate ml (1.3 mmol) of propionyl chloride is added to a solution of 0.5 g (1.2 mmol) of (Z)-3-{4-[2-(4-amino-phenyl)]-ethoxy-3-butoxy-phenyl}-2-ethoxy-ethyl acrylate (prepared as described in Example 21b), 0.2 ml (1.2 mmol) of triethylamine in 8 ml of tetrahydrofuran previously cooled to 0° C. After stirring at room temperature for 15 hours, the reaction mixture is treated with water and ethyl acetate. The organic phases are washed with water, dried over magnesium sulfate, filtered, and evaporated. The residue obtained is purified by silica column chromatography, eluted with a heptane/ethyl acetate mixture 80/20. 0.5 g (88%) of (Z)-3-{3-butoxy-4-[2-(4-propionylamino-phenyl)-ethoxy]-phenyl}-2-ethoxy-ethyl acrylate is obtained.

b—(Z)-3-{3-butoxy-4-[2-(4-propionylamino-phenyl)-ethoxy]-phenyl}-2-ethoxy-acrylic acid 0.15 g (3.1 mmol) of sodium hydroxide in pellet form is added to a solution of 0.25 g (5.2 mmol) of (Z)-3-{3-butoxy-4-[2-(4-propionylamino-phenyl)-ethoxy]-phenyl}-2-ethoxy-ethyl acrylate in 5 ml of an acetone/water mixture 1/1. The reaction mixture is stirred at room temperature for 18 hours. After cooling, the reaction mixture is treated by adding an aqueous solution of acetic acid up to pH4-5 plus water and then extracted with ethyl acetate. The organic phases are combined, washed with saturated sodium chloride solution, dried over magnesium sulfate, filtered, and evaporated.

The residue obtained is purified by silica column chromatography, eluted with a heptane/ethyl acetate mixture 75/25. 0.2 g (87%) of (Z)-3-{3-butoxy-4-[2-(4-propionylamino-phenyl)-ethoxy]-phenyl}-2-ethoxy-acrylic acid is obtained in the form of a white solid with melting point of 164° C.

$^1$H NMR (δ, CDCl$_3$): 0.88 (t, 3H, J=7.4 Hz); 1.09 (t, 3H, J=7.1 Hz); 1.23 (t, 3H, J=7.1 Hz); 1.40 (m, 2H); 1.65 (m, 2H); 2.24 (q, 2H, J=7.6 Hz); 2.27 (t, 2H, J=6.5 Hz); 3.83-3.89 (m, 4H); 4.08 (t, 2H, J=6.5 Hz); 6.78 (d, 1H, J=8.4 Hz); 6.85 (s, 1H); 7.10 (dd, 1H, J=1.7 Hz, J=8.4 Hz); 7.15 (d, 2H, J=8.4 Hz); 7.37 (d, 2H, J=8.4 Hz); 7.46 (s, 1H).

EXAMPLE 29

Tests of PPAR Transactivation in Crossed Curves

Activation of the PPAR receptors by an agonist (activator) in HeLN cells leads to the expression of a reporter gene, luciferase, which, in the presence of a substrate, generates light. The modulation of the PPAR receptors is measured by quantifying the luminescence produced after incubation of the cells in the presence of a reference agonist. The ligands will displace the agonist from its site. The activity is measured by quantifying the light produced. This measurement makes it possible to determine the modulating activity of the compounds according to the invention by determining the constant representing the affinity of the molecule for the PPAR receptor. This value, which can fluctuate according to the basal activity and expression of the receptor, is called apparent Kd (KdApp, nM).

To determine this constant, "crossed curves" of the test product versus a reference agonist are carried out in a 96-well plate: 10 concentrations of the test product plus a 0 concentration are arranged in rows, and 7 concentrations of the agonist plus a 0 concentration are arranged in columns. This is 88 measurement points for 1 product and 1 receptor. The 8 remaining wells are used for repeatability controls.

In each well, the cells are in contact with a concentration of the test product and a concentration of the reference agonist, 2-(4-{2-[3-(2,4-difluoro-phenyl)-1-heptyl-ureido]-ethyl}-phenylsulfanyl)-2-methyl-propionic acid for PPARα, {2-methyl-4-[4-methyl-2-(4-trifluoromethyl-phenyl)-thiazol-5-yl-methylsulfanyl]-phenoxy}-acetic acid for PPARδ and 5-{4-[2-(methyl-pyridin-2-yl-amino)-ethoxy]-benzyl}thiazolidine-2,4-dione for PPARγ. Measurements are also carried out for the total agonist controls with the same products.

The HeLN cell lines used are stable transfectants containing the plasmids ERE-βGlob-Luc-SV-Neo (reporter gene) and PPAR (α, δ, γ) Gal-hPPAR. These cells are sown in 96-well plates at a rate of 10 000 cells per well in 100 μl of DMEM medium without phenol red and supplemented with 10% of delipidated calf serum. The plates are then incubated at 37° C., 7% CO2 for 16 hours.

The various dilutions of the test products and of the reference ligand are added at a rate of 5 μl per well. The plates are then incubated for 18 hours at 37° C., 7% CO2.

The culture medium is removed by inverting and 100 μl of a 1:1 mixture PBS/Luciferine is added to each well. After 5 minutes, the plates are read with the luminescence reader.

These crossed curves make it possible to determine the AC50 (concentration at which 50% activation is observed) of the reference ligand at different concentrations of test product. These AC50 are used for calculating the Schild regression by plotting a straight line corresponding to the Schild equation ("Quantitation in receptor pharmacology" Terry P. Kenakin, Receptors and Channels, 2001, 7, 371-385) which provides the values of Kd app (in nM).

Results of Transactivation:

| Compounds | PPAR alpha Kd app (nM) | PPARs delta Kd app (in nM) | PPAR gamma Kd app (in nM) |
|---|---|---|---|
| Reference 1: 2-(4-{2-[3-(2,4-difluoro-phenyl)-1-heptyl-ureido]-ethyl}-phenylsulfanyl)-2-methyl-propionic acid | 200 | N/A | N/A |

-continued

| Compounds | PPAR alpha Kd app (nM) | PPARs delta Kd app (in nM) | PPAR gamma Kd app (in nM) |
|---|---|---|---|
| Reference 2: {2-methyl-4-[4-methyl-2-(4-trifluoromethyl-phenyl)-thiazol-5-ylmethylsulfanyl]-phenoxy}-acetic acid | N/A | 10 | N/A |
| Reference 3: 5-{4-[2-(methyl-pyridin-2-yl-amino)-ethoxy]-benzyl}-thiazolidine-2,4-dione | N/A | N/A | 30 |
| Example 1 | 9999 | 9999 | 8 |
| Example 3 | 60 | 250 | 15 |
| Example 6 | 120 | 4000 | 2 |
| Example 7 | 250 | 4000 | 15 |
| Example 8 | 120 | 2000 | 15 |
| Example 9 | 2000 | 4000 | 8 |
| Example 13 | 250 | 2000 | 8 |
| Example 17 | 60 | 1000 | 8 |

These results show the affinity of the compounds for the PPAR receptors and more particularly the specificity of the affinity of the compounds of the invention for the PPARγ subtype, compared with the affinity of the compounds for the PPARα subtype or for the PPAR subtype.

EXAMPLE 30

Compositions

Various actual formulations based on the compounds according to the invention are illustrated in this example.

Oral Route:

(a) Tablet of 0.2 g:

| Compound from Example 1 | 0.001 g |
|---|---|
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Oral Suspension in 5-ml Ampoules:

| Compound from Example 3 | 0.001 g |
|---|---|
| Glycerol | 0.500 g |
| Sorbitol at 70% | 0.500 g |
| Saccharin sodium | 0.010 g |
| Methyl parahydroxybenzoate | 0.040 g |
| Aroma | qs |
| Purified water | qsf 5 ml |

(c) Tablet of 0.2 g:

| Compound from Example 6 | 0.050 g |
|---|---|
| Lactose monohydrate | 0.132 g |
| Crospovidone | 0.007 g |
| Povidone | 0.005 g |
| Aerosil 200 | 0.004 g |
| Magnesium stearate | 0.002 g |

(d) Oral Suspension in 10-ml Ampoules:

| Compound from Example 7 | 0.200 g |
|---|---|
| Glycerol | 1.000 g |
| Sorbitol at 70% | 1.000 g |
| Saccharin sodium | 0.010 g |
| Methyl parahydroxybenzoate | 0.080 g |
| Aroma | qs |
| Purified water | q.s.f. 10 ml |

B—Topical Route:

(a) Unguent:

| Compound from Example 8 | 0.020 g |
|---|---|
| Isopropyl myristate | 81.700 g |
| Fluid vaseline oil | 9.100 g |
| Silica ("Aerosil 200") | 9.180 g |

(b) Unguent:

| Compound from Example 3 | 0.300 g |
|---|---|
| White petroleum jelly codex | q.s.f. 100 g |

(c) Cream, Water-in-Oil, Non-Ionic:

| Compound from Example 1 | 0.100 g |
|---|---|
| Mixture of emulsive lanolin alcohols, waxes and oils ("Eucerine anhydrous") | 39.900 g |
| Methyl parahydroxybenzoate | 0.075 g |
| Propyl parahydroxybenzoate | 0.075 g |
| Sterile demineralized water | q.s.f. 100 g |

(d) Lotion:

| Compound from Example 3 | 0.100 g |
|---|---|
| Polyethylene glycol (PEG 400) | 69.900 g |
| Ethanol at 95% | 30.000 g |

(e) Hydrophobic Unguent:

| Compound from Example 6 | 0.300 g |
|---|---|
| Isopropyl myristate | 36.400 g |
| Silicone oil ("Rhodorsil 47 V 300") | 36.400 g |
| Beeswax | 13.600 g |
| Silicone oil ("Abil 300 000 cSt") | q.s.f. 100 g |

(f) Cream, Oil-in-Water, Non-Ionic:

| Compound from Example 9 | 1.000 g |
|---|---|
| Cetyl alcohol | 4.000 g |
| Glycerol monostearate | 2.500 g |
| Stearate of PEG 50 | 2.500 g |
| Shea butter | 9.200 g |
| Propylene glycol | 2.000 g |
| Methyl parahydroxybenzoate | 0.075 g |
| Propyl parahydroxybenzoate | 0.075 g |
| Sterile demineralized water | q.s.f. 100 g |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A 3-phenyl acrylic acid compound having the following formula (I):

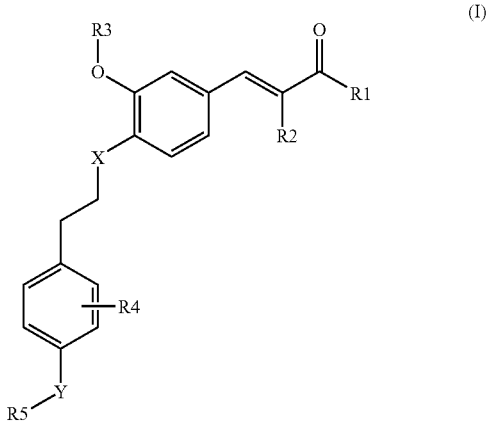

in which:
R1 is a hydroxyl radical or an alkoxy radical;
R2 is an alkyl radical or an alkoxy radical or an aralkoxy radical;
R3 is hydrogen atom, a butyl radical or an optionally substituted aralkyl radical, or OR3 is a polyether radical;
R4 is a hydrogen, a halogen, an alkyl radical or an alkoxy radical;
R5 is an alkyl radical, an optionally substituted aryl radical or an optionally substituted aralkyl radical;
X is a CH$_2$ radical;
Y is an oxygen atom, an NR6 radical, a radical OSO$_2$, OCO, NR6CO or NR6SO$_2$,
R6 is a hydrogen atom or an alkyl radical;

or a salt thereof with a pharmaceutically acceptable acid or base, or a pharmaceutically acceptable solvate or hydrate thereof.

2. The compound as defined by claim 1, in the form of a salt of an alkali metal or alkaline-earth metal or of a salt of an organic amine.

3. The compound as defined by claim 1, wherein, when it possesses an amine function, it is in the form of a salt of an inorganic acid or a salt of an organic acid.

4. The compound as defined by claim 1, wherein at least one of R2, R4, R5 and R6 comprises an alkyl radical that is a linear or branched saturated hydrocarbon chain, having from 1 to 12 carbon atoms.

5. The compound as defined by claim 1, wherein at least one of R2, R4, R5 and R6 comprises an alkyl radical that is selected from the group consisting of methyl, ethyl, propyl, isopropyl, butyl, isobutyl, tert-butyl, pentyl, isoamyl, amyl and hexyl radicals.

6. The compound as defined by claim 1, wherein R5 comprises an optionally substituted aryl radical selected from the group consisting of a phenyl and a naphthyl optionally substituted with one or more atoms or groups of atoms selected from the group consisting of an alkyl, an alkoxy, a halogen, a hydroxy, a cyano, a trifluoromethyl and a nitro.

7. The compound as defined by claim 1, wherein at least one of R3 and R5 comprises an optionally substituted aralkyl radical selected from the group consisting of benzyl and phenethyl radicals optionally substituted with one or more atoms or groups of atoms selected from the group consisting of an alkyl, an alkoxy, a halogen, a hydroxy, a cyano, a trifluoromethyl and a nitro substituent.

8. The compound as defined by claim 1, wherein R4 is a halogen atom selected from the group consisting of atoms of fluorine, of chlorine, of bromine and of iodine.

9. The compound as defined by claim 1, wherein at least one of R1, R2 and R4 comprises an alkoxy radical selected from the group consisting of methoxy, ethoxy, isopropyloxy, n-propyloxy, tert-butoxy, n-butoxy, n-pentyloxy and n-hexyloxy radicals.

10. The compound as defined by claim 1, selected from the group consisting of:
(Z)-3-(4-{3-[4-(butane-1-sulfonyloxy)-3-methoxy-phenyl]-propyl}-3-butoxy-phenyl)-2-methoxy-acrylic acid;
(Z)-3-(4-{3-[4-(butane-1-sulfonyloxy)-3-methoxy-phenyl]-propyl}-3-butoxy-phenyl)-2-ethoxy-acrylic acid;
(E)-3-(4-{3-[4-(butane-1-sulfonyloxy)-3-methoxy-phenyly]-propyl}-3-butoxy-phenyl)-2-methyl-acrylic acid;
(Z)-3-{3-butoxy-4-[3-(4-methoxy-phenyl)-propyl]-phenyl}-2-ethoxy-acrylic acid;
(E)-3-(4-{3-[4-(butane-1-sulfonyloxy)-phenyl]-propyl}-3-butoxy-phenyl)-2-methoxy-acrylic acid;
(Z)-3-[4-{3-[4-(butane-1-sulfonyloxy)-phenyl]-propyl}-3-(2-ethoxy-ethoxy)phenyl]-2-methoxy-methyl acrylate;
(Z)-3-{3-benzyloxy-4-[3-(4-m-tolylmethanesulfonyloxy-phenyl)-propyl]-phenyl}-2-methoxy-acrylic acid; and
(Z)-3-{3-hydroxy-4-[3-(4-m-tolylmethanesulfonyloxy-phenyl)-propyl]-phenyl}-2-methoxy-acrylic acid.

11. The compound as defined by claim 1, having at least one of the following characteristics:
R1 is a hydroxyl radical,
R2 is a lower alkyl radical or a lower alkoxy radical,
R3 is a butyl radical or OR3 is a polyether radical,
R4 is a hydrogen atom, a lower alkoxy radical or a halogen,
R5 is an alkyl radical,
X is a CH$_2$ group,
Y is a group —NR6SO$_2$ or a group —OSO$_2$, and
R6 is a hydrogen atom or an alkyl radical.

12. The compound as defined by claim 1, having at least one of the following characteristics:
R1 is a hydroxyl radical,
R2 is a lower alkoxy radical,
R3 is a butyl radical,
R4 is a hydrogen atom, a lower alkoxy radical or a halogen,
R5 is an alkyl radical,
X is a CH$_2$ group, and
Y is a group —OSO$_2$.

13. A cosmetic composition comprising at least one compound of formula (I) as defined by claim 1, formulated into a cosmetically applicable, physiologically acceptable medium.

14. The cosmetic composition as defined by claim 13, having a concentration of compound of formula (I) ranging from 0.001% to 3 wt. % relative to the total weight of the composition.

15. A regime or regimen for body or hair hygiene, comprising topically applying thereon a thus effective amount of the cosmetic composition as defined by claim 13.

16. A regime or regimen to regulate and/or restore the metabolism of skin lipids, comprising administering to an individual in need of such treatment, a thus effective amount of a compound of formula (I) as defined by claim 1.

17. A method for the treatment of acne vulgaris, comedo acne, polymorphic acne, nodulocystic acne, acne conglobata, senile acne, secondary acne or cutaneous, mucosal or ungual psoriasis, said method comprising administering to an individual in need of such treatment a thus effective amount of a compound of formula (I) as defined by claim 1.

18. A pharmaceutical composition comprising at least one compound of formula (I) as defined by claim 1, formulated into a physiologically acceptable medium.

19. The pharmaceutical composition as defined by claim 18, having a concentration of compound(s) of formula (I) ranging from 0.001% to 10 wt. % relative to the total weight of the composition.

20. The pharmaceutical composition as defined by claim 19, having a concentration of compound(s) of formula (I) ranging from 0.01% to 1 wt. % relative to the total weight of the composition.

21. A method for selectively activating receptors of the PPARγ-type, said method comprising contacting said receptors with a PPARγ receptor activating amount of at least one 3-phenyl acrylic acid compound of formula (I) as defined by claim 1.

22. A 3-phenyl acrylic acid compound having the following formula (I):

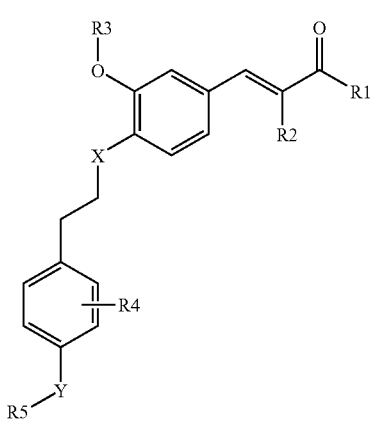

in which:
R1 is a hydroxyl radical or an alkoxy radical;
R2 is an alkoxy radical;
R3 is a butyl radical;
R4 is a hydrogen, a halogen or an alkoxy radical;
R5 is an alkyl radical, an optionally substituted aryl radical or an optionally substituted aralkyl radical;
X is a CH$_2$ radical;
Y is an oxygen atom, an NR6 radical, a radical OSO$_2$, OCO, NR6CO or NR6SO$_2$,
R6 is a hydrogen atom or an alkyl radical;
or a salt thereof with a pharmaceutically acceptable acid or base, or a pharmaceutically acceptable solvate or hydrate thereof.

23. The compound as defined by claim 22, in the form of a salt of an alkali metal or alkaline-earth metal or of a salt of an organic amine.

24. The compound as defined by claim 22, wherein, when it possesses an amine function, it is in the form of a salt of an inorganic acid or a salt of an organic acid.

25. The compound as defined by claim 22, wherein at least one of R5 and R6 comprises an alkyl radical that is a linear or branched saturated hydrocarbon chain, having from 1 to 12 carbon atoms.

26. The compound as defined by claim 22, wherein at least one of R5 and R6 comprises an alkyl radical that is selected from the group consisting of methyl, ethyl, propyl, isopropyl, butyl, isobutyl, tert-butyl, pentyl, isoamyl, amyl and hexyl radicals.

27. The compound as defined by claim 22, wherein R5 comprises an optionally substituted aralkyl radical selected from the group consisting of benzyl and phenethyl radicals optionally substituted with one or more atoms or groups of atoms selected from the group consisting of an alkyl, an alkoxy, a halogen, a hydroxy, a cyano, a trifluoromethyl and a nitro substituent.

28. The compound as defined by claim 22, wherein at least one of R1, R2 and R4 comprises an alkoxy radical selected from the group consisting of methoxy, ethoxy, isopropyloxy, n-propyloxy, tert-butoxy, n-butoxy, n-pentyloxy and n-hexyloxy radicals.

29. A pharmaceutical composition comprising at least one compound of formula (I) as defined by claim 22, formulated into a physiologically acceptable medium.

30. The pharmaceutical composition as defined by claim 29, having a concentration of compound(s) of formula (I) ranging from 0.001% to 10 wt. % relative to the total weight of the composition.

31. The pharmaceutical composition as defined by claim 30, having a concentration of compound(s) of formula (I) ranging from 0.01% to 1 wt. % relative to the total weight of the composition.

32. A method for selectively activating receptors of the PPARγ-type, said method comprising contacting said receptors with a PPARγ-type receptor activating amount of at least one 3-phenyl acrylic acid compound of formula (I) as defined by claim 22.

33. A 3-phenyl acrylic acid compound having the following formula (I):

(I)

in which:
R1 is a hydroxyl radical or an alkoxy radical;
R2 is an alkoxy radical;
R3 is a butyl radical;
R4 is a hydrogen, a halogen or an alkoxy radical;
R5 is a butyl radical;
X is an oxygen atom or a CH$_2$ radical;
Y is a radical OSO$_2$;
or a salt thereof with a pharmaceutically acceptable acid or base, or a pharmaceutically acceptable solvate or hydrate thereof.

34. The compound as defined by claim 33, in the form of a salt of an alkali metal or alkaline-earth metal or of a salt of an organic amine.

35. The compound as defined by claim 33, wherein, when it possesses an amine function, it is in the form of a salt of an inorganic acid or a salt of an organic acid.

36. The compound as defined by claim 33, selected from the group consisting of:
(Z)-3-(4-{3-[4-(butane-1-sulfonyloxy)-3-methoxy-phenyl]-propyl}-3-butoxy-phenyl)-2-ethoxy-acrylic acid;
(Z)-3-(4-{2-[4-(butane-1-sulfonyloxy)-phenyl]-ethoxy}-3-butoxy-phenyl)-2-ethoxy-acrylic acid;
(Z)-3-(4-{2-[4-(butane-1-sulfonyloxy)-3-methoxy phenyl]-ethoxy}-3-butoxy-phenyl)-2-ethoxy-acrylic acid;
(Z)-3-(4-{2-[4-(butane-1-sulfonyloxy)-2-methoxy-phenyl]-ethoxy}-3-butoxy-phenyl)-2-ethoxy-acrylic acid;
(Z)-3-(4-{2-[4-(butane-1-sulfonyloxy)-3-fluoro-phenyl]-ethoxy}-3-butoxy-phenyl)-2-ethoxy-acrylic acid; and
(Z)-3-(4-{2-[4-(butane-1-sulfonyloxy)-3-chloro-phenyl]-ethoxy}-3-butoxy-phenyl)-2-ethoxy-acrylic acid.

37. The compound of claim 36, which is (Z)-3-(4-{2-[4-(butane-1-sulfonyloxy)-phenyl]-ethoxy}-3-butoxy-phenyl)-2-ethoxy-acrylic acid.

38. A 3-phenyl acrylic acid compound having the following formula (I):

(I)

in which:
R1 is a hydroxyl radical or an alkoxy radical;
R2 is an alkyl radical or an alkoxy radical;
R3 is a hydrogen atom, an alkyl radical, or an optionally substituted aralkyl radical or —OR3 is a polyether radical;
R4 is a hydrogen, a halogen, an alkyl radical or an alkoxy radical;
R5 is a butyl radical;
X is a CH$_2$ radical;
Y is a radical OSO$_2$ or NR6SO$_2$,
R6 is a hydrogen atom or an alkyl radical;
or a salt thereof with a pharmaceutically acceptable acid or base, or a pharmaceutically acceptable solvate or hydrate thereof.

39. The compound as defined by claim 38, wherein at least one of R2, R3, R4 and R6 comprises an alkyl radical that is a linear or branched saturated hydrocarbon chain, having from 1 to 12 carbon atoms.

40. The compound as defined by claim 38, wherein at least one of R2, R3, R4 and R6 comprises an alkyl radical that is selected from the group consisting of methyl, ethyl, propyl, isopropyl, butyl, isobutyl, tert-butyl, pentyl, isoamyl, amyl and hexyl radicals.

41. The compound as defined by claim 38, wherein at least one of R1, R2 and R4 comprises an alkoxy radical selected from the group consisting of methoxy, ethoxy, isopropyloxy, n-propyloxy, tert-butoxy, n-butoxy, n-pentyloxy and n-hexyloxy radicals.

42. The compound as defined by claim 38, selected from the group consisting of:
(Z)-3-(4-{3-[4-(butane-1-sulfonyloxy)-3-methoxy-phenyl]-propyl}-3-butoxy-phenyl)-2-methoxy-acrylic acid;
(Z)-3-(4-{3-[4-(butane-1-sulfonyloxy)-3-methoxy-phenyl]-propyl}-3-butoxy-phenyl)-2-ethoxy-acrylic acid;
(E)-3-(4-{3-[4-(butane-1-sulfonyloxy)-3-methoxy-phenyl]-propyl}-3-butoxy-phenyl)-2-methyl-acrylic acid;
(E)-3-(4-{3-[4-(butane-1-sulfonyloxy)-phenyl]-propyl}-3-butoxy-phenyl)-2-methoxy-acrylic acid; and
(Z)-3-[4-{3-[4-(butane-1-sulfonyloxy)-phenyl]-propyl}-3-(2-ethoxy-ethoxy)-phenyl]-2-methoxy-methyl acrylate.

43. The compound as defined by claim 38, having at least one of the following characteristics:
R1 is a hydroxyl radical,
R2 is a lower alkyl radical or a lower alkoxy radical,
R3 is an alkyl radical or —OR3 is a polyether radical, R4 is a hydrogen atom, a lower alkoxy radical or a halogen,
R5 is a butyl radical,
X is a $CH_2$ group,
Y is a group $-NR6SO_2$ or a group $-OSO_2$, and
R6 is a hydrogen atom or an alkyl radical.

44. The compound as defined by claim 38, having at least one of the following characteristics:
R1 is a hydroxyl radical,
R2 is a lower alkoxy radical,
R3 is an alkyl radical,
R4 is a hydrogen atom, a lower alkoxy radical or a halogen,
R5 is a butyl radical,
X is a $CH_2$ group, and
Y is a group $-OSO_2$.

* * * * *